United States Patent
Kaneko et al.

(10) Patent No.: US 11,097,007 B2
(45) Date of Patent: *Aug. 24, 2021

(54) INJECTABLE PREPARATION

(71) Applicant: OTSUKA PHARMACEUTICAL CO., LTD., Tokyo (JP)

(72) Inventors: Daiki Kaneko, Osaka (JP); Takakuni Matsuda, Osaka (JP); Yusuke Hoshika, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/108,939

(22) Filed: Dec. 1, 2020

(65) Prior Publication Data

US 2021/0085794 A1    Mar. 25, 2021

Related U.S. Application Data

(63) Continuation of application No. 16/785,268, filed on Feb. 7, 2020, now abandoned, which is a continuation of application No. 16/514,973, filed on Jul. 17, 2019, now abandoned, which is a continuation of application No. 16/156,958, filed on Oct. 10, 2018, now Pat. No. 10,517,951, which is a continuation of application No. 15/701,202, filed on Sep. 11, 2017, now abandoned, which is a continuation of application No. 14/396,380, filed as application No. PCT/JP2013/062683 on Apr. 23, 2013, now abandoned.

(60) Provisional application No. 61/636,938, filed on Apr. 23, 2012, provisional application No. 61/792,089, filed on Mar. 15, 2013.

(51) Int. Cl.
| | | |
|---|---|---|
| A61K 47/32 | (2006.01) | |
| A61K 9/00 | (2006.01) | |
| A61K 47/10 | (2017.01) | |
| A61K 9/06 | (2006.01) | |
| A61K 47/38 | (2006.01) | |
| A61K 31/496 | (2006.01) | |

(52) U.S. Cl.
CPC ........... *A61K 47/32* (2013.01); *A61K 9/0019* (2013.01); *A61K 9/06* (2013.01); *A61K 31/496* (2013.01); *A61K 47/10* (2013.01); *A61K 47/38* (2013.01); *A61K 9/0024* (2013.01)

(58) Field of Classification Search
None
See application file for complete search history.

(56) References Cited

U.S. PATENT DOCUMENTS

| | | | |
|---|---|---|---|
| 5,006,528 A | 4/1991 | Oshiro et al. | |
| 5,192,802 A | 3/1993 | Rencher | |
| 8,575,172 B2 | 11/2013 | Wilding et al. | |
| 9,241,876 B2 | 1/2016 | Zheng et al. | |
| 2002/0076437 A1 | 6/2002 | Kathari et al. | |
| 2005/0032836 A1 | 2/2005 | Greco et al. | |
| 2005/0089557 A1 | 4/2005 | Kawasaki | |
| 2007/0110784 A1 | 5/2007 | Chen et al. | |
| 2008/0214995 A1 | 9/2008 | Boyd et al. | |
| 2009/0258850 A1 | 10/2009 | Frincke et al. | |
| 2010/0015195 A1* | 1/2010 | Jain | A61P 13/08 424/422 |
| 2010/0137292 A1* | 6/2010 | Turp | A61K 9/08 514/226.5 |
| 2010/0196486 A1* | 8/2010 | Hiraoka | A61K 9/19 424/489 |
| 2012/0091022 A1 | 4/2012 | Nakagawa et al. | |
| 2012/0258971 A1 | 10/2012 | Niwa et al. | |
| 2014/0005610 A1 | 1/2014 | Kakiuichi et al. | |
| 2014/0135343 A1 | 5/2014 | Zheng et al. | |
| 2014/0234417 A1 | 8/2014 | Inoue | |
| 2015/0086632 A1 | 3/2015 | Sato et al. | |

FOREIGN PATENT DOCUMENTS

| | | |
|---|---|---|
| CN | 102846543 A | 1/2013 |
| GB | 864100 | 3/1961 |
| JP | 9-301867 | 11/1997 |
| JP | 2003-171264 A | 6/2003 |
| JP | 2006-219380 A | 8/2006 |
| JP | 2007-509148 A | 4/2007 |
| JP | 2007-517902 A | 7/2007 |
| JP | 2008-115172 | 5/2008 |

(Continued)

OTHER PUBLICATIONS

Gavina et al. "Indirect and direct temperature calibration methodology of a rheometer using a Newtonian reference material" Journal of Physics:Conf, Series 1065 (2018).*

(Continued)

*Primary Examiner* — Danah Al-Awadi

(74) *Attorney, Agent, or Firm* — Finnegan, Henderson, Farabow, Garrett & Dunner, LLP

(57) ABSTRACT

An object of the present invention is to provide a storage-stable injectable preparation comprising a composition comprising a poorly soluble drug as an active ingredient and a dispersion medium. Another object of the present invention is to provide a compact, lightweight prefilled syringe by filling a syringe with the injectable preparation. The present invention provides an injectable preparation comprising a composition comprising a poorly soluble drug, a dispersion medium, and a specific suspending agent, the composition having a viscosity of 40 pascal-seconds or more in at least one point in the shear rate range of 0.01 to 0.02 $s^{-1}$ and having a viscosity of 0.2 pascal-seconds or less in at least one point in the shear rate range of 900 to 1,000 $s^{-1}$, as measured.

24 Claims, 26 Drawing Sheets

(56) References Cited

FOREIGN PATENT DOCUMENTS

| | | |
|---|---|---|
| JP | 2009-286740 | 12/2009 |
| JP | 2012-121850 | 6/2012 |
| JP | 2012-232958 A | 11/2012 |
| JP | 2013-139441 | 7/2013 |
| NZ | 204870 A | 6/1986 |
| WO | WO 02/060423 | 8/2002 |
| WO | WO 02/085366 | 10/2002 |
| WO | WO 03/026659 | 4/2003 |
| WO | WO 03/030868 | 4/2003 |
| WO | WO 03/068194 | 8/2003 |
| WO | WO 2004/017897 | 3/2004 |
| WO | WO 2004/060374 | 7/2004 |
| WO | WO 2004/063162 | 7/2004 |
| WO | WO 2004/064752 | 8/2004 |
| WO | WO 2004/105682 | 12/2004 |
| WO | WO 2005/016262 | 2/2005 |
| WO | WO 2005/041937 A2 | 5/2005 |
| WO | WO 2005/041970 | 5/2005 |
| WO | WO 2005/070332 A1 | 8/2005 |
| WO | WO 2006/112464 | 10/2006 |
| WO | WO 2007/035348 | 3/2007 |
| WO | WO 2008/090632 | 7/2008 |
| WO | WO 2009/001697 | 12/2008 |
| WO | WO 2009/017250 | 2/2009 |
| WO | WO 2009/128537 A1 | 10/2009 |
| WO | WO 2010/138539 | 12/2010 |
| WO | WO 2011/030575 | 3/2011 |
| WO | WO 2012/026562 A1 | 3/2012 |
| WO | WO 2012/067141 | 5/2012 |
| WO | WO 2012/102216 | 8/2012 |
| WO | WO 2012/137971 | 10/2012 |
| WO | WO 2012/169662 | 12/2012 |
| WO | WO 2013/002420 | 1/2013 |
| WO | WO 2013/015456 | 1/2013 |
| WO | WO 2013/035892 | 3/2013 |
| WO | WO 2013/054872 | 4/2013 |
| WO | WO 2013/058411 | 4/2013 |
| WO | WO 2013/100204 | 7/2013 |
| WO | WO 2013/133448 | 9/2013 |
| WO | WO 2013/161830 | 10/2013 |
| WO | WO 2013/162046 | 10/2013 |
| WO | WO 2013/162048 | 10/2013 |

OTHER PUBLICATIONS

Benchabane, Adel et al., "Rheological Properties of Carboxymethyl Cellulose," Colloid and Polymer Science, 2008, vol. 286, pp. 1173-1180.

Defu Cui et al., "Pharmacy", 2011, pp. 152-157.

Edali, Mohamed et al., "Rheological Properties of High Concentrations of Carboxymethyl Cellulose Solutions," Journal of Applied Polymer Science, 2001, vol. 79, pp. 1787-1801.

Communication of a notice of opposition dated Mar. 20, 2020 for the corresponding EP patent No. 2841054.

English-language International Search Report from the European Patent Office for International Application No. PCT/JP2013/062683 dated Jul. 18, 2013.

English-language Written Opinion of the International Search Authority from the European Patent Office for International Application No. PCT/JP2013/062683 dated Jul. 18, 2013.

Gavina, J. et al., "Indirect and direct temperature calibration methodology of a rheometer using a Newtonian reference material," J. Phys.: Conf. Ser. 1065 04055 (2018).

Ghannam, Mamdough T. et al., "Rheological Properties of Carboxymethyl Cellulose," Journal of Applied Polymer Science, 1997, vol. 64, No. 2, pp. 289-301.

Ghica, Mihaela Violeta et al., "Evaluation of Some Rheological Parameters for Sodium Carboxymethylcellulose Topical Hydrogels with Indomethacin," Farmacia, 2007, vol. 55, No. 6, pp. 671-679.

Handbook of Pharmaceutical Excipients. Pharmaceutical Press, RPS Publishing, 2009 (6th Ed) pp. 118-119 and 581-582.

M. T. Zafarani-Moattar et al., "Measurement and correlation of density and viscosity of polyvinylpyrrolidone solutions in alcohols at different temperatures", The Journal of Chemical Thermodynamics, vol. 40, 2008, pp. 1569-1574.

National Standard Textbook of Pharmacology for Medical College, Pharmaceutics, $2^{nd}$ Ed., 2011, Section 5.

Office Action for corresponding CO Patent Application No. NC2018/0004186 (formerly No. NC2017/0006541) dated Jun. 18, 2019.

Office Action dated May 4, 2016, issued for the corresponding NZ Patent Application No. 630335.

Office Action dated May 10, 2016, issued for the corresponding CN Patent Application No. 2013800214409.

Office Action for corresponding JP Application No. 2015-506529 dated Mar. 28, 2017.

Office Action for corresponding Philippines Office Action No. 1-2014-502379 dated Oct. 27, 2017.

The Acceptance of the Opposition filed by Lafrancol S.A.S. dated Apr. 17, 2015 for CO Patent Application No. 14-256422.

The Merck Index, "An Encyclopedia of Chemicals, Drugs and Biologicals", Fifteenth Edition, 2013, p. 135.

Yurong Wang et al., "Pharmacy", 2005, pp. 7-14.

Communication dated May 19, 2021, enclosing a letter from the opponent of May 12, 2021, for the corresponding EP Patent No. 2841054.

Excerpt from textbook "Rheology Modifiers Handbook", 1999 as downloaded from https://www.sciencedirect.com/topics/engineering/carboxymethylcellulose.

Office Action dated May 8, 2021, for the corresponding Chinese Patent Application No. 201810143716.5.

* cited by examiner

[Fig.1]
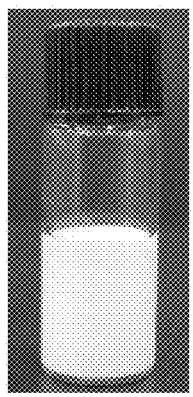
[Fig.2]
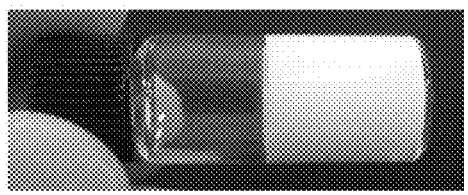
[Fig.3]
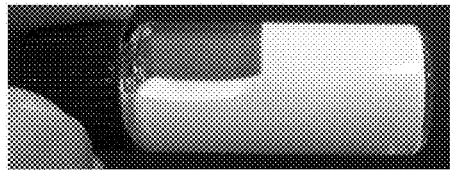

[Fig.4a]
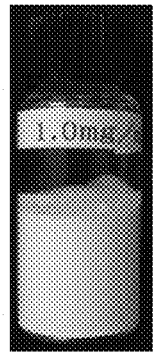
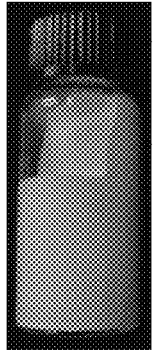
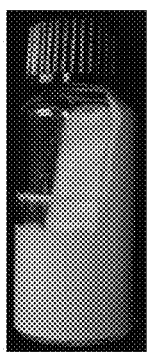
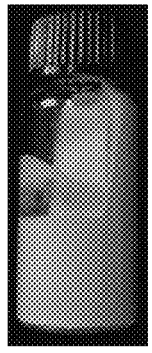
Povidone K17: 0.1 mg/mL    1.0 mg/mL    4.0 mg/mL
Povidone K17: 10.0 mg/mL   50.0 mg/mL   100 mg/mL

[Fig. 4b]
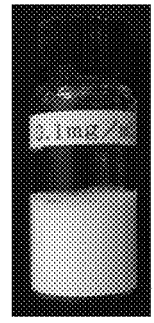
Povidone K17: 0.1 mg/mL
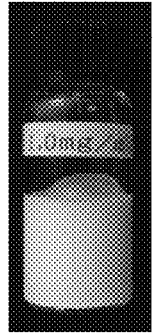
Povidone K17: 1.0 mg/mL
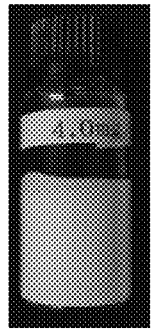
4.0 mg/mL
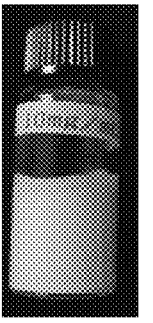
Povidone K17: 10.0 mg/mL
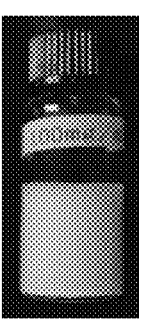
50.0 mg/mL
100 mg/mL

[Fig. 4c]
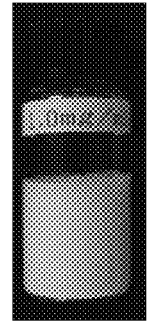
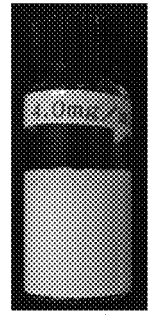
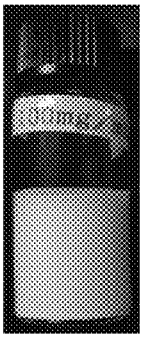
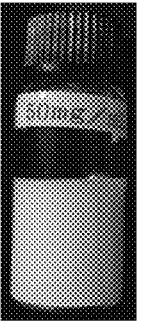
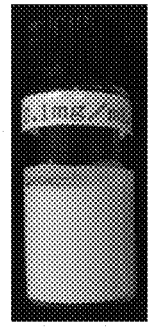
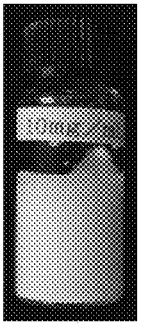
Povidone K17: 0.1 mg/mL
Povidone K17: 1.0 mg/mL
Povidone K17: 4.0 mg/mL
Povidone K17: 10.0 mg/mL
Povidone K17: 50.0 mg/mL
Povidone K17: 100 mg/mL

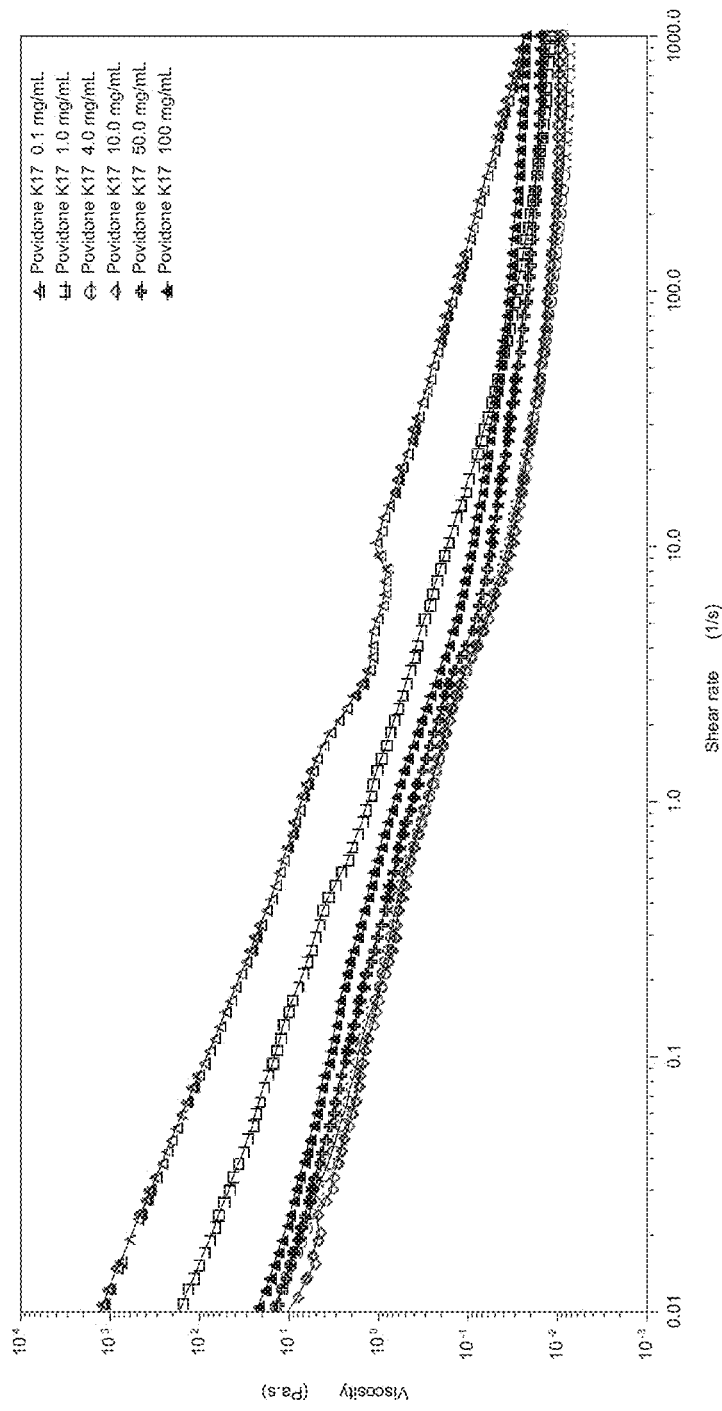
[Fig. 5a]

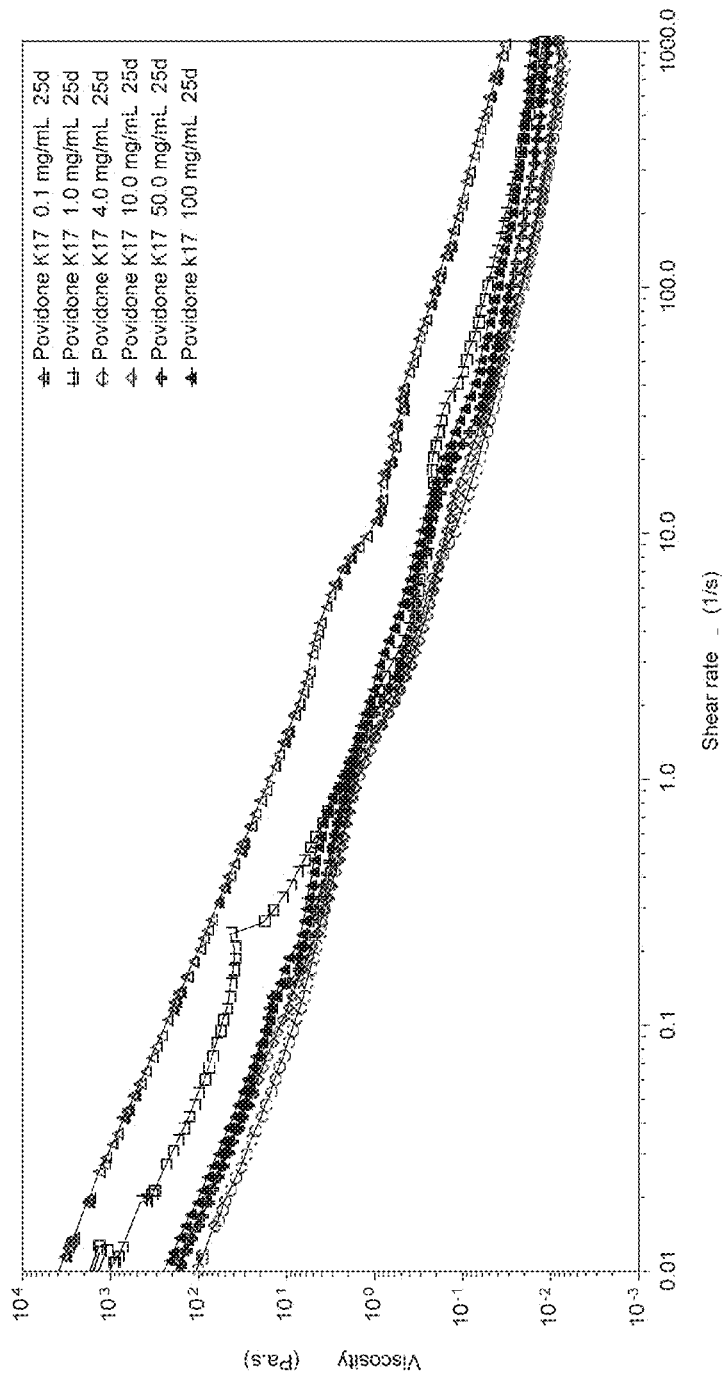
[Fig. 5b]

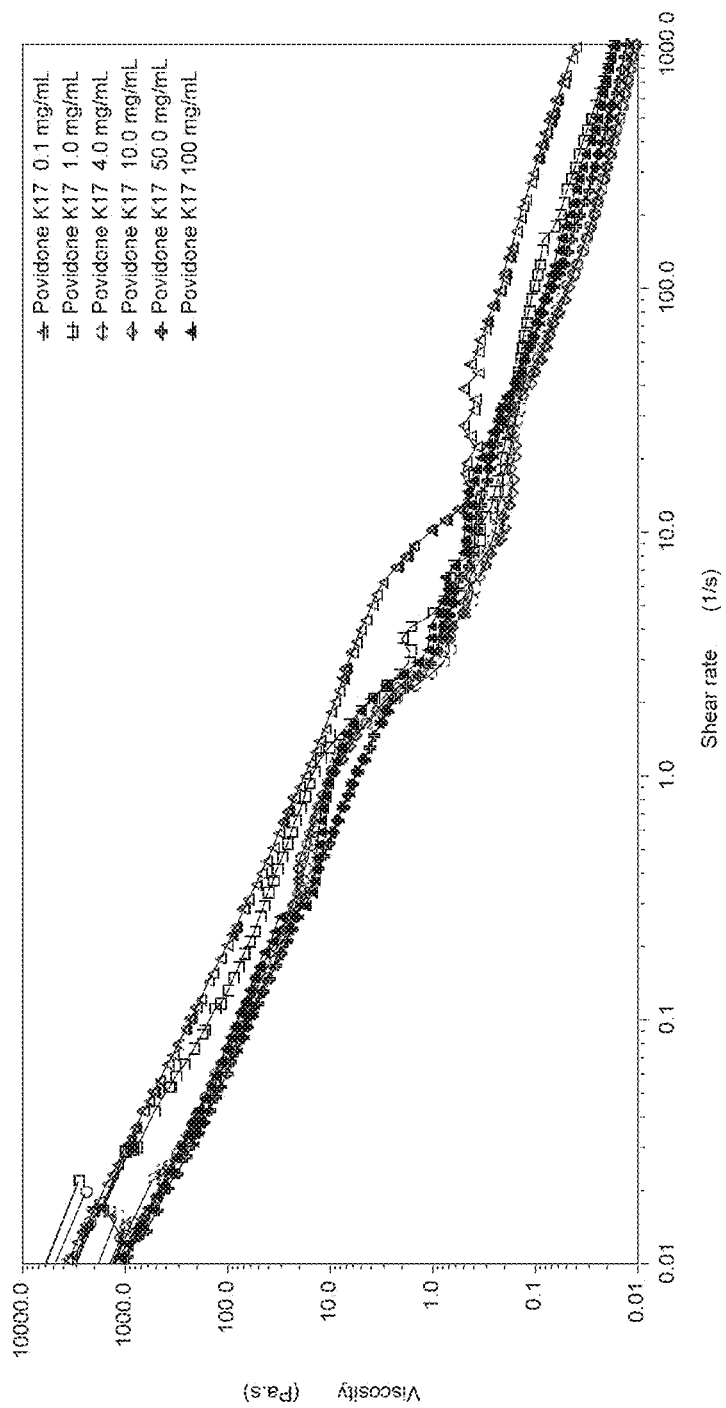
[Fig. 5c]

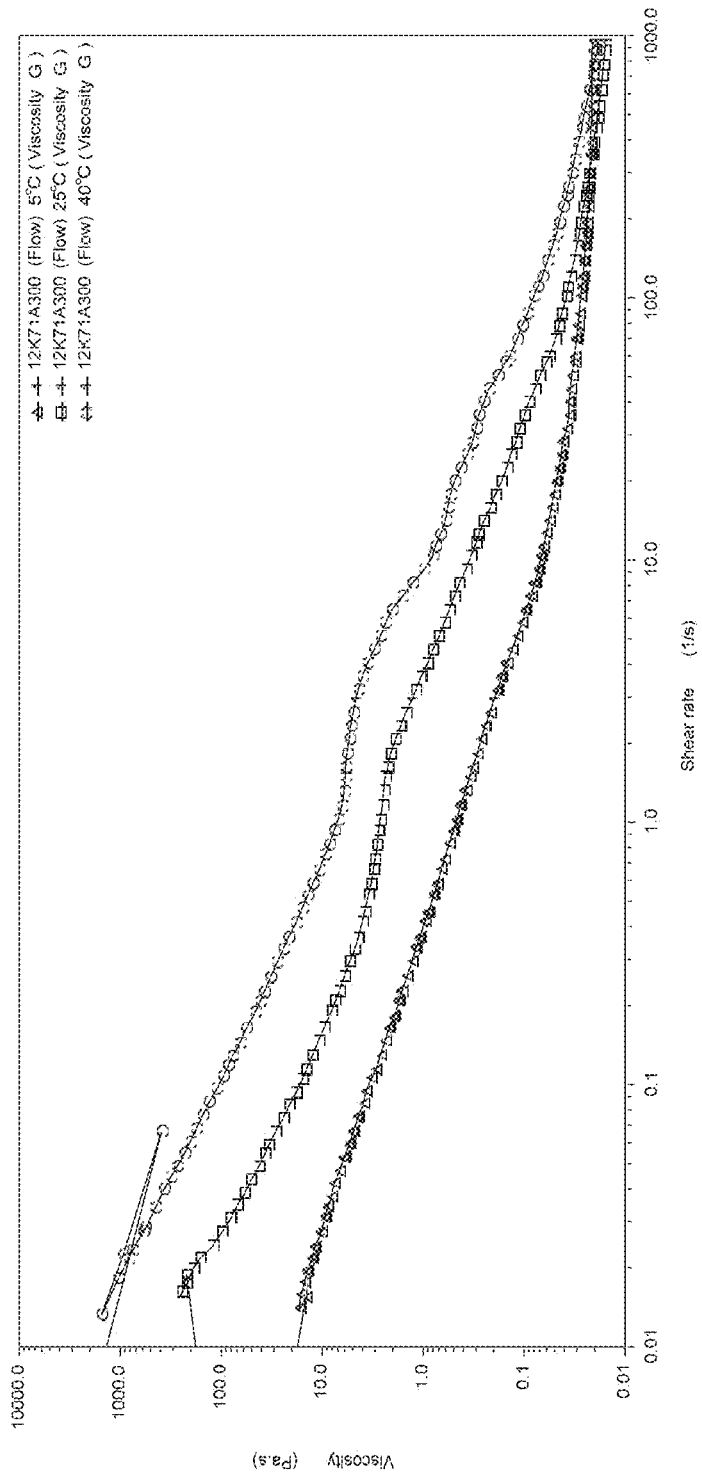
[Fig. 6]

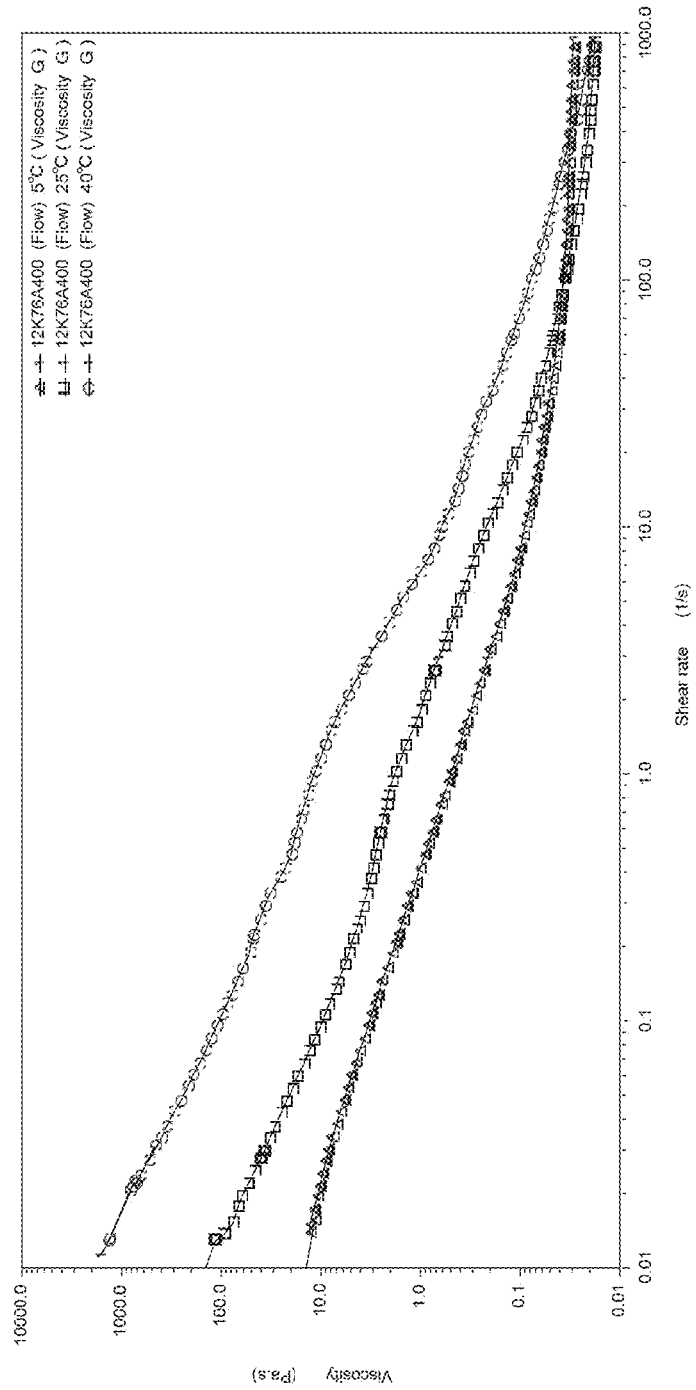
[Fig. 7]

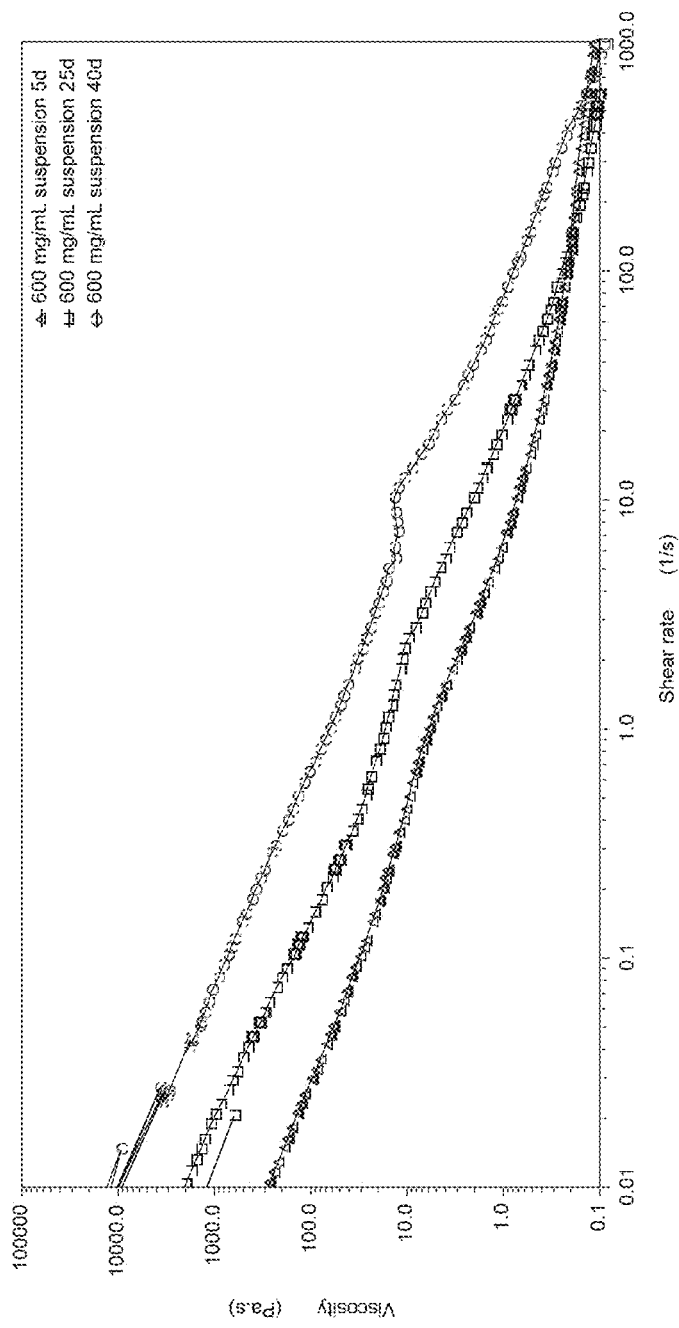
[Fig. 8]

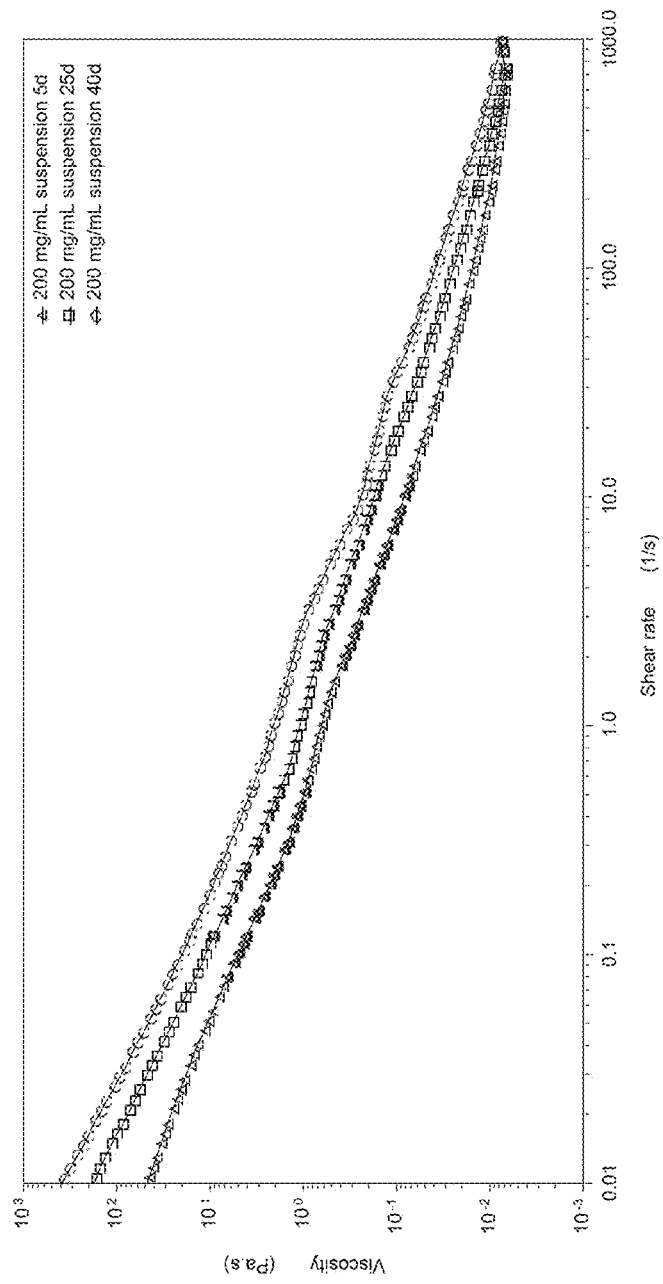
[Fig. 9a]

[Fig. 9b]
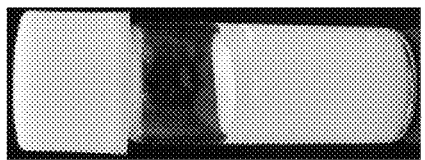
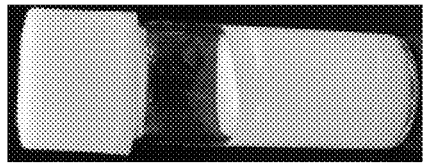
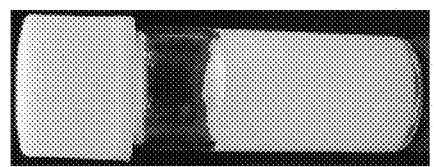
[Fig. 9c]
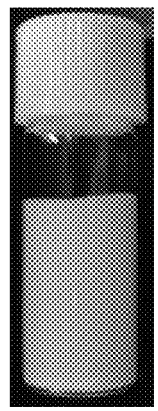
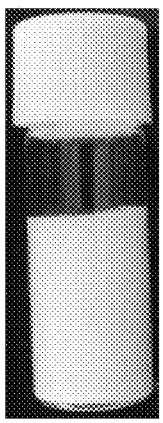
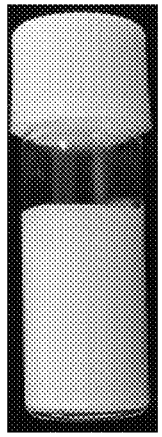

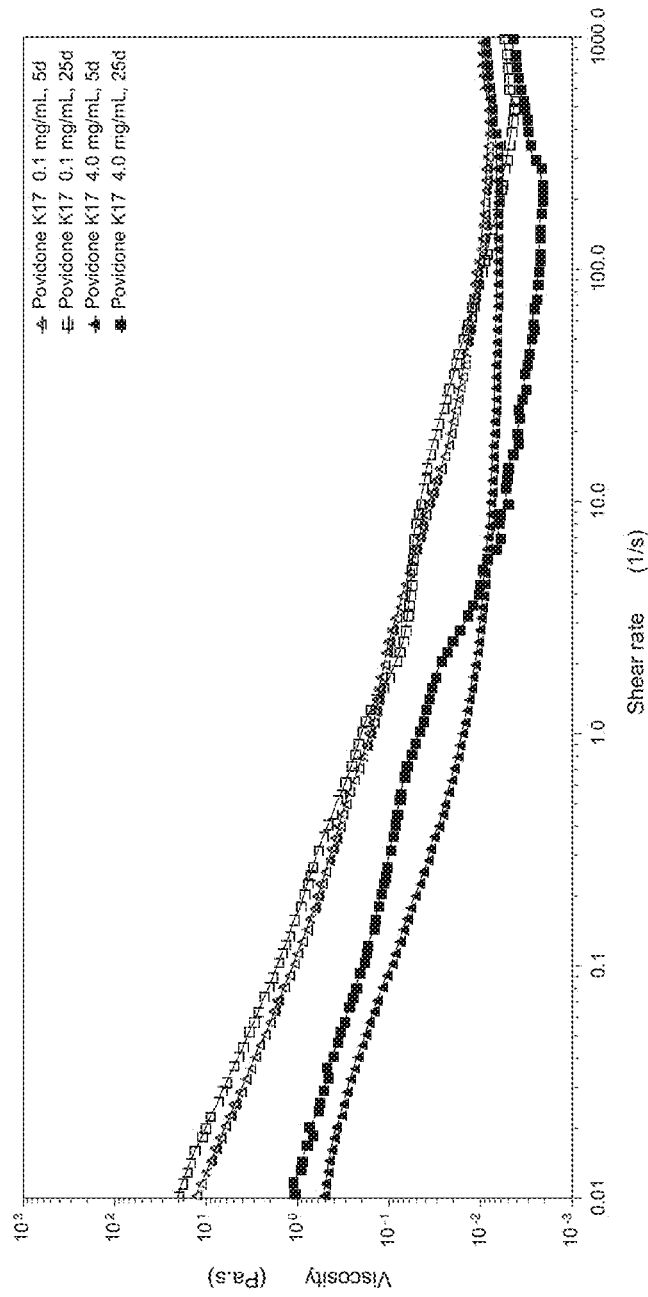
[Fig. 10a]

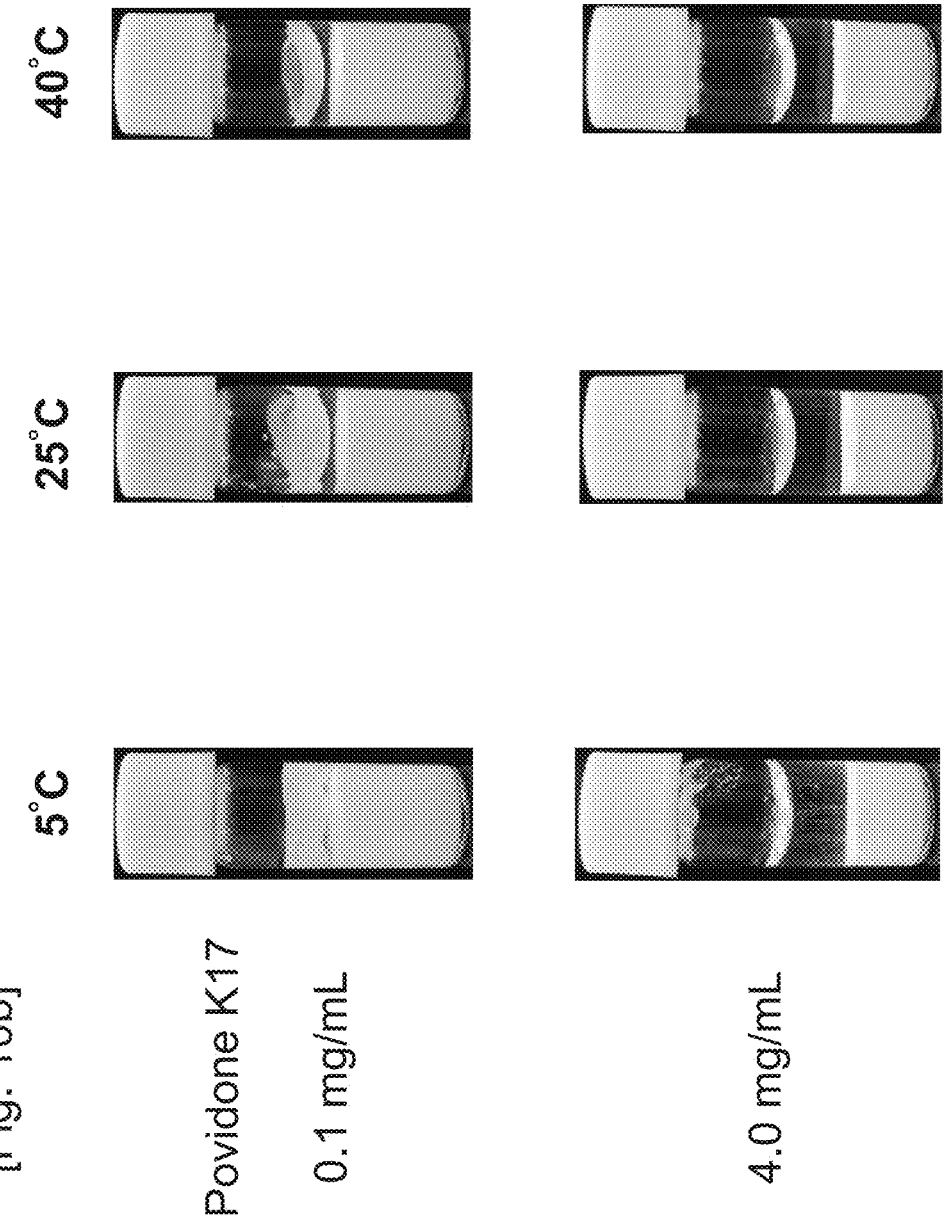

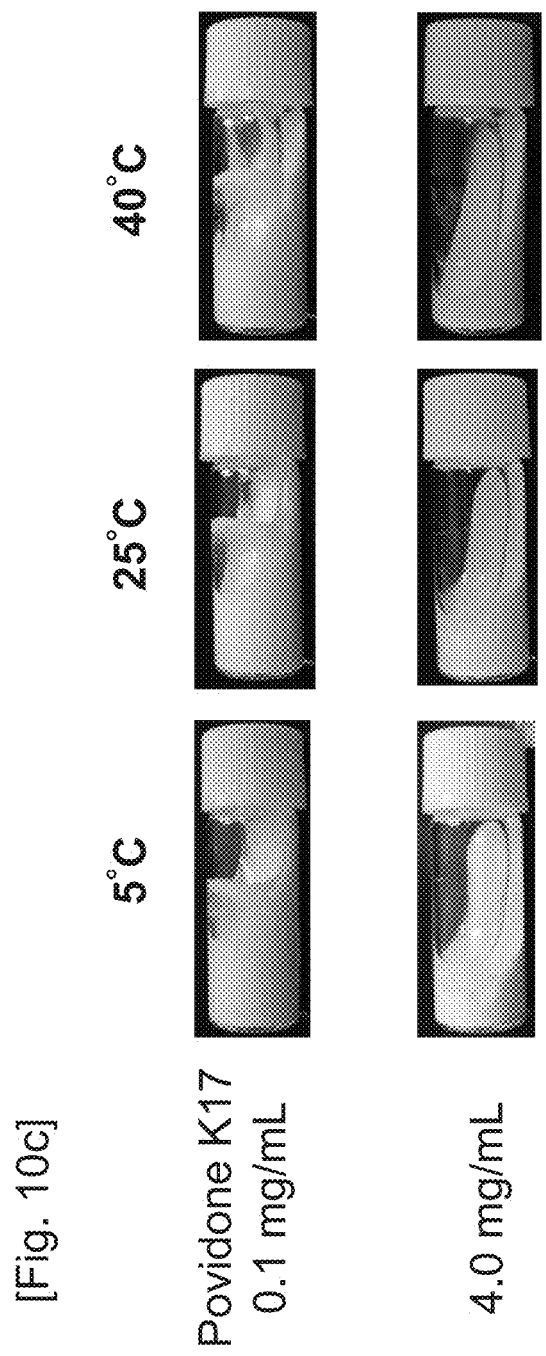

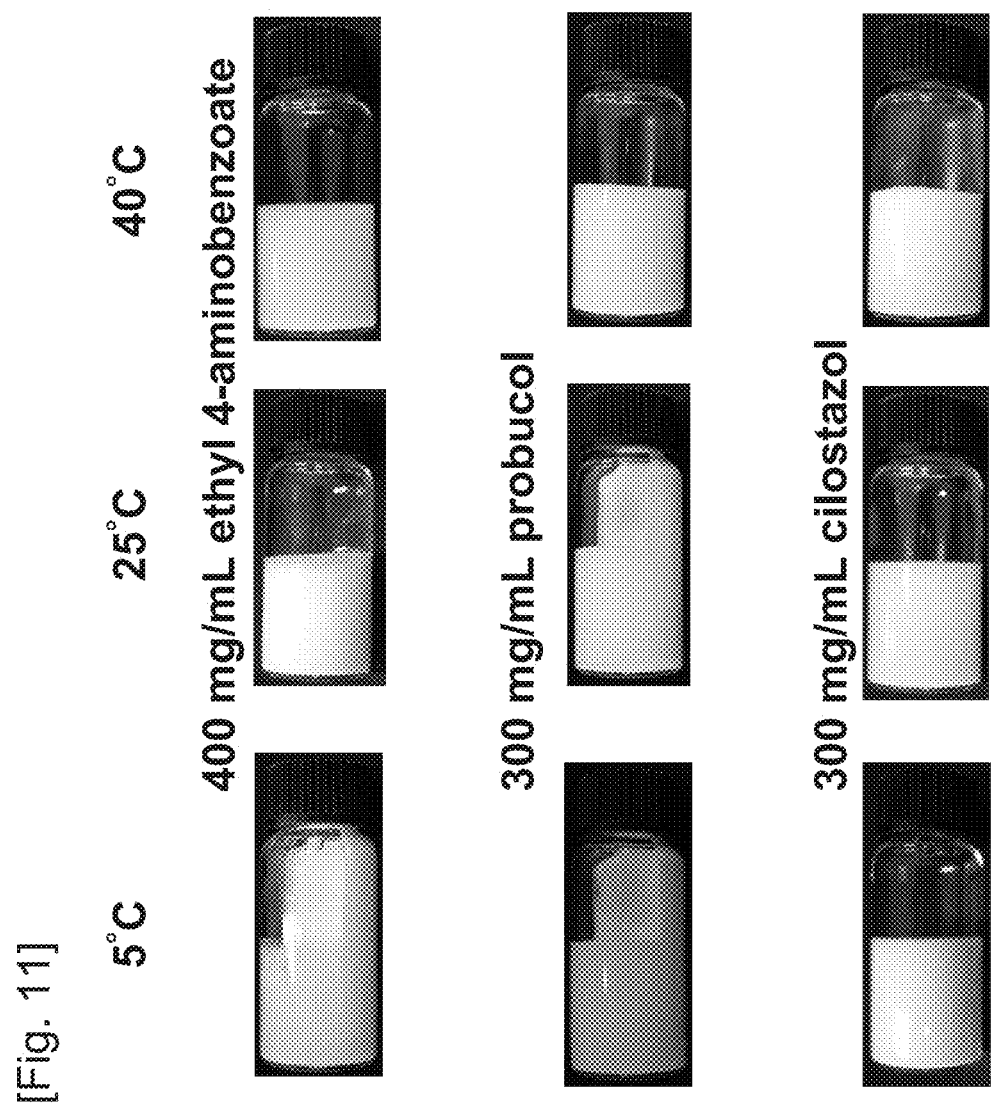
[Fig. 11]

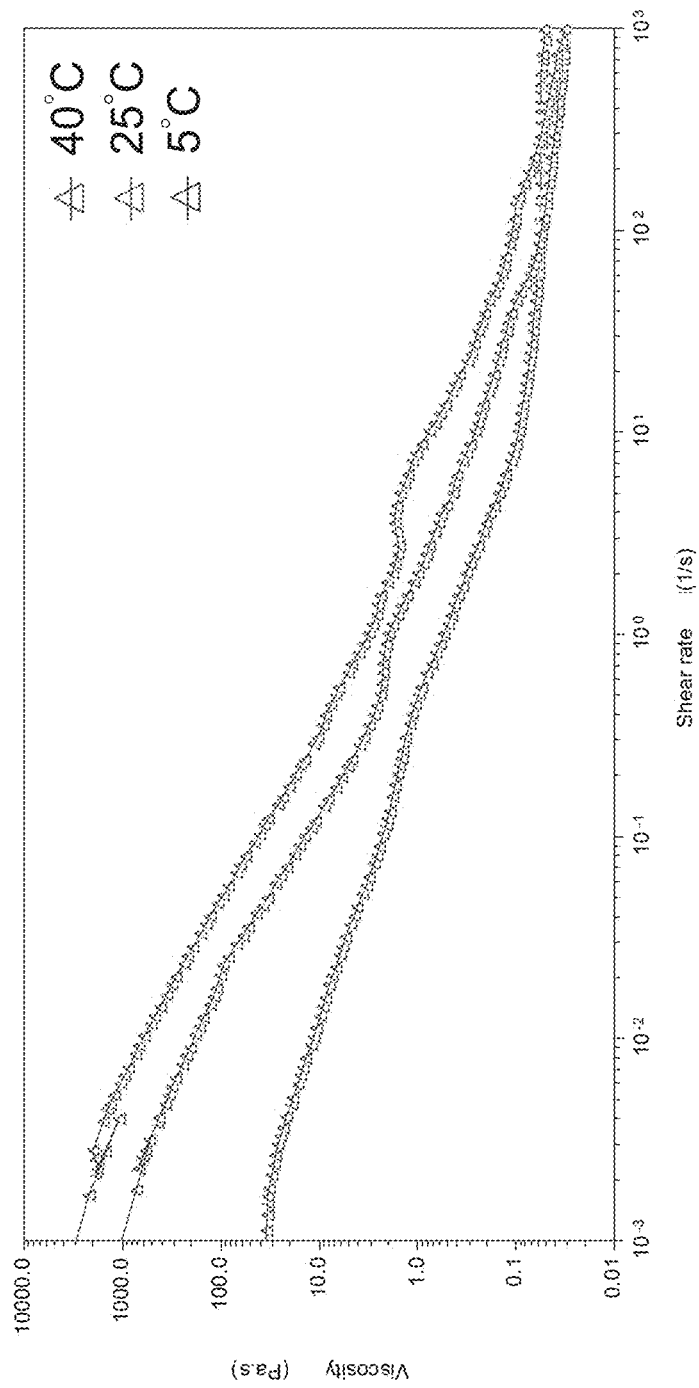
[Fig. 12]

[Fig. 13]
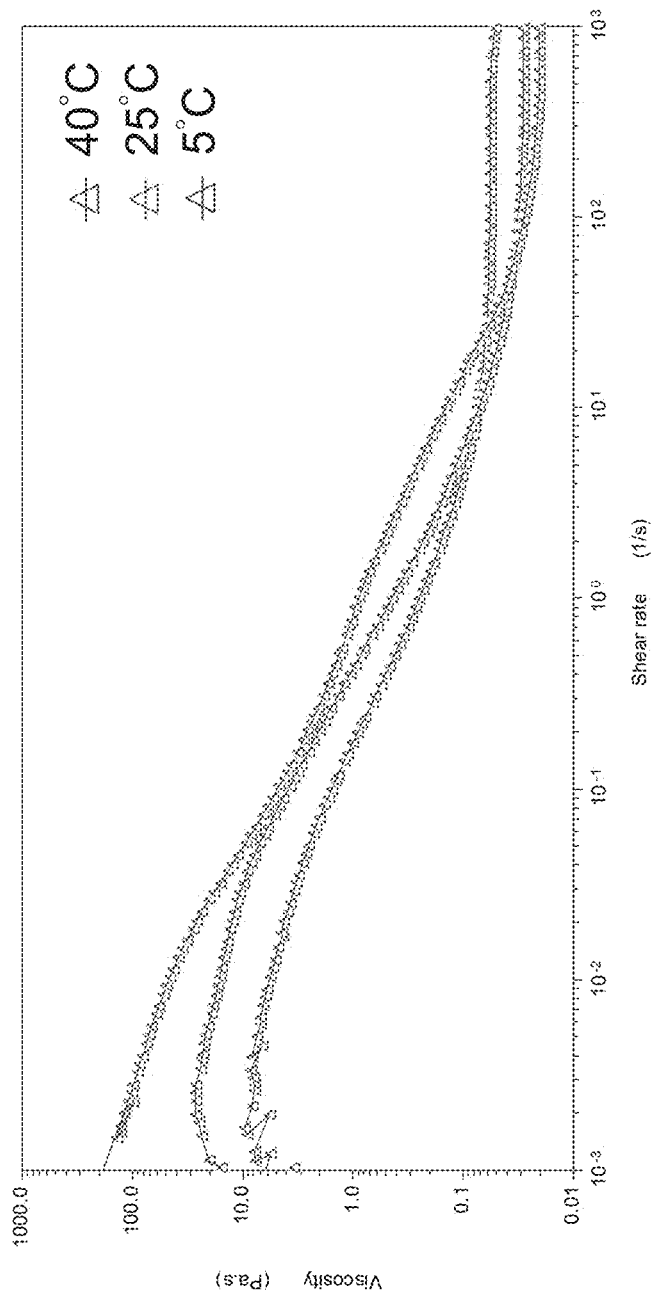

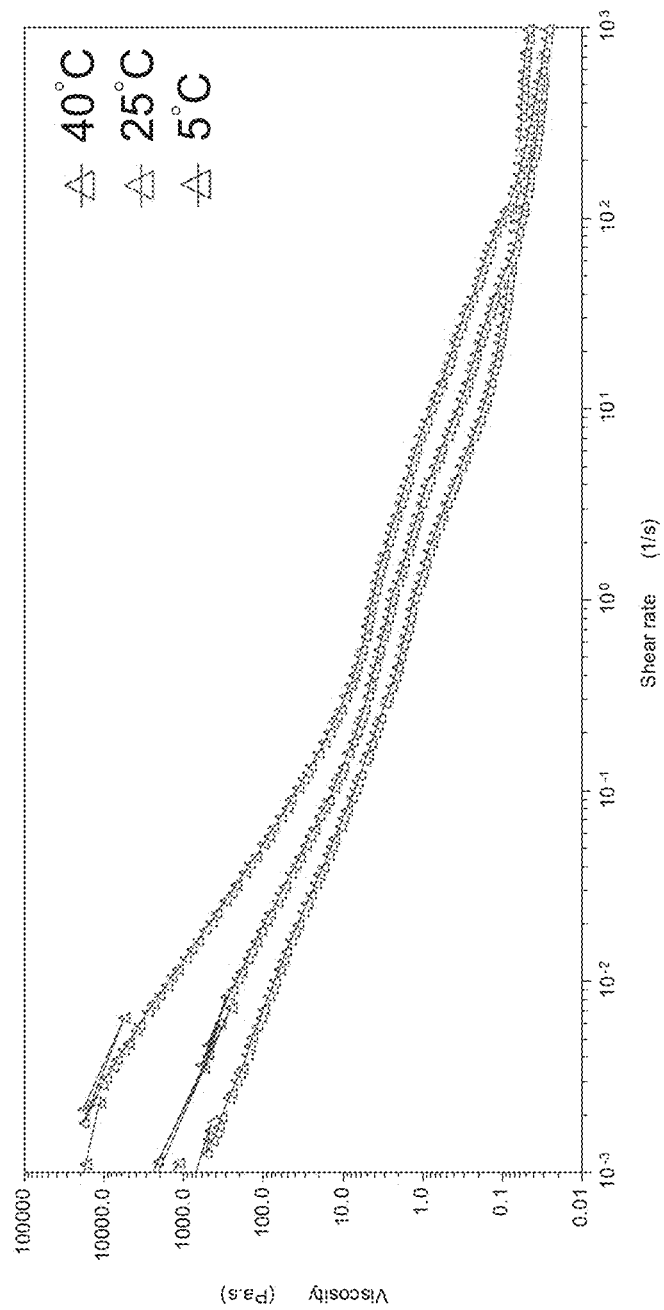
[Fig. 14]

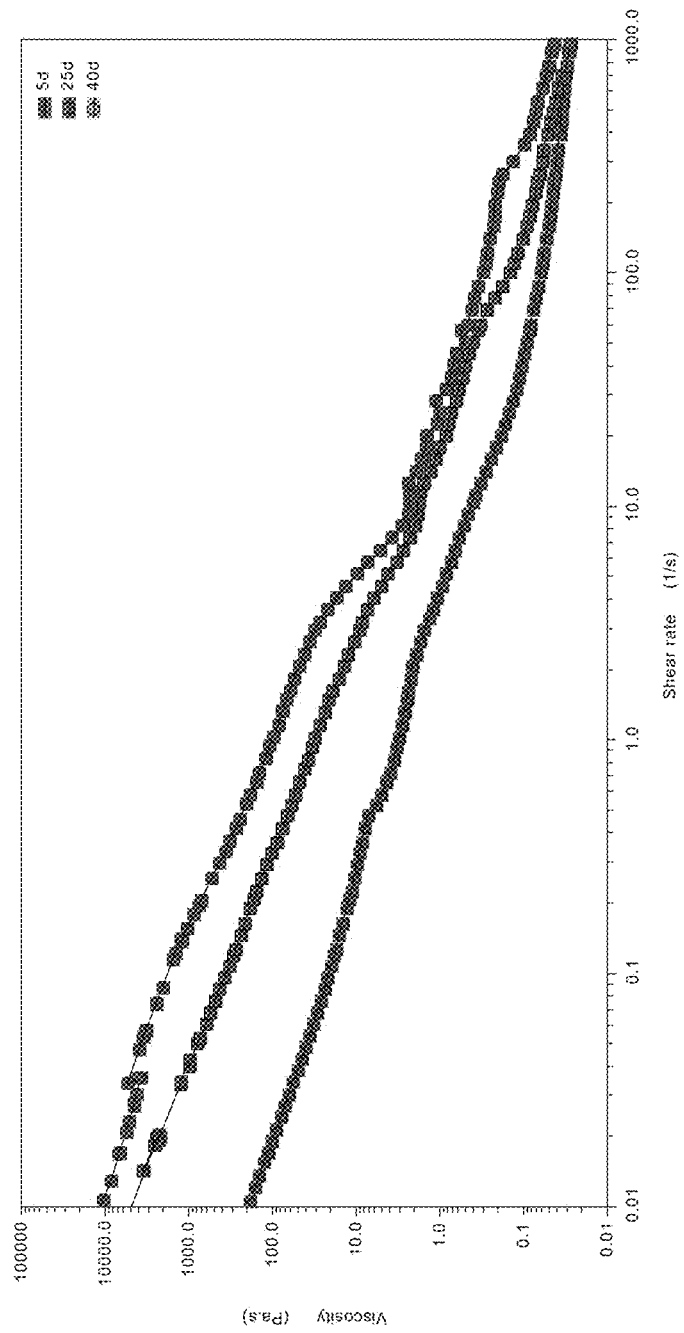
[Fig. 15]

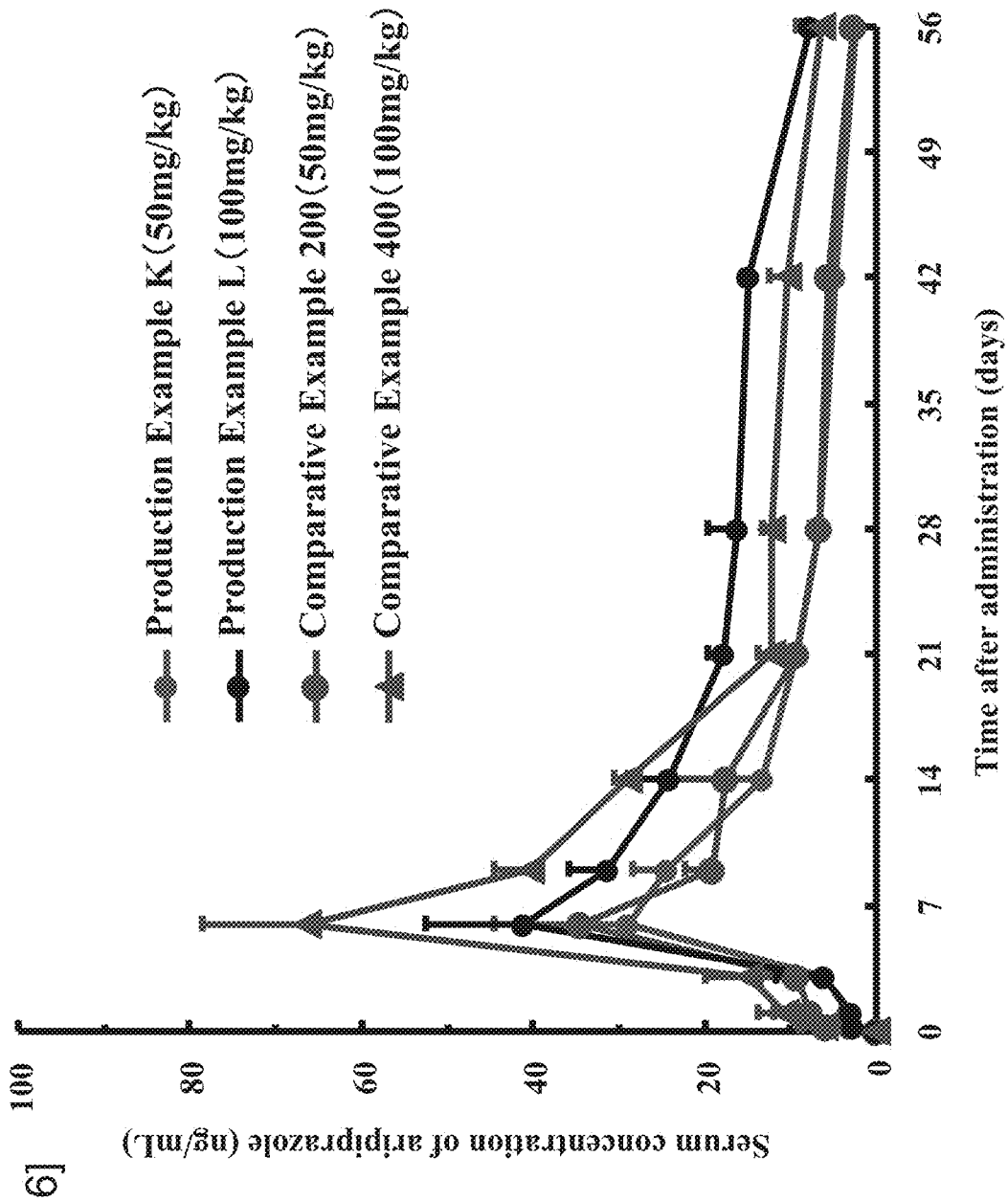
[Fig. 16]

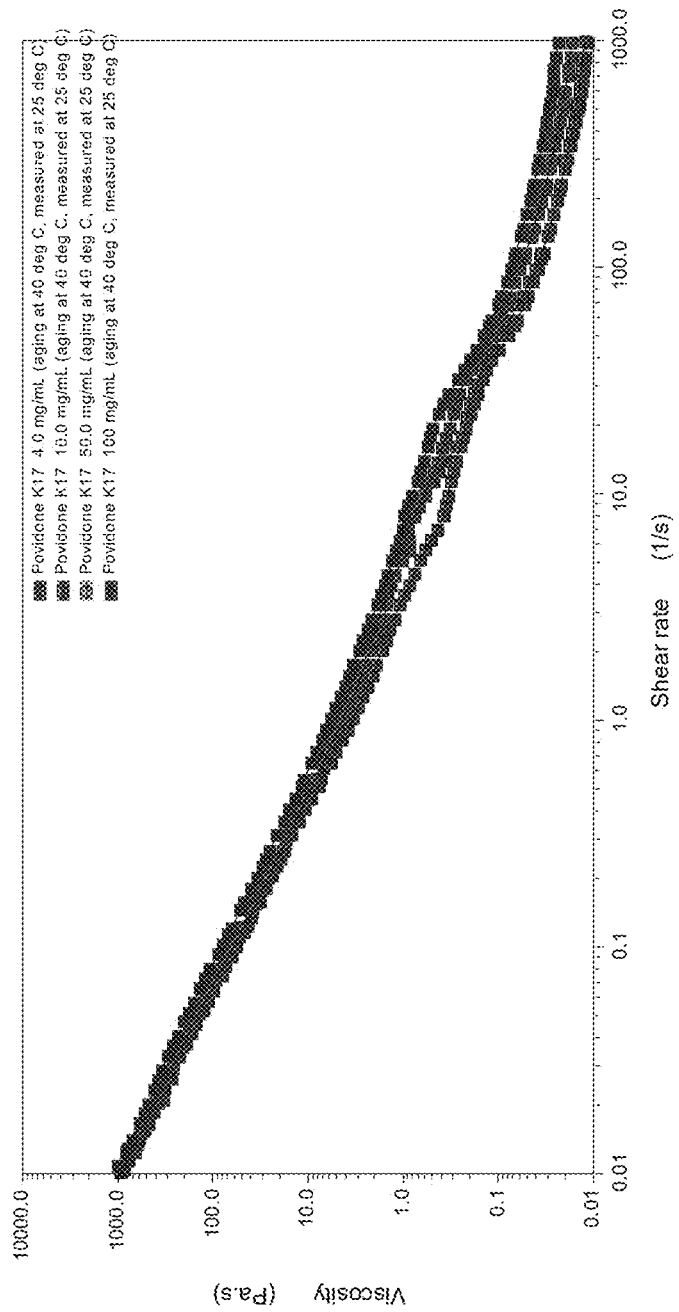
[Fig. 17]

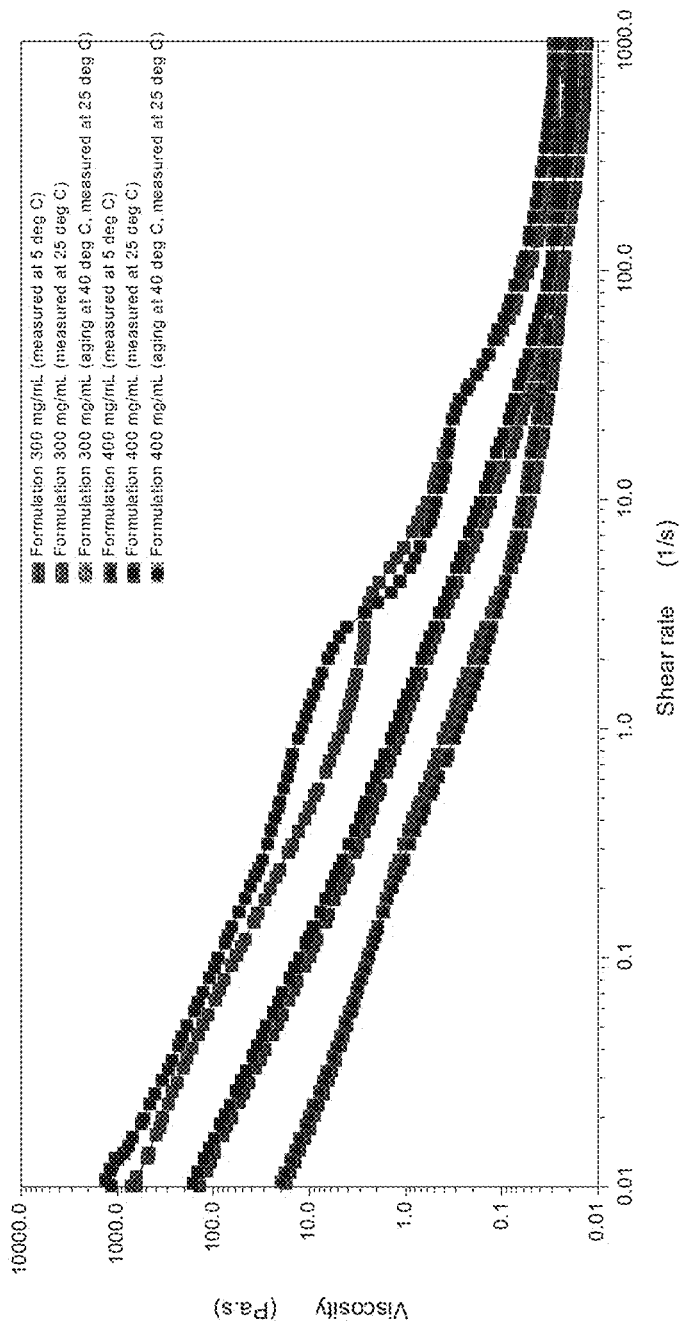
[Fig. 18]

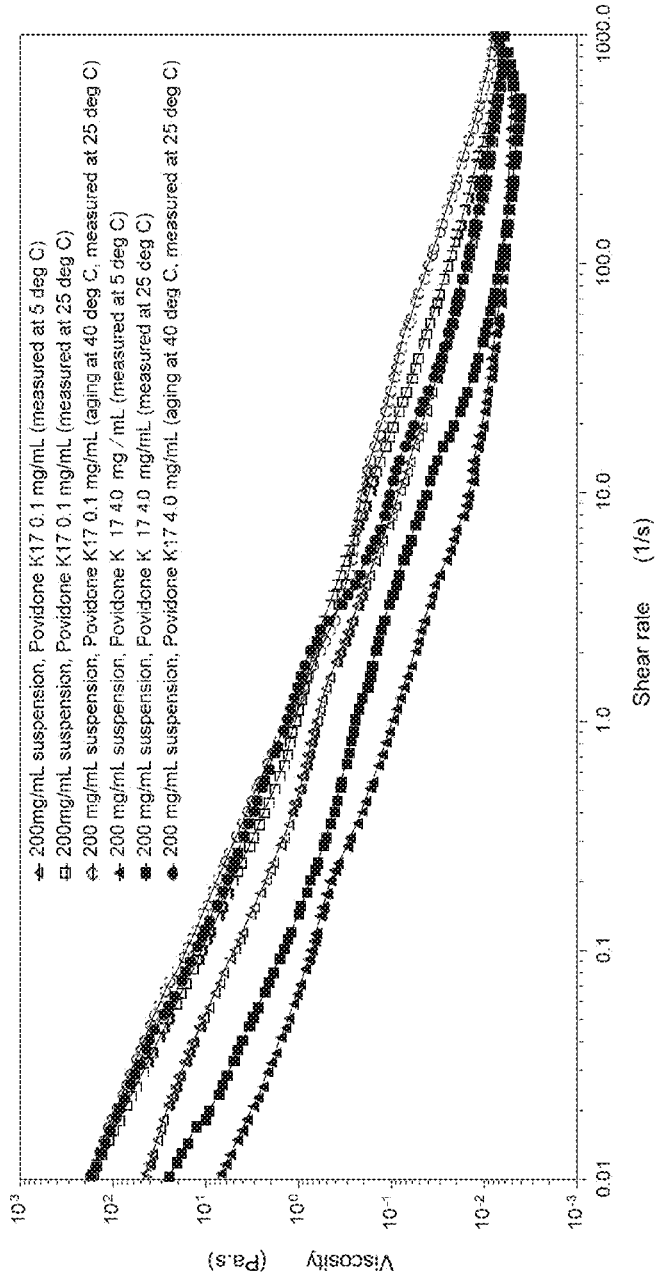
[Fig. 19a]
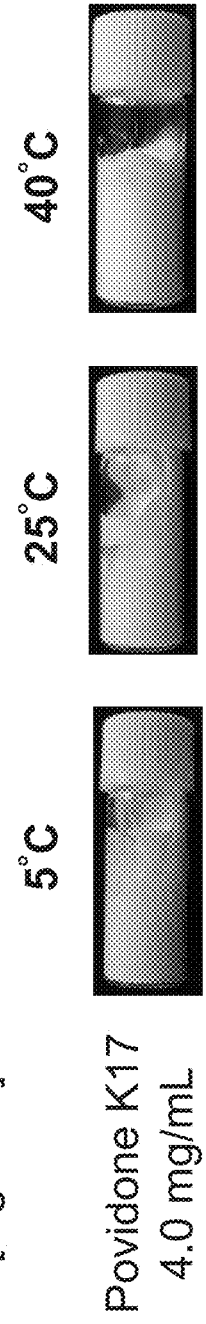
[Fig. 19b]
Povidone K17
4.0 mg/mL

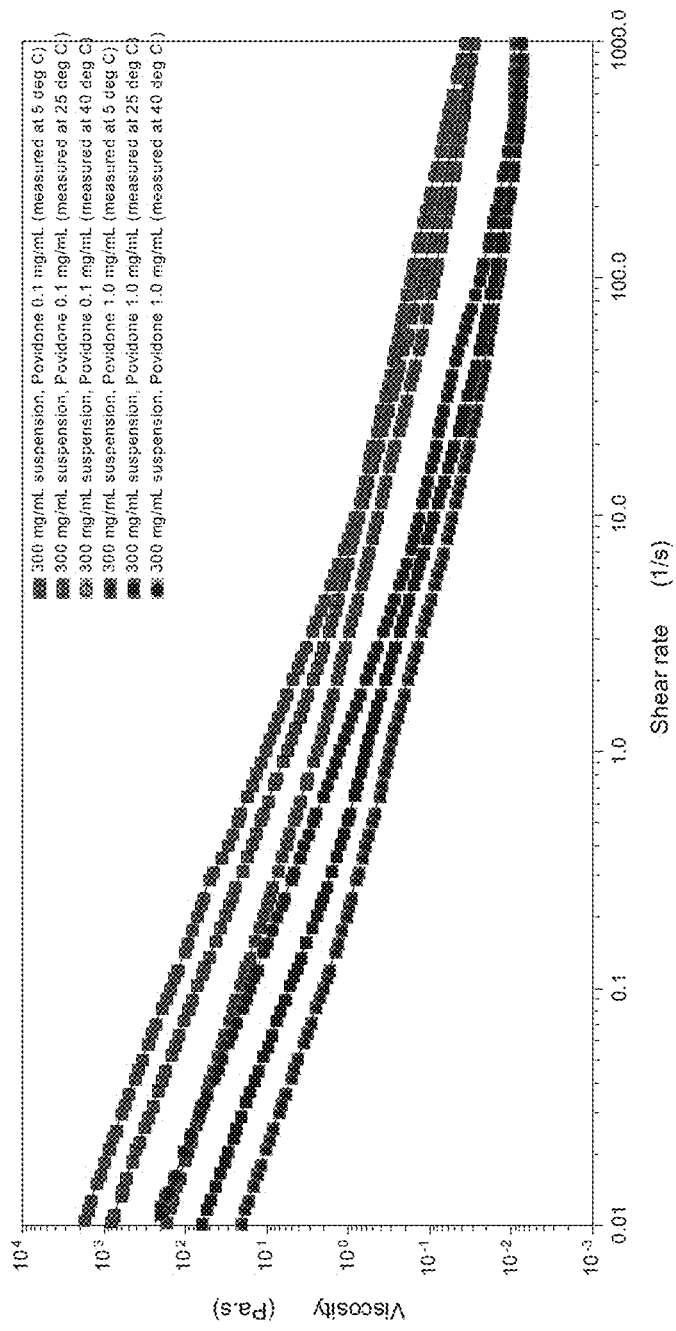
[Fig. 20a]

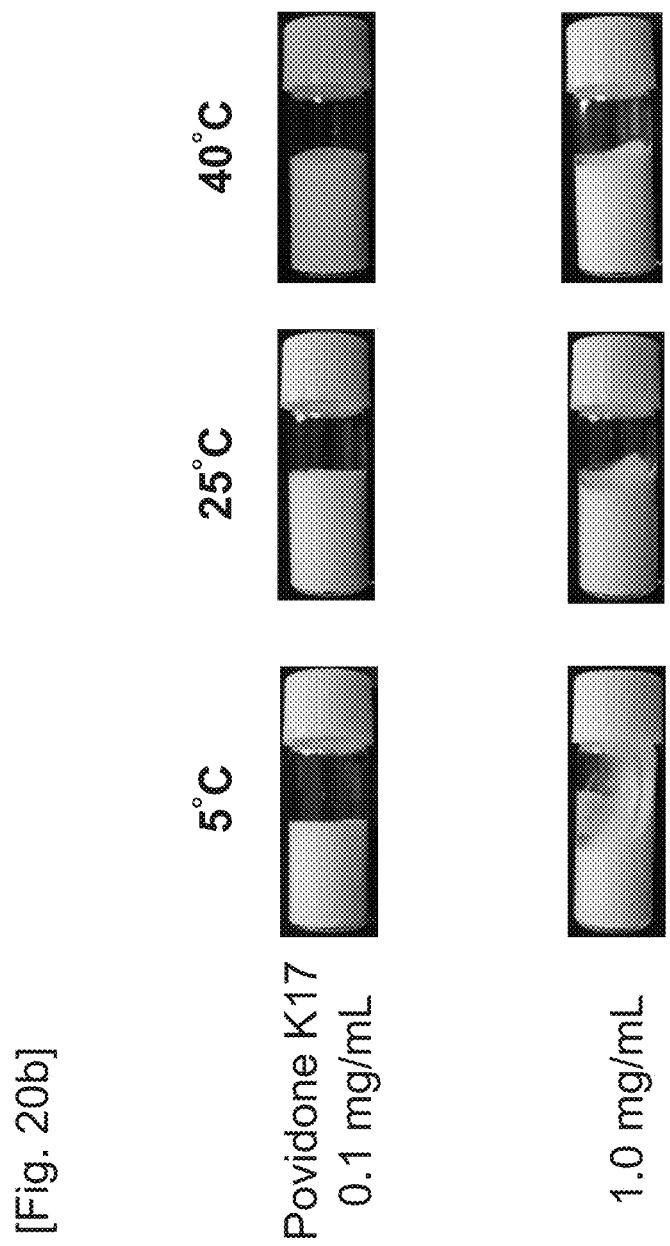
[Fig. 20b]

INJECTABLE PREPARATION

This is a continuation of application Ser. No. 16/785,268, filed Feb. 7, 2020, which is a continuation of application Ser. No. 16/514,973, filed Jul. 17, 2019, which is a continuation of application Ser. No. 16/156,958, filed Oct. 10, 2018, now U.S. Pat. No. 10,517,951, issued Dec. 31, 2019, which is a continuation of application Ser. No. 15/701,202, filed Sep. 11, 2017 (abandoned), which is a continuation of application Ser. No. 14/396,380, filed Oct. 22, 2014 (abandoned), which is the National Stage of PCT/JP2013/062683, filed Apr. 23, 2013, and claims benefit to Provisional Application No. 61/636,938, filed Apr. 23, 2012 and Provisional Application No. 61/792,089, filed Mar. 15, 2013, all of which are incorporated herein by reference.

TECHNICAL FIELD

The present invention relates to an injectable preparation comprising a composition comprising a drug that is poorly soluble in a dispersion medium, such as aripiprazole or a salt thereof, a specific suspending agent, and a dispersion medium, and to a prefilled syringe containing the injectable preparation.

BACKGROUND ART

Aripiprazole used as an active ingredient of a pharmaceutical composition is a compound represented by the following structural formula:

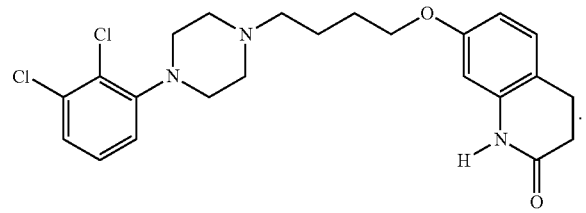 [SMILES: O=C1CCc2ccc(OCCCCN3CCN(c4cccc(Cl)c4Cl)CC3)cc2N1]

A pharmaceutical composition comprising aripiprazole is known as an atypical antipsychotic useful for the treatment of schizophrenia.

A pharmaceutical composition comprising aripiprazole as an active ingredient is known to be used, for example, in the following form. A cake-like composition, which is prepared by suspending aripiprazole and a vehicle therefor in a dispersion medium and freeze-drying the suspension, is mixed with a desired dispersant (preferably water for injection) before use and resuspended, and the resuspension (injectable preparation) is intramuscularly or subcutaneously injected into a patient (see, for example, Patent Literature 1 and 2).

The form of using the pharmaceutical composition as disclosed in Patent Literature (PTL) 1 and 2 requires a vial containing a cake-like composition, a container containing a dispersion medium, and a syringe for use at the time of administration to a patient. Accordingly, a pharmaceutical preparation that can simplify the structure of the medical instruments used and reduce size and weight and that is more convenient for use is desired.

CITATION LIST

Patent Literature

FPL 1: U.S. Pat. No. 5,006,528
PTL 2: JP2007-509148A

SUMMARY OF INVENTION

Technical Problem

To obtain such a pharmaceutical preparation that can simplify the structure of the medical instruments used and reduce size and weight and that is more convenient at the time of use, the development of, for example, a prefilled syringe produced by filling a suspension (injectable preparation) as is into a syringe can be considered. However, in the case of a suspension containing, as an active ingredient, a drug that is poorly soluble in water as a dispersion medium (hereinafter also referred to as a "poorly soluble drug"), such as aripiprazole or a salt thereof, particles of the active ingredient precipitate over time, which results in caking and makes it difficult to redisperse the suspension. Even if the suspension can be redispersed, the redispersion requires vigorous shaking, for example, by using a device or the like, which is clinically inconvenient. Therefore, a storage-stable injectable preparation that comprises a poorly soluble drug as an active ingredient and that is prevented from caking due to the precipitation of particles over time has been desired.

An object of the present invention is to provide a highly storage-stable injectable preparation comprising a composition comprising a poorly soluble drug as an active ingredient and a dispersion medium. More specifically, an object of the present invention is to provide an injectable preparation that can easily provide a suspension in which an active ingredient is well dispersed at the time of use (administration to a patient), without caking due to precipitation of a poorly soluble drug even after prolonged storage.

Another object of the present invention is to provide a more compact, lightweight prefilled syringe by filling a syringe with the above-mentioned injectable preparation. More preferably, an object of the present invention is to provide a more compact, lightweight prefilled syringe that allows administration of a suspension with low viscosity by simply pressing the plunger rod of the syringe to eject an injectable preparation through a syringe needle after gently shaking the syringe or without shaking.

Solution to Problem

To achieve the above objects, the present inventors conducted extensive research. As a result, the inventors found that when an injectable preparation comprising a poorly soluble drug as an active ingredient further comprises a dispersion medium and a specific suspending agent (hereinafter also referred to as suspending agent A), caking due to precipitation of the active ingredient is prevented even when stored for a long period of time after production (for example, until it is administered to a patient). The inventors conducted further research and accomplished the present invention.

The present invention includes the subject matter presented in the following items.

Item 1. An injectable preparation comprising a composition comprising a poorly soluble drug, a dispersion medium, and a suspending agent, the suspending agent being at least one member selected from the group consisting of (i) and (ii):
(i) polyvinylpyrrolidone, and
(ii) polyethylene glycol and carboxymethyl cellulose or a salt thereof,
the composition having a viscosity of 40 Pa·s or more in at least one point in the shear rate range of 0.01 to 0.02 $s^{-1}$ and having a viscosity of 0.2 Pa·s or less in at least one point in the shear rate range of 900 to 1,000 $s^{-1}$, as measured by a rheometer.

Item 2. An injectable preparation comprising a composition comprising a poorly soluble drug, a dispersion medium, and a suspending agent,
the suspending agent being at least one member selected from the group consisting of (i) and (ii):
(i) polyvinylpyrrolidone, and
(ii) polyethylene glycol and carboxymethyl cellulose or a salt thereof,
the composition having a viscosity of 40 Pa·s or more in at least one point in the shear rate range of 0.01 to 0.02 $s^{-1}$ and having a viscosity of 0.2 Pa·s or less in at least one point in the shear rate range of 900 to 1,000 $s^{-1}$, as measured by a rheometer at 25° C.

Item 3. The injectable preparation according to Item 1 or 2 comprising a composition comprising at least water as a dispersion medium.

Item 4. The injectable preparation according to any one of Items 1 to 3 wherein the poorly soluble drug is aripiprazole or a salt thereof, or 7-[4-(4-benzo[b]thiophen-4-yl-piperazin-1-yl)butoxy]-1H-quinolin-2-one or a salt thereof.

Item 4a. The injectable preparation according to any one of Items 1 to 4 wherein the poorly soluble drug has a mean primary particle diameter of 0.5 to 100 n.

Item 4b. The injectable preparation according to any one of Items 1 to 4 and 4a wherein the poorly soluble drug has a mean secondary particle diameter that is up to but not exceeding three times the mean primary particle diameter thereof.

Item 5. A gel composition comprising
a poorly soluble drug which is aripiprazole or a salt thereof, or 7-[4-(4-benzo[b]thiophen-4-yl-piperazin-1-yl)butoxy]-1H-quinolin-2-one or a salt thereof, water, and
at least one suspending agent selected from the group consisting of (i) and (ii):
(i) polyvinylpyrrolidone, and
(ii) polyethylene glycol and carboxymethyl cellulose or a salt thereof,
wherein the poorly soluble drug has a mean primary particle diameter of 0.5 to 30 μm and is contained in a concentration of 200 to 600 mg/mL.

Item 5a. The gel composition according to Item 5 comprising
aripiprazole or a salt thereof,
water, and
at least one suspending agent selected from the group consisting of (i) and (ii):
(i) polyvinylpyrrolidone, and
(ii) polyethylene glycol and carboxymethyl cellulose or a salt thereof,
wherein the aripiprazole or a salt thereof has a mean primary particle diameter of 0.5 to 30 μm and is contained in a concentration of 200 to 600 mg/mL.

Item 5b. The gel composition according to Item 5 comprising
7-[4-(4-benzo[b]thiophen-4-yl-piperazin-1-yl)butoxy]-1H-quinolin-2-one or a salt thereof,
water, and
at least one suspending agent selected from the group consisting of (i) and (ii):
(i) polyvinylpyrrolidone, and
(ii) polyethylene glycol and carboxymethyl cellulose or a salt thereof,
wherein the 7-[4-(4-benzo[b]thiophen-4-yl-piperazin-1-yl)butoxy]-1H-quinolin-2-one or a salt thereof has a mean primary particle diameter of 0.5 to 30 μm and is contained in a concentration of 200 to 600 mg/mL.

Item 6. The composition according to Item 5, 5a, or 5b wherein (i) polyvinylpyrrolidone is contained as a suspending agent in a concentration of 0.1 to 100 mg/mL.

Item 7. The composition according to any one of Items 5 to 6 wherein (ii) polyethylene glycol and carboxymethyl cellulose or a salt thereof are contained as suspending agents, the concentration of polyethylene glycol being 0.05 to 2 mg/mL, and the concentration of carboxymethyl cellulose or a salt thereof being 0.5 to 50 mg/mL.
(The above phrase "any one of Items 5 to" includes Items 5, 5a, and 5b. The same applies hereinafter.)

Item 8. The composition according to any one of Items 5 to 7 wherein (i) polyvinylpyrrolidone and (ii) polyethylene glycol and carboxymethyl cellulose or a salt thereof are contained as suspending agents.

Item 8a. The composition according to Items 5 or 6 wherein (i) polyvinylpyrrolidone and (ii) polyethylene glycol and carboxymethyl cellulose or a salt thereof are contained as suspending agents, the concentration of polyethylene glycol being 0.05 to 100 mg/mL.

Item 9. The composition according to any one of Items 5 to 8 and 8a wherein the poorly soluble drug has a mean secondary particle diameter that is up to but not exceeding three times the mean primary particle diameter thereof.

Item 10. The composition according to any one of Items 5 to 9 which has a viscosity of 40 Pa·s or more in at least one point in the shear rate range of 0.01 to 0.02 $s^{-1}$ and which has a viscosity of 0.2 Pa·s or less in at least one point in the shear rate range of 900 to 1,000 $s^{-1}$, as measured by a rheometer.

Item 11. The composition according to any one of Items 5 to 9 which has a viscosity of 40 Pa·s or more in at least one point in the shear rate range of 0.01 to 0.02 $s^{-1}$ and which has a viscosity of 0.2 Pa·s or less in at least one point in the shear rate range of 900 to 1,000 $s^{-1}$, as measured by a rheometer at 25° C.

Item 12. An injectable preparation comprising the composition according to any one of Item 5 to 11.

Item 13. A method for producing a gel composition comprising aripiprazole or a salt thereof, or 7-[4-(4-benzo[b]thiophen-4-yl-piperazin-1-yl)butoxy]-1H-quinolin-2-one or a salt thereof, the method comprising
allowing a liquid mixture to stand at 5 to 70° C. for 5 minutes or more, the liquid mixture comprising aripiprazole or a salt thereof, or 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):
(i) polyvinylpyrrolidone, and
(ii) polyethylene glycol and carboxymethyl cellulose or a salt thereof, and
the aripiprazole or a salt thereof, or the 7-[4-(4-benzo[b]thiophen-4-yl-piperazin-1-yl)butoxy]-1H-quinolin-2-one or a salt thereof having a mean primary particle diameter of 0.5 to 30 μm.

Item 13a. The method for producing a gel composition comprising aripiprazole or a salt thereof according to Item 13, the method comprising allowing a liquid mixture to stand at 5 to 70° C. for 5 minutes or more, the liquid mixture comprising aripiprazole or a salt thereof in a concentration of 200 to 600 mg/mL, water, and at least one suspending agent selected from the group consisting of (i) and (ii):
(i) polyvinylpyrrolidone, and
(ii) polyethylene glycol and carboxymethyl cellulose or a salt thereof, and
the aripiprazole or a salt thereof having a mean primary particle diameter of 0.5 to 30 μm.

Item 13b. The method for producing a gel composition comprising 7-[4-(4-benzo[b]thiophen-4-yl-piperazin-1-yl)butoxy]-1H-quinolin-2-one or a salt thereof according to Item 13, the method comprising allowing a liquid mixture to stand at 5 to 70° C. for 5 minutes or more, the liquid mixture comprising 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):
(i) polyvinylpyrrolidone, and
(ii) polyethylene glycol and carboxymethyl cellulose or a salt thereof, and
the 7-[4-(4-benzo[b]thiophen-4-yl-piperazin-1-yl)butoxy]-1H-quinolin-2-one or a salt thereof having a mean primary particle diameter of 0.5 to 30 μm.

Item 14. The method according to Item 13 comprising pulverizing aripiprazole or a salt thereof, or 7-[4-(4-benzo[b]thiophen-4-yl-piperazin-1-yl)butoxy]-1H-quinolin-2-one or a salt thereof to a mean primary particle diameter of 0.5 to 30 μm in a liquid mixture comprising the aripiprazole or a salt thereof, or the 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):
(i) polyvinylpyrrolidone, and
(ii) polyethylene glycol and carboxymethyl cellulose or a salt thereof,
and allowing the pulverized liquid mixture to stand at 5 to 70° C. for 5 minutes or more.

Item 14a. The method for producing a gel composition comprising aripiprazole or a salt thereof according to Item 14 comprising pulverizing aripiprazole or a salt thereof to a mean primary particle diameter of 0.5 to 30 μm in a liquid mixture comprising the aripiprazole or a salt thereof in a concentration of 200 to 600 mg/mL, water, and at least one suspending agent selected from the group consisting of (i) and (ii):
(i) polyvinylpyrrolidone, and
(ii) polyethylene glycol and carboxymethyl cellulose or a salt thereof,
and allowing the pulverized liquid mixture to stand at 5 to 70° C. for 5 minutes or more.

Item 14b. The method for producing a gel composition comprising 7-[4-(4-benzo[b]thiophen-4-yl-piperazin-1-yl)butoxy]-1H-quinolin-2-one or a salt thereof according to Item 14 comprising pulverizing 7-[4-(4-benzo[b]thiophen-4-yl-piperazin-1-yl)butoxy]-1H-quinolin-2-one or a salt thereof to a mean primary particle diameter of 0.5 to 30 μm in a liquid mixture comprising the 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):
(i) polyvinylpyrrolidone, and
(ii) polyethylene glycol and carboxymethyl cellulose or a salt thereof,
and allowing the pulverized liquid mixture to stand at 5 to 70° C. for 5 minutes or more.

Item 15. The method according to Item 13, 13a, 13b, 14, 14a, or 14b wherein the liquid mixture comprises (i) polyvinylpyrrolidone in a concentration of 0.1 to 100 mg/mL.

Item 16. The method according to Item 13, 13a, 13b, 14, 14a, 14b, or 15 wherein the liquid mixture comprises (ii) polyethylene glycol and carboxymethyl cellulose or a salt thereof, the concentration of polyethylene glycol being 0.05 to 2 mg/L, and the concentration of carboxymethyl cellulose or a salt thereof being 0.5 to 50 mg/mL.

Item 17. The method according to any one of items 13 to 16 wherein the liquid mixture comprises (i) polyvinylpyrrolidone and (ii) polyethylene glycol and carboxymethyl cellulose or a salt thereof.

Item 17a. The method according to any one of Items 13 to 15 wherein the liquid mixture comprises (i) polyvinylpyrrolidone and (ii) polyethylene glycol and carboxymethyl cellulose or a salt thereof,
the concentration of polyethylene glycol being 0.05 to 100 mg/mL. (The above phrases "Items 13 to 15" and "Items 13 to 16" include Items 13a, 13b, 14a, and 14b.)

Item 18. A gel composition comprising aripiprazole or a salt thereof, or 7-[4-(4-benzo[b]thiophen-4-yl-piperazin-1-yl)butoxy]-1H-quinolin-2-one or a salt thereof, the composition being obtained by the method according to any one of Items 13 to 17. (The above phrase "Items 13 to 17" also includes Items 13a, 13b, 14a, 14b and 17a.)

Item 19. A method for producing a prefilled syringe that is prefilled with a gel composition comprising aripiprazole or a salt thereof, or 7-[4-(4-benzo[b]thiophen-4-yl-piperazin-1-yl)butoxy]-1H-quinolin-2-one or a salt thereof, the method comprising:

filling into a syringe a liquid mixture comprising aripiprazole or a salt thereof, or 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):
(i) polyvinylpyrrolidone, and
(ii) polyethylene glycol and carboxyethyl cellulose or a salt thereof,
wherein the aripiprazole or a salt thereof, or the 7-[4-(4-benzo[b]thiophen-4-yl-piperazin-1-yl)butoxy]-1H-quinolin-2-one or a salt thereof has a mean primary particle diameter of 0.5 to 30 μm; and
allowing the liquid mixture to stand at 5 to 70° C. for 5 minutes or more.

Item 19a. The method for producing a prefilled syringe that is prefilled with a gel composition comprising aripiprazole or a salt thereof according to Item 19, the method comprising:

filling into a syringe a liquid mixture comprising aripiprazole or a salt thereof in a concentration of 200 to 600 mg/mL, water, and at least one suspending agent selected from the group consisting of (i) and (ii):
(i) polyvinylpyrrolidone, and
(ii) polyethylene glycol and carboxymethyl cellulose or a salt thereof,
wherein the aripiprazole or a salt thereof has a mean primary particle diameter of 0.5 to 30 μm; and
allowing the liquid mixture to stand at 5 to 70° C. for 5 minutes or more.

Item 19b. The method for producing a prefilled syringe that is prefilled with a gel composition comprising 7-[4-(4-benzo[b]thiophen-4-yl-piperazin-1-yl)butoxy]-1H-quinolin-2-one or a salt thereof according to Item 19, the method comprising:

filling into a syringe a liquid mixture comprising 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):

(i) polyvinylpyrrolidone, and (ii) polyethylene glycol and carboxymethyl cellulose or a salt thereof, wherein the 7-[4-(4-benzo[b]thiophen-4-yl-piperazin-1-yl)butoxy]-1H-quinolin-2-one or a salt thereof has a mean primary particle diameter of 0.5 to 30 μm; and allowing the liquid mixture to stand at 5 to 70° C. for 5 minutes or more.

Item 20. The method according to Item 19 comprising:

pulverizing aripiprazole or a salt thereof, or 7-[4-(4-benzo[b]thiophen-4-yl-piperazin-1-yl)butoxy]-1H-quinolin-2-one or a salt thereof to a mean primary particle diameter of 0.5 to 30 μM in a liquid mixture comprising the aripiprazole or a salt thereof, or the 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):

(i) polyvinylpyrrolidone, and (ii) polyethylene glycol and carboxymethyl cellulose or a salt thereof; and filling the pulverized liquid mixture into a syringe and allowing the pulverized liquid mixture to stand at 5 to 70° C. for 5 minutes or more.

Item 20a. The method for producing a prefilled syringe that is prefilled with a gel composition comprising aripiprazole or a salt thereof according to Item 20, the method comprising:

pulverizing aripiprazole or a salt thereof to a mean primary particle diameter of 0.5 to 30 μm in a liquid mixture comprising the aripiprazole or a salt thereof in a concentration of 200 to 600 mg/mL, water, and at least one suspending agent selected from the group consisting of (i) and (ii):

(i) polyvinylpyrrolidone, and (ii) polyethylene glycol and carboxymethyl cellulose or a salt thereof; and filling the pulverized liquid mixture into a syringe and allowing the pulverized liquid mixture to stand at 5 to 70° C. for 5 minutes or more.

Item 20b. The method for producing a prefilled syringe that is prefilled with a gel composition comprising 7-[4-(4-benzo[b]thiophen-4-yl-piperazin-1-yl)butoxy]-1H-quinolin-2-one or a salt thereof according to Item 20, the method comprising:

pulverizing 7-[4-(4-benzo[b]thiophen-4-yl-piperazin-1-yl)butoxy]-1H-quinolin-2-one or a salt thereof to a mean primary particle diameter of 0.5 to 30 μm in a liquid mixture comprising the 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):

(i) polyvinylpyrrolidone, and (ii) polyethylene glycol and carboxymethyl cellulose or a salt thereof; and filling the pulverized liquid mixture into a syringe and allowing the pulverized liquid mixture to stand at 5 to 70° C. for 5 minutes or more.

Item 21. The method according to Item 19, 19a, 19b, 20, 20a, or 20b wherein the liquid mixture comprises (i) polyvinylpyrrolidone, the concentration of (i) polyvinylpyrrolidone being 0.1 to 100 mg/mL.

Item 22. The method according to any one of Items 19 to 21 wherein the liquid mixture comprises (ii) polyethylene glycol and carboxymethyl cellulose or a salt thereof, the concentration of polyethylene glycol being 0.05 to 2 g/mL, and the concentration of carboxymethyl cellulose or a salt thereof being 0.5 to 50 mg/mL.

Item 23. The method according to any one of Items 19 to 22 wherein the liquid mixture comprises (i) polyvinylpyrrolidone and (ii) polyethylene glycol and carboxymethyl cellulose or a salt thereof.

Item 23a. The method according to any one of Items 19 to 21 wherein the liquid mixture comprises (i) polyvinylpyrrolidone and (ii) polyethylene glycol and carboxymethyl cellulose or a salt thereof, the concentration of polyethylene glycol being 0.05 to 100 mg/mL.

(The above phrases "Items 19 to 21" and "Items 19 to 22" also include Items 19a, 19b, 20a, and 20b.)

Item 24. A prefilled syringe that is prefilled with a gel composition comprising aripiprazole or a salt thereof, or 7-[4-(4-benzo[b]thiophen-4-yl-piperazin-1-yl)butoxy]-1H-quinolin-2-one or a salt thereof, the syringe being obtained by the method according to any one of Items 19 to 23 and 23a.

Item 25. A kit comprising the prefilled syringe according to Item 24.

Item 26. A sustained release injectable preparation comprising a composition comprising a poorly soluble drug which is aripiprazole or a salt thereof, or 7-[4-(4-benzo[b]thiophen-4-yl-piperazin-1-yl)butoxy]-1H-quinolin-2-one or a salt thereof, water, and at least one suspending agent selected from the group consisting of (i) and (ii):

(i) polyvinylpyrrolidone, and (ii) polyethylene glycol and carboxymethyl cellulose or a salt thereof, wherein the poorly soluble drug has a mean primary particle diameter of 1 to 10 μm and is contained in a concentration of 200 to 400 mg/mL, the composition being in the form of a gel when allowed to stand, and changing to a sol when subjected to an impact, and the preparation being administered once per month.

Item 27. The injectable preparation according to Item 26 wherein the poorly soluble drug has a mean primary particle diameter of 2 to 7 μm.

Item 28. A sustained release injectable preparation comprising a composition comprising a poorly soluble drug which is aripiprazole or a salt thereof, or 7-[4-(4-benzo[b]thiophen-4-yl-piperazin-1-yl)butoxy]-1H-quinolin-2-one or a salt thereof, water, and at least one suspending agent selected from the group consisting of (i) and (ii):

(i) polyvinylpyrrolidone, and (ii) polyethylene glycol and carboxymethyl cellulose or a salt thereof, wherein the poorly soluble drug has a mean primary particle diameter of 4 to 30 μm and is contained in a concentration of 300 to 600 mg/mL, the composition being in the form of a gel when allowed to stand, and changing to a sol when subjected to an impact, and the preparation being administered once every two or three months.

Item 29. The injectable preparation according to Item 28 wherein the poorly soluble drug has a mean primary particle diameter of 5 to 20 μm.

Item 30. The injectable preparation according to any one of Items 26 to 29 wherein (i) polyvinylpyrrolidone is contained as a suspending agent in a concentration of 0.1 to 100 mg/mL.

Item 31. The injectable preparation according to any one of Items 26 to 30 wherein (ii) polyethylene glycol and carboxymethyl cellulose or a salt thereof are contained as suspending agents, the concentration of polyethylene glycol being 0.05 to 2 mg/mL, and the concentration of carboxymethyl cellulose or a salt thereof being 0.5 to 50 mg/mL.

Item 32. The injectable preparation according to any one of Items 26 to 31 wherein (i) polyvinylpyrrolidone and (ii) polyethylene glycol and carboxymethyl cellulose or a salt thereof are contained as suspending agents.

Item 33. The injectable preparation according to any one of Items 26 to 32 wherein the poorly soluble drug has a mean secondary particle diameter that is up to but not exceeding three times the mean primary particle diameter thereof.

Item 34. The injectable preparation according to any one of Items 26 to 33 wherein the composition has a viscosity of 40 Pa·s or more in at least one point in the shear rate range of 0.01 to 0.02 s$^{-1}$ and a viscosity of 0.2 Pa·s or less in at least one point in the shear rate range of 900 to 1,000 s$^{-1}$, as measured by a rheometer.

Item 35. The injectable preparation according to any one of Items 26 to 33 wherein the composition has a viscosity of 40 Pa·s or more in at least one point in the shear rate range of 0.01 to 0.02 s$^{-1}$ and a viscosity of 0.2 Pa·s or less in at least one point in the shear rate range of 900 to 1,000 s$^{-1}$, as measured by a rheometer at 25° C.

Item 36. A method for treating or preventing a recurrence of schizophrenia, bipolar disorder, or depression, the method comprising administering the injectable preparation according to any one of Items 1 to 4, 12, and 26 to 35.

Item 37. The method according to Item 36 wherein the injectable preparation is administered intramuscularly or subcutaneously.

Item A-1. A storage-stable aqueous suspending injectable preparation comprising a poorly soluble drug, a specific suspending agent (suspending agent A), and a dispersion medium; the suspension having a high viscosity upon standing and a low viscosity upon shaking or ejection thereof through a syringe needle.

Item A-2. The injectable preparation according to Item A-1, which has a viscosity of 1,000 mPa·s or more upon standing and a viscosity of 300 mPa·s or less upon shaking or ejection thereof through a syringe needle.

Item A-3. The injectable preparation according to Item A-1 or A-2, which has a viscosity of 5,000 mPa·s or more upon standing and a viscosity of 300 mPa·s or less upon shaking or ejection thereof through a syringe needle.

Item A-4. The injectable preparation according to any one of Items A-1 to A-3, which has a viscosity of 10,000 mPa·s or more upon standing and a viscosity of 300 mPa·s or less upon shaking or ejection thereof through a syringe needle.

Item A-5. The injectable preparation according to Item A-1 or A-2, which has a viscosity of 1,000 mPa·s or more upon standing and a viscosity of 200 mPa·s or less upon shaking or ejection thereof through a syringe needle.

Item A-6. The injectable preparation according to Item A-1, A-2, A-3, or A-5, which has a viscosity of 5,000 mPa·s or more upon standing and a viscosity of 200 mPa·s or less upon shaking or ejection thereof through a syringe needle.

Item A-7. The injectable preparation according to any one of Items A-1 to A-6, which has a viscosity of 10,000 mPa·s or more upon standing and a viscosity of 200 mPa·s or less upon shaking or ejection thereof through a syringe needle.

Item A-8. The injectable preparation according to any one of Items A-1 to A-7, which contains the poorly soluble drug in a concentration of 100 to 500 mg/mL.

Item A-9. The injectable preparation according to any one of Items A-1 to A-8, which contains the poorly soluble drug in a concentration of 200 to 480 mg/mL.

Item A-10. The injectable preparation according to any one of Items A-1 to A-9, which contains the poorly soluble drug in a concentration of 250 to 450 mg/mL.

Item A-11. The injectable preparation according to any one of Items A-1 to A-10, which contains the poorly soluble drug in a concentration of about 300 mg/mL or more and becomes a gel upon standing, the gel composition becoming a fluid sol upon stirring, shaking, external shock, or the like.

Item A-12. The injectable preparation according to any one of Items A-1 to A-11, wherein the poorly soluble drug has a mean primary particle diameter of about 0.5 to 30 μm.

Item A-13. The injectable preparation according to any one of Items A-1 to A-12, wherein the poorly soluble drug has a mean primary particle diameter of about 1.0 to 10 μm.

Item A-14. The injectable preparation according to any one of Items A-1 to A-13, wherein the poorly soluble drug has a mean primary particle diameter of about 1.0 to 5 μm.

Item A-15. The injectable preparation according to any one of Items A-1 to A-14, wherein the poorly soluble drug is aripiprazole or a salt thereof, the preparation comprising a composition comprising a dispersion medium and at least one suspending agent selected from the group consisting of polyvinylpyrrolidone and polyethylene glycol.

Item A-16. The injectable preparation according to Item A-15, wherein the poorly soluble drug is aripiprazole monohydrate.

Item A-17. The injectable preparation according to Item A-15 or A-16, wherein the poorly soluble drug is aripiprazole or a salt thereof, the preparation being storage-stable and comprising a composition comprising sodium carboxymethyl cellulose, a dispersion medium, and at least one suspending agent selected from the group consisting of polyvinylpyrrolidone and polyethylene glycol.

Item A-18. A prefilled syringe comprising the injectable preparation according to any one of Items A-1 to A-17.

The expression "to comprise" used herein also includes the meanings of "to essentially consist of" and "to consist of."

ADVANTAGEOUS EFFECTS OF INVENTION

The injectable preparation of the present invention has excellent storage stability with no caking caused by precipitation of the particles of a poorly soluble drug (i.e., active ingredient).

Therefore, it is unnecessary to prepare a suspension at the time of use, and syringe needle clogging is less likely to occur.

More specifically, because (α) the injectable preparation of the present invention becomes a gel upon standing, precipitation and caking of the particles of the poorly soluble drug can be inhibited, thereby providing excellent storage stability. Furthermore, because (β) the injectable preparation of the present invention even in the form of a gel can easily gain fluidity when subjected to a mild impact, the preparation can be easily injected at the time of use (at the time of injection). In particular, because the gelled injectable preparation (gel composition) gains fluidity (forms a sol state) by simply pressing the plunger of a syringe and ejecting the preparation through a syringe needle, the preparation can be smoothly ejected through the needle as is. Therefore, the preparation can be well dispersed intramuscularly or subcutaneously with relatively less local disturbance and pain at the time of injection.

As described above, the injectable preparation of the present invention has excellent storage stability. This allows the injectable preparation to be filled as is into a syringe to prepare a prefilled syringe, thus providing a medical instrument with reduced size and weight.

BRIEF DESCRIPTION OF DRAWINGS

FIG. 1 shows a photograph of the injectable preparation obtained in Example 1 immediately after production.

FIG. 2 shows a photograph of the injectable preparation obtained in Example 1, which was slowly tilted after standing for a certain period.

FIG. 3 shows a photograph of the injectable preparation obtained in Example 1 having stood for a certain period, after which the container was tapped and tilted.

FIG. 4a shows photographs of the injectable preparations of Production Examples A1 to A6 each stored in a transparent container and allowed to stand at 5° C. for five days, after which the container was slowly tilted and laid horizontally.

FIG. 4b shows photographs of the injectable preparations of Production Examples A1 to A6 each stored in a transparent container and allowed to stand at 25° C. for five days, after which the container was slowly tilted and laid horizontally.

FIG. 4c shows photographs of the injectable preparations of Production Examples A1 to A6 each stored in a transparent container and allowed to stand at 40° C. for five days, after which the container was slowly tilted and laid horizontally.

FIG. 5a shows the viscosities of the injectable preparations of Production Examples A1 to A6 measured using a rheometer (measuring temperature: 5° C.).

FIG. 5b shows the viscosities of the injectable preparations of Production Examples A1 to A6 measured using a rheometer (measuring temperature: 25° C.).

FIG. 5c shows the viscosities of the injectable preparations of Production Examples A1 to A6 measured using a rheometer (measuring temperature: 40° C.).

FIG. 6 shows the viscosities of the injectable preparation of Production Example B measured using a rheometer at 5° C., 25° C., or 40° C.

FIG. 7 shows the viscosities of the injectable preparation of Production Example measured using a rheometer at 5° C., 25° C., or 40° C.

FIG. 8 shows the viscosities of the injectable preparation of Production Example D measured using a rheometer at 5° C., 25° C., or 40° C.

FIG. 9a shows the viscosities of the injectable preparation of Production Example E measured using a rheometer at 5° C., 25° C., or 40° C. In the Figure, 5d, 25d and 40d respectively indicate the measuring temperatures at 5° C., 25° C., and 40° C.

FIG. 9b shows the injectable preparation of Production Example E stored in a still condition at 5° C., 25° C., or 40° C. for five days.

FIG. 9c shows the injectable preparation of Production Example E stored in a still condition at 5° C., 25° C., or 40° C. for five days (i.e., each shown in FIG. 9b), after which the container was slowly tilted and laid horizontally.

FIG. 10a shows the viscosities of the injectable preparations of Production Example F1 (Povidone K17, 0.1 mg/mL) and Production Example F2 (Povidone K17, 4 mg/mL) measured using a rheometer at 5° C. or 25° C. In the Figure, 5d and 25d indicate the measuring temperatures at 5° C. and 25° C., respectively.

FIG. 10b shows the injectable preparations of Production Example F1 (Povidone K17, 0.1 mg/mL) and Production Example F2 (Povidone K17, 4 mg/mL) stored in a still condition at 5° C., 25° C., or 40° C. for five days.

FIG. 10c shows the injectable preparations of Production Example F1 (Povidone K17, 0.1 mg/mL) and Production Example F2 (Povidone K17, 4 mg/mL) stored in a still condition at 5° C., 25° C., or 40° C. for five days (i.e., each shown in FIG. 10b), after which the container was slowly tilted and laid horizontally.

FIG. 11 shows the injectable preparations of Production Example G (containing 400 mg/mL of ethyl 4-aminobenzoate), Production Example H (containing 300 mg/mL of probucol) and Production Example I (containing 300 mg/mL of cilostazol) each stored in a transparent container and allowed to stand at 5° C., 25° C., or 40° C. for five days, after which the container was slowly tilted and laid horizontally.

FIG. 12 shows the viscosities of the injectable preparation of Production Example G measured using a rheometer at 5° C., 25° C., or 40° C.

FIG. 13 shows the viscosities of the injectable preparation of Production Example H measured using a rheometer at 5° C., 25° C., or 40° C.

FIG. 14 shows the viscosities of the injectable preparation of Production Example I measured using a rheometer at 5° C., 25° C., or 40° C.

FIG. 15 shows the viscosities of the injectable preparation of Production Example J measured using a rheometer at 5° C., 25° C., or 40° C. In the Figure, 5d, 25d and 40d indicate the measuring temperatures at 5° C., 25° C., and 40° C., respectively.

FIG. 16 is a graph showing the mean serum concentration-time profiles after administration of injectable preparations of Production Example K, Production Example L, Comparative Example 200, and Comparative Example 400 to the crural muscle of rats (n=4, mean±standard deviation).

FIG. 17 shows the viscosities of the injectable preparations of Production Examples A3 to A6 measured after being allowed to stand at 40° C. for five minutes in a rheometer and returned to 25° C.

FIG. 18 shows the viscosities of the injectable preparations of Production Examples B and C measured after being allowed to stand at 40° C. for five minutes in a rheometer and returned to 25° C. FIG. 18 also shows the viscosities measured in Test Example 2 at 5° C. or 25° C.

FIG. 19a shows the viscosities of the injectable preparations of Production Example E and Production Example E' measured after being allowed to stand at 40° C. for five minutes in a rheometer and returned to 25° C. FIG. 19a also shows the viscosities of the injectable preparation of Production Example E' measured at 5° C. or 25° C. in the same manner as in Test Example 3. FIG. 19a further shows the viscosities of the injectable preparation of Production Example E measured at 5° C. or 25° C. in Test Example 3.

FIG. 19b shows the injectable preparation of Production Example E' (Povidone K17, 4 mg/mL) stored in a still condition at 5° C., 25° C., or 40° C. for five days, after which the container was slowly tilted and laid horizontally. Only the injectable preparation stored at 40° C. gelled.

FIG. 20a shows the viscosities of the injectable preparations of Production Example M1 and Production Example M2 measured using a rheometer at 5° C., 25° C., or 40° C.

FIG. 20b shows the injectable preparations of Production Example M1 and Production Example M2 stored in a still condition at 5° C., 25° C., or 40° C. for five days, after which the container was slowly tilted and laid horizontally.

DESCRIPTION OF EMBODIMENTS

The injectable preparation of the present invention comprises a composition comprising a poorly soluble drug, a specific suspending agent (suspending agent (A)), and a dispersion medium. Therefore, hereinafter, an explanation regarding the injectable preparation of the present invention is equivalent to an explanation regarding the composition. For example, when it is explained that the injectable preparation of the present invention comprises a certain component, it means that the injectable preparation of the present invention comprises a specific composition that comprises a specific component. The "poorly soluble drug" as used herein refers to a drug that is poorly soluble in water, and corresponds to "very slightly soluble" or "hardly soluble" drugs according to The Japanese Pharmacopoeia Sixteenth Edition. Specifically, after a drug is placed in water (a drug, if in the form of a solid, is pulverized and then placed in water) and vigorously shaken at 20±5° C. for 30 seconds, the degree of dissolution within 30 minutes is investigated. When not less than 1,000 mL and less than 10,000 mL of water is required to dissolve 1 g or 1 mL of a drug, the drug is "very slightly soluble". When 10,000 mL or more of water is required, the drug is "hardly soluble."

The poorly soluble drug contained in the injectable preparation of the present invention includes, for example, aripiprazole or a salt thereof. Other examples of poorly soluble drugs include 7-[4-(4-benzo[b]thiophen-4-yl-piperazin-1-ylbutoxy]-1H-quinolin-2-one (hereinafter also referred to as "brexpiprazole") or a salt thereof. Other examples thereof include rebamipide, cilostazol, probucol, ethyl 4-aminobenzoate, and the like. Such compounds may be in the form of a salt. Aripiprazole or a salt thereof, or 7-[4-(4-benzo[b]thiophen-4-yl-piperazin-1-yl)butoxy]-1H-quinolin-2-one or a salt thereof are particularly preferable.

When the poorly soluble drug is in the form of a salt, the salt is not particularly limited insofar as it is a pharmaceutically acceptable salt. Examples thereof include alkali metal salts (e.g., sodium salts and potassium salts); alkaline earth metal salts (e.g., calcium salts and magnesium salts), and like metal salts; ammonium salts; alkali metal carbonates (e.g., lithium carbonate, potassium carbonate, sodium carbonate, and cesium carbonate); alkali metal hydrogen carbonates (e.g., lithium hydrogen carbonate, sodium hydrogen carbonate, potassium hydrogen carbonate); alkali metal hydroxides (e.g., lithium hydroxide, sodium hydroxide, potassium hydroxide, and cesium hydroxide), and like salts of inorganic bases; tri(lower)alkylamines (e.g., trimethylamine, triethylamine, and N-ethyldiisopropylamine), pyridine, quinoline, piperidine, imidazole, picoline, dimethylaminopyridine, dimethylaniline, N-(lower)alkyl-morpholines (e.g., N-methylmorpholine), 1,5-diazabicyclo[4.3.0]nonene-5 (DBN), 1,8-diazabicyclo[5.4.0]undecene-7 (DBU), 1,4-diazabicyclo[2.2.2]octane (DABCO), and like salts of organic bases; hydrochloride, hydrobromate, hydroiodide, sulfate, nitrate, phosphate, and like salts of inorganic acids; formate, acetate, propionate, oxalate, malonate, succinate, fumarate, maleate, lactate, malate, citrate, tartrate, carbonate, picrate, methanesulfonate, ethanesulfonate, p-toluenesulfonate, glutamate, pamoate, and like salts of organic acids. The term "(lower) alkyl" as used herein refers to an "alkyl having 1 to 6 carbon atoms."

When the poorly soluble drug contained in the injectable preparation of the present invention is aripiprazole or a salt thereof, the crystalline form of aripiprazole or a salt thereof is not particularly limited. Aripiprazole or a salt thereof may be in a monohydrate form (aripiprazole hydrate A) or in various anhydrous forms, which are known to exist in the form of anhydrous crystal B, anhydrous crystal C, anhydrous crystal D, anhydrous crystal E, anhydrous crystal F, and anhydrous crystal G. All of these crystalline forms may be used as aripiprazole or a salt thereof in the injectable preparation of the present invention. Among these, a monohydrate form is preferable.

Such poorly soluble drugs are known compounds, and can be easily manufactured by known methods, or commercially available products can also be used.

The injectable preparation of the present invention preferably comprises at least water as a dispersion medium. Water, or an aqueous solvent comprising water and an organic solvent can be preferably used as a dispersion medium comprising at least water. Usable organic solvents are those that are miscible with water, such as methanol, ethanol, propanol, isopropanol, and like alcohols; acetone and like ketones; tetrahydrofuran and like ethers; dimethylformamide; and mixtures thereof. Among these, alcohols are preferable and ethanol is particularly preferable. Although not particularly limited, the amount of water in the aqueous solvent is preferably, for example, about 50 wt. % or more.

As the dispersion medium, water is preferable, and sterile water for injection is particularly preferable.

The specific suspending agent (suspending agent A) contained in the injectable preparation of the present invention comprises at least one suspending agent selected from the group consisting of (i) and (ii):
(i) polyvinylpyrrolidone, and
(ii) polyethylene glycol and carboxymethyl cellulose or a salt thereof.

The polyvinylpyrrolidone for use preferably has a K value (Fikentscher K value) of about 10 to 90, more preferably about 12 to 30, and even more preferably about 12 to 20. The polyvinylpyrrolidone for use preferably has an average molecular weight of about 2,000 to 700,000, more preferably about 2,000 to 40,000, and even more preferably about 2,000 to 10,000. The use of a polyvinylpyrrolidone having a K value and an average molecular weight within the aforementioned ranges is advantageous in terms of gelling the suspension of a poorly soluble drug upon standing, inhibiting caking due to the precipitation of particles, and providing an injectable preparation with excellent storage stability. Examples of polyvinylpyrrolidones include povidone K12, povidone K17, povidone K25, povidone K30, and the like. Povidone K17 is the most preferable. Such various polyvinylpyrrolidones can be used singly or in a combination of two or more.

Polyethylene glycols (macrogols) for use as suspending agent A preferably have an average molecular weight of about 100 to 10,000, more preferably about 150 to 8,000, and even more preferably about 200 to 5,000. The use of a polyethylene glycol having an average molecular weight within the aforementioned ranges can inhibit caking due to precipitation of particles and provide an injectable preparation with excellent storage stability. Examples of polyethylene glycols include commercially available polyethylene glycol 200, polyethylene glycol 300, polyethylene glycol 400, polyethylene glycol 600, polyethylene glycol 4000, polyethylene glycol 6000, polyethylene glycol 8000, and the like. Polyethylene glycol 400 is the most preferable. Such polyethylene glycols can be used singly or in a combination of two or more.

Examples of carboxymethyl cellulose or a salt thereof include carboxymethylcellulose and salts of carboxymethylcellulose, preferably such as alkali metal salts of carboxymethylcellulose and ammonium salts of carboxymethylcellulose. Specific examples thereof include sodium carboxymethylcellulose, potassium carboxymethylcellulose, lithium carboxymethylcellulose, ammonium carboxymethylcellulose, and the like. Among these, carboxymethylcellulose and sodium carboxymethylcellulose are preferable and sodium carboxymethylcellulose is particularly preferable. Such carboxymethylcellulose or salts thereof can be used singly or in a combination of two or more.

When allowed to stand for some time after production, the injectable preparation of the present invention has a high viscosity and loses fluidity (i.e., gels). However, having once gelled, the injectable preparation regains fluidity when subjected to a slight impact (for example, stirring, shaking, tapping, external impact, or pressure from being ejected through a syringe needle). Although a restrictive interpretation is not desired, the injectable preparation of the present invention is considered to exhibit structural viscosity. Structural viscosity is a type of non-Newtonian flow and refers to the following property: as an increasing shear stress is applied, weaker bonds in the internal structure of the liquid are broken and apparent viscosity decreases, so that the flow behavior becomes closer to Newtonian flow.

When such a fluid injectable preparation is allowed to stand again for some time, it returns to a gel state; upon mild impact (e.g., stirring, shaking, etc.), the gelled injectable preparation becomes fluid; and when allowed to stand again, the preparation becomes a gel. Thus, the injectable preparation is considered to exhibit a thixotropic property (thixotropy).

This property can be confirmed by measuring the viscosity of the injectable preparation with a rheometer. The rheometer is an advanced viscometer that can use various parameters and accurately measure viscosity under the conditions of each parameter. When the viscosity of the injectable preparation of the present invention is measured by a rheometer while gradually increasing the shear rate, the viscosity tends to gradually lower. A rotary rheometer is preferably used as the rheometer. Such rheometers include, for example, Discovery Hybrid Rheometer-2-(DHR-2) and Discovery Hybrid Rheometer-3 (DHR-3) (manufactured by TA Instruments).

In particular, because (α) the injectable preparation of the present invention becomes a gel upon standing, precipitation and caking of the particles of the poorly soluble drug can be inhibited, thereby providing excellent storage stability. Furthermore, because (β) the injectable preparation of the present invention even in the form of a gel can easily gain fluidity when subjected to a mild impact, the preparation can be easily injected at the time of use (at the time of injection). In particular, because the gelled injectable preparation (gel composition) gains fluidity (forms a sol state) by simply pressing the plunger of a syringe and ejecting the preparation through a syringe needle, the preparation can be smoothly ejected through the needle as is. Therefore, the preparation can be well dispersed intramuscularly or subcutaneously with relatively less local disturbance and pain at the time of injection.

Whether the injectable preparation is gelled or not (i.e., whether the preparation provides the above effect (α) or not) can be confirmed by whether or not the preparation exhibits a viscosity of about 40 Pa·s or more in at least one point in the shear rate range of 0.01 to 0.02 $s^{-1}$, as measured by a rheometer. Specifically, having a viscosity of about 40 Pa·s or more in the shear rate range of 0.01 to 0.02 s indicates that the injectable preparation being measured has lost fluidity and is in the form of a gel. In particular, having a viscosity of about 100 Pa·s or more in the shear rate range of 0.01 to 0.02 $s^{-1}$ indicates that the injectable preparation being measured has surely lost fluidity and is in the form of a gel. The measured viscosity value is preferably about 40 to 20,000 Pa·s, more preferably about 50 to 10,000 Pa·s, even more preferably about 75 to 5,000 Pa·s, and particularly preferably about 100 to 3,000 Pa·s, in at least one point in the shear rate range of 0.01 to 0.02 $s^{-1}$. Further, in the shear rate range of 0.01 to 0.02 $s^{-1}$, the viscosity is preferably about 40 Pa·s or more (particularly about 100 Pa·s or more), more preferably about 40 to 20,000 Pa·s, even more preferably about 50 to about 10,000 Pa·s, still more preferably about 75 to 5,000 Pa·s, and particularly preferably about 100 to 3,000 Pa·s.

Whether the injectable preparation provides the above effect (β) or not can be confirmed by whether or not the preparation exhibits a viscosity of 0.2 Pa·s or less in at least one point in the shear rate range of 900 to 1,000 $s^{-1}$, as measured by a rheometer. Specifically, having a viscosity of about 0.2 Pa·s or less in at least one point in the shear rate range of 900 to 1,000 $s^{-1}$ indicates that the injectable preparation being measured has acquired fluidity and is in the form of a sol. The measured viscosity value is preferably about 0.1 Pa's or less, and more preferably about 0.05 Pa·s or less in at least one point in the shear rate range of 900 to 1,000 $s^{-1}$. Further, in the shear rate range of 900 to 1,000 $s^{-1}$, the viscosity is preferably about 0.2 Pa·s or less, more preferably about 0.1 Pa·s or less, and even more preferably about 0.05 Pa·s or less.

Whether the injectable preparation is gelled or not (i.e., whether the preparation provides the above effect (α) or not) can be confirmed particularly by whether or not the preparation exhibits a viscosity of about 40 Pa·s or more in at least one point in the shear rate range of 0.01 to 0.02 $s^{-1}$, as measured by a rheometer at 25° C. Specifically, having a viscosity of about 40 Pa·s or more in at least one point in the shear rate range of 0.01 to 0.02 $s^{-1}$ indicates that the injectable preparation being measured has lost fluidity and is in the form of a gel. In particular, having a viscosity of about 100 Pa·s or more in the shear rate range of 0.01 to 0.02 $s^{-1}$ indicates that the injectable preparation being measured has surely lost fluidity and is in the form of a gel. The measured viscosity value is preferably about 40 to 20,000 Pa·s, more preferably about 50 to 10,000 Pa·s, even more preferably about 75 to 5,000 Pa·s, and particularly preferably about 100 to 3,000 Pa·s, n at least one point in the shear rate range of 0.01 to 0.02 $s^{-1}$. Further, in the shear rate range of 0.01 to 0.02 $s^{-1}$, the viscosity is preferably about 40 Pa·s or more (particularly about 100 Pa·s or more), more preferably about 40 to 20,000 Pa·s, even more preferably about 50 to about 10,000 Pa·s, still more preferably about 75 to 5,000 Pa·s, and particularly preferably about 100 to 3,000 Pa·s.

Whether the injectable preparation provides the above effect (β) or not can be confirmed particularly by whether or not the preparation exhibits a viscosity of 0.2 Pa·s or less in at least one point in the shear rate range of 900 to 1,000 s$^{-1}$, as measured by a rheometer at 25° C. Specifically, having a viscosity of about 0.2 Pa·s or less in the shear rate range of 900 to 1,000 s indicates that the injectable preparation being measured has acquired fluidity and is in the form of a sol. The measured viscosity value is preferably about 0.1 Pa·s or less, and more preferably about 0.05 Pa's or less in at least one point in the shear rate range of 900 to 1,000 sr. Further, in the shear rate range of 900 to 1,000 s$^{-1}$, the viscosity is preferably about 0.2 Pa·s or less, more preferably about 0.1 Pa·s or less, and even more preferably about 0.05 Pa's or less.

The viscosity measurement in these shear rate ranges (0.01 to 0.02 s$^{-1}$ and 900 to 1,000 s$^{-1}$) is preferably performed by sequentially measuring the viscosity while starting at the lowest shear rate and gradually increasing the shear rate. Preferably, for example, the viscosity is sequentially measured in the shear rate range of 0.001 to 1,000 s$^{-1}$ using a rheometer.

When the results of the sequential viscosity measurement of the gel composition are plotted with the shear rate (s$^{-1}$) on the abscissa (x-axis) and the viscosity (Pa·s) on the ordinate (y-axis), a roughly decreasing graph is obtained. Using this graph, the above content can be re-explained as follows. As an example, having a viscosity of 40 Pa·s or more in at least one point in the shear rate range of 0.01 to 0.02 s$^{-1}$ means that at least a part of the graph in the shear rate range of 0.01≤x≤0.02 satisfies y≥40. As another example, having a viscosity of 40 Pa·s or more in the shear rate range of 0.01 to 0.02 s$^{-1}$ means that the entire graph in the shear rate range of 0.01≤x≤0.02 satisfies y≥40. As another example, having a viscosity of 0.2 Pa·s or less in at least one point in the shear rate range of 900 to 1,000 s$^{-1}$ means that at least a part of the graph in the shear rate range of 900≤x≤1,000 satisfies y≤0.2. And as another example, having a viscosity of 0.2 Pa·s or less in the shear rate range of 900 to 1,000 s$^{-1}$ means that the entire graph in the shear rate range of 900≤x≤1,000 satisfies y≤0.2.

As the rheometer, for example, the Discovery Hybrid Rheometer-2 (DHR-2) or Discovery Hybrid Rheometer-3 (DHR-3) (produced by TA Instruments) can be used.

The use of the above specific suspending agent (suspending agent A) in combination with the poorly soluble drug is one of the main reasons why the injectable preparation of the present invention can provide the above effects (α) and (β). More specifically, although a very wide variety of suspending agents for poorly soluble drugs are known, most of the suspending agents fail to provide a composition that can produce the above effects (α) and (β); the above suspending agent A is highly suitable for obtaining an injectable preparation that has the above effects (α) and (β). Accordingly, the injectable preparation of the present invention can be obtained by preparing a suspension using a poorly soluble drug and a dispersion medium in combination with suspending agent A, measuring the viscosity, and selecting the suspension that satisfies the above conditions.

Other important factors for obtaining the above effects (α) and (β) are, for example, the particle diameter and concentration of the poorly soluble drug.

The poorly soluble drug contained in the injectable preparation of the present invention typically has a mean primary particle diameter of about 0.5 to 100 μm, preferably about 0.5 to 50 μm, more preferably about 0.5 to 30 μm, even more preferably about 1 to 20 μm, still even more preferably about 1 to 10 μm, yet more preferably about 1 to 5 μm, and particularly preferably about 2 to 5 μm. The mean secondary particle diameter of the poorly soluble drug is preferably up to but not exceeding three times, and more preferably up to but not exceeding twice, the mean primary particle diameter thereof.

The term "primary particle diameter" refers to the diameter of individual particles that are not aggregated but are separate from each other. "Mean primary particle diameter" is calculated from the volume mean diameter calculated from a mean primary particle size distribution measured by a laser diffraction scattering method. In the present invention, the mean primary particle diameter is measured while circulating the injectable preparation in a water medium with ultrasonic irradiation. "The secondary particle diameter" refers to the diameter of particles that are aggregated. "Mean secondary particle diameter" is calculated from the volume mean diameter calculated from a mean secondary particle size distribution measured by a laser diffraction scattering method. In the present invention, the mean secondary particle diameter is measured while circulating the injectable preparation in a water medium without ultrasonic irradiation.

For example, the SALD-3000J (manufactured by Shimadzu Corporation) can be used to measure the mean particle diameter by the laser diffraction scattering method.

The mean secondary particle diameter is not smaller than the mean primary particle diameter (excluding the measurement error range). Injectable preparations comprising a poorly soluble drug whose mean primary particle diameter and mean secondary particle diameter are almost the same (i.e., whose particles hardly aggregate) are also included within the scope of the injectable preparation of the present invention. Preferable are poorly soluble drugs that have a mean secondary particle diameter that is larger than the mean primary particle diameter thereof unless a specific operation (an operation for pulverizing secondary particles into primary particles) such as ultrasonic irradiation is performed.

When the mean primary particle diameter of the poorly soluble drug is set to 1 μm or more and used as an injection, long-term sustained release properties can be advantageously obtained. The mean primary particle diameter of the poorly soluble drug is preferably set to about 100 μm or less, more preferably about 50 μm or less, even more preferably about 30 μm or less, still more preferably 10 μm or less, and particularly preferably about 2 to 5 μm, because it inhibits the precipitation of the poorly soluble drug during the production of the composition of the present invention or during the period from the production thereof until administration to a patient, and also prevents clogging of the syringe needle at the time of injection.

As a method for preparing a poorly soluble drug having the above-mentioned mean primary particle diameter, a wet milling process is preferably used. The wet milling process is preferably wet ball milling, high-pressure homogenization, high-shear homogenization, or the like. In addition to such pulverization methods, other low- and high-energy mills (such as roller mills) can also be employed.

Controlled crystallization, etc., can be mentioned as other usable methods.

Further, as a method for producing a poorly soluble drug having the above-mentioned mean primary particle diameter, an impinging jet crystallization method (see JP2007-509153A) for which a patent application has been filed by Bristol-Myers Squibb Corp., or a wet milling process using a high-pressure homogenizer (see JP2007-200088A) for which a patent application has been filed by Otsuka Pharmaceutical Co., Ltd. can be used. The wet milling process (in particular, a two-step wet milling process) using a high-pressure homogenizer for which a patent application has been filed by Otsuka Pharmaceutical Co., Ltd. is more preferable.

The injectable preparation of the present invention preferably contains the poorly soluble drug in a concentration of about 200 to 600 mg/mL, more preferably about 200 to 500 mg/mL, even more preferably about 200 to 480 mg/mL, and still more preferably about 250 to 450 mg/mL.

The injectable preparation comprising the above suspending agent A and a poorly soluble drug that meets the aforementioned mean particle diameter and concentration conditions can more advantageously provide the above effects ($\alpha$) and ($\beta$).

The concentration of suspending agent A (the above suspending agent (i) or (ii)) in the injectable preparation of the present invention is preferably about 0.05 to 150 mg/mL, more preferably about 0.1 to 100 mg/mL, and still more preferably about 0.2 to 50 mg/mL.

When the injectable preparation of the present invention comprises the above suspending agents (i) and (ii) as suspending agent A, the total concentration thereof is preferably about 0.05 to 150 mg/mL, more preferably about 0.1 to about 100 mg/mL, and further preferably about 0.2 to 50 mg/mL.

In addition to the poorly soluble drug, suspending agent A, and dispersion medium, the injectable preparation of the present invention may further contain a suspending agent other than suspending agent A (hereinafter also referred to as "suspending agent B"), a buffer, a pH adjuster, an excipient, a lubricant, a plasticizer, a disintegrator, a binder, a surfactant, a preservative, a flavoring agent, a perfuming agent, a tonicity agent, and like additives.

For example, the additives disclosed in JP2007-509148A may be used as such additives.

Examples of other suspending agents that can be suitably used as suspending agent B include various polymers, low molecular weight oligomers, natural products, and surfactants (including nonionic and ionic surfactants). Specific examples thereof include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives; dodecyl trimethyl ammonium bromide, polyoxyethylene stearate, colloidal silicon dioxide, phosphate, sodium dodecyl sulfate, methylcellulose, hydroxyethylcellulose, hydroxypropylmethylcellulose phthalate, non-crystalline cellulose, aluminum magnesium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamines (e.g., Tetronic 908 (registered trademark), also known as Poloxamine 908 (registered trademark), which is a tetrafunctional block copolymer derived from the sequential addition of propylene oxide and ethylene oxide to ethylenediamine (BASF Wyandotte Corporation, Parsippany, N.J.)); charged phospholipids, such as dimyristoyl phosphatidyl glycerol and dioctylsulfosuccinate (DOSS); Tetronic 1508 (registered trademark) (T-1508) (BASF Wyandotte Corporation), dialkylesters of sodium sulfosuccinic acid (e.g., Aerosol OT (registered trademark), which is a dioctyl ester of sodium sulfosuccinic acid (American Cyanamid)); Duponol P (registered trademark), which is sodium lauryl sulfate (DuPont); Tritons X-200 (registered trademark), which is an alkyl aryl polyether sulfonate (Rohm and Haas); Crodestas F-110 (registered trademark), which is a mixture of sucrose stearate and sucrose distearate (Croda Inc.); p-isononylphenoxypoly-(glycidol), also known as Olin-lOG (registered trademark) or Surfactant 10-G (registered trademark) (Olin Chemicals, Stamford, Conn.); Crodestas SL-40 (Croda, Inc.); and SA9OHCO, which is $C_{16}H_{37}CH_2(CON(CH_3))$—$CH_2(CHOH)_4(CH_2OH)_2$ (Eastman Kodak Co.); decanoyl-N-methylglucamide; n-decyl-$\beta$-D-glucopyranoside; n-decyi-$\beta$-D-maltopyranoside; n-dodecyl-$\beta$-D-glucopyranoside; n-dodecyl-$\beta$-D-maltoside; heptanoyl-N-methylglucamide; n-heptyl-$\beta$-D-glucopyranoside; n-heptyl-$\beta$-D-thioglucoside; n-hexyl-$\beta$-D-glucopyranoside; nonanoyl-N-methylglucamide; n-nonyl-$\beta$-D-glucopyranoside; octanoyl-N-methylglucamide; n-octyl-$\beta$-D-glucopyranoside; octyl-$\beta$-D-thioglucopyranoside; and the like.

Such suspending agents B are known pharmaceutical excipients, and are described in detail in the Handbook of Pharmaceutical Excipients, published jointly by the American Pharmaceutical Association and The Pharmaceutical Society of Great Britain (The Pharmaceutical Press, 1986), which is herein specifically incorporated by reference. Such suspending agents B are commercially available or can be prepared by techniques known in the art.

The concentration of suspending agent B is preferably about 0.1 to 50 mg/mL, more preferably about 0.1 to 20 mg/mL, and more preferably about 0.3 to 15 mg/mL.

In addition to (i) polyvinylpyrrolidone, polyethylene glycol is preferably used in admixture therewith. In this case, the concentration of polyvinylpyrrolidone is preferably about 0.1 mg/mL or more, and more preferably about 0.1 to 100 mg/mL, whereas the concentration of polyethylene glycol is preferably about 0.05 to 100 mg/mL, and more preferably about 0.1 to 50 mg/mL. When polyethylene glycol 400 is used as a polyethylene glycol, the concentration of polyethylene glycol 400 is preferably about 0.1 to 100 mg/mL, more preferably about 0.1 to 10 mg/mL, and even more preferably about 0.5 to 5 mg/mL. When polyethylene glycol 4000 is used as a polyethylene glycol, the concentration of polyethylene glycol 4000 is preferably about 0.1 to 40 mg/mL.

When (ii) polyethylene glycol and carboxymethyl cellulose or a salt thereof are used as suspending agents A, the concentration of polyethylene glycol is preferably about 0.05 to 2 mg/mL, and more preferably about 0.1 to 1 mg/mL.

When carboxymethyl cellulose or a salt thereof is used in admixture with (i) polyvinylpyrrolidone or (ii) polyethylene glycol and carboxymethyl cellulose or a salt thereof are used as suspending agents A, the concentration of carboxymethyl cellulose or a salt thereof is preferably about 0.5 to 50 mg/mL, more preferably 1 to 30 mg/mL, and even more preferably 2 to 20 ng/mL.

By containing carboxymethylcellulose or a salt thereof, an increase in viscosity during production can be suppressed. This allows a poorly soluble drug such as aripiprazole or a salt thereof to be pulverized into a desirable particle size in an efficient manner, thus preferable. Furthermore, by containing polyethylene glycol, syneresis can be preferably prevented even when the resulting injectable preparation is stored for a long period of time.

The dispersion medium is incorporated in an amount suitable for the poorly soluble drug content to fall within the above-mentioned range. For example, the dispersion medium is added in such an amount as to make a final injectable preparation volume of about 0.2 to 5.0 mL, more specifically about 0.4 to 3.0 mL, and even more preferably about 0.5 to 2.0 mL.

When the composition (injectable preparation) produced using the poorly soluble drug, the dispersion medium, and suspending agent A does not gel upon standing, it can be gelled by heat treatment (aging). Even in this case, as long as the effects of the present invention are advantageously provided, the resulting preparation can be preferably used as the injectable preparation of the present invention. Specifically, as long as the injectable preparation gelled in such a manner meets the above conditions, and, in particular, has a viscosity of 40 Pa·s or more in at least one point in the shear rate range of 0.01 to 0.02 $s^{-1}$ and has a viscosity of 0.2 Pa·s or less in at least one point in the shear rate range of 900 to 1,000 $s^{-1}$, as measured by a rheometer at 25° C., the preparation can be suitably used as the injectable preparation of the present invention. For example, by setting the temperature conditions upon standing to a higher temperature or by temporarily allowing the preparation to stand at a higher temperature and then allowing it to stand at ambient temperatures (about 25° C.), the gelling of the injectable preparation can be preferably promoted, thus producing the injectable preparation of the present invention.

The aging is performed by heating, for example, at about 30° C. or higher (preferably about 30° C. to 70° C., more preferably about 40'C to 60° C., and even more preferably about 45° C. to 55° C.) for several minutes to several days (for example, preferably for about 5 minutes to 5 days, more preferably for about 1 hour to 3 days, and even more preferably about 12 to 24 hours). However, heating at a temperature of 90° C. or higher is undesirable because it would cause water to evaporate. The aging tends to increase the secondary particle diameter of the poorly soluble drug. However, even when aging is performed, the mean secondary particle diameter of the poorly soluble drug is preferably up to but not exceeding three times, and more preferably up to but not exceeding twice, the mean primary particle diameter thereof, as described above. It is also undesirable to allow the injectable preparation to stand at a temperature as low as the temperature at which the injectable preparation freezes.

As can be understood from the above, when the injectable preparation is allowed to stand to gel the preparation, the standing temperature is preferably about 5° C. to 70° C., more preferably about 20° C. to 70° C., and even more preferably about 25° C. to 65° C.

The standing time depends on the amount of the injectable preparation to be gelled and the standing temperature, and may be any length of time as long as it is not less than the time required to gel the preparation. For example, the standing time is preferably 5 minutes or more, more preferably 10 minutes or more, even more preferably 30 minutes or more, and still more preferably 1 hour or more. When the standing time is 1 hour or more, a preferable standing time is 4 hours or more, more preferably 12 hours or more, and even more preferably 24 hours or more. There is no particular upper limit for the standing time, either, and the time may be, for example, about several days (2, 3, 4, or 5 days).

As described above, aging can be incorporated during standing (preferably at the beginning of standing).

The injectable preparation of the present invention may contain a tonicity agent. Examples of the tonicity agent include, but are not limited to, sodium chloride, potassium chloride, mannitol, glycerol, sorbitol, glucose, xylitol, trehalose, maltose, maltitol, and the like. Such tonicity agents can be used singly or in a combination of two or more. Sodium chloride is more preferable. Such a tonicity agent is added in an amount to render the composition isotonic.

The buffer is used to adjust the pH of the suspension to about 6 to 8, and preferably about 7. To achieve such a pH, the concentration of the buffer can be suitably set according to the type of buffer. The concentration of the buffer is preferably about 0.02 to 2 mg/mL, and more preferably about 0.03 to 1 mg/mL.

Specific examples of buffers include, but are not limited to, sodium phosphate, monosodium hydrogen phosphate, disodium hydrogen phosphate, potassium phosphate, hydrates thereof, TRIS buffer, and the like. Such buffers can be used singly or as a mixture of two or more. Sodium phosphate, monosodium hydrogen phosphate, disodium hydrogen phosphate, and hydrates thereof are preferable.

The pH adjuster is used in an amount to adjust the aqueous suspension of the poorly soluble drug to a pH of about 6 to 7.5, and preferably about 7. An acid or a base is used depending on the pH of the injectable preparation of the present invention. When the injectable preparation is to be adjusted to a lower pH, an acidic pH adjuster, such as hydrochloric acid or acetic acid, can be used. Hydrochloric acid is preferably used. When the injectable preparation needs to be adjusted to a higher pH, a basic pH adjuster, such as sodium hydroxide, potassium hydroxide, calcium carbonate, magnesium oxide, or magnesium hydroxide, can be used. Sodium hydroxide is preferably used. Such pH adjusters can be used singly or in a combination of two or more.

Although the method of preparing the injectable preparation of the present invention is not particularly limited, the injectable preparation is prepared by mixing a poorly soluble drug, suspending agent A, and a dispersion medium optionally with additives. More specifically, after suspending agent A and a dispersion medium are mixed optionally with additives, the obtained vehicle solution is mixed with a poorly soluble drug, and the resulting mixture is subjected to wet milling by the above method, thus providing the injectable preparation of the present invention. To prevent gelling of the injectable preparation, the injectable preparation is preferably produced at a low temperature (for example, about 2 to 10° C., particularly about 5° C.).

A storage-stable injectable preparation comprising a poorly soluble drug having a desired mean particle diameter can be obtained by the above method.

The injectable preparation of the present invention is suitably formulated into a dosage form that can be administered once per month, once every two months, or once every three months. Although the injectable preparation is preferably administered intramuscularly, subcutaneous injection is also acceptable.

In particular, when the poorly soluble drug contained in the injectable preparation of the present invention is aripiprazole or a salt thereof, the injectable preparation is preferably used to treat schizophrenia and associated disorders (such as bipolar disorder, depression, and dementia) in human patients or to prevent the recurrence of symptoms of such diseases.

As described above, the injectable preparation of the present invention, which contains a specific suspending agent A, inhibits caking due to the precipitation of a poorly soluble drug during the period from the production thereof until the administration to a patient and thus has excellent storage stability, and can be smoothly ejected from a syringe through a thin syringe needle at the time of injection.

In particular, when the injectable preparation of the present invention has structural viscosity, the injectable preparation is in a sol state exhibiting fluidity immediately after the preparation thereof (see FIG. 1). When the sol injectable preparation is allowed to stand, the injectable preparation becomes a gel and no longer flows even when tilted slowly (see FIG. 2). The injectable preparation in the form of a gel is so stable that the caking of particles of a poorly soluble drug due to the precipitation of the particles does not occur even when allowed to stand for a long period of time. The gelled injectable preparation quickly forms a sol state due to stirring, shaking, tapping, external impact, or the pressure from being ejected through a syringe needle (see FIG. 3). In the sol-state injectable preparation, the poorly soluble drug does not cake due to precipitation but is uniformly dispersed to reproduce the injectable preparation immediately after production.

Although a restrictive interpretation is not desired, it is hypothesized that the following mechanism causes the structural viscosity and thixotropy of such an injectable preparation.

The injectable preparation is considered to have a structure such that part of suspending agent A is attached to the particles of a poorly soluble drug in a dispersion medium; therefore, the attached suspending agent A causes an interaction between the particles of the poorly soluble drug.

Presumably, there is an intermolecular and interparticle interaction between the molecules of the suspending agent A attached to the particle surface of the poorly soluble drug, or between the molecules of the suspending agent A attached to the particle surface of the poorly soluble drug and those of the suspending agent A that is present in an unattached state in the dispersion medium, or between the particles of the poorly soluble drug, thus forming a network structure. It is assumed that the injectable preparation becomes a gel due to this network structure.

The intermolecular interaction due to suspending agent A that forms the network structure is a weak binding force. Therefore, due to stirring, shaking, tapping, external impact, the pressure from being ejected through a syringe needle, etc., the network structure collapses, with the result being that the gelled injectable preparation changes into a sol. When the injectable preparation is in a sol state, the network structure is reconstructed and the injectable preparation becomes a gel again upon standing.

The injectable preparation of the present invention is also advantageous in that it can be filled into a vial or a syringe as is.

One example of a conventional dosage form of aripiprazole or a salt thereof is such that a suspension comprising aripiprazole or a salt thereof as an active ingredient is prepared, and the suspension is freeze dried in a vial. Before use, water for injection is added into the vial, and the resulting formulation is drawn into a syringe and then administered to a patient.

According to a usage form of the present invention, the injectable preparation is filled as is into a vial or a syringe and used. Thus, the injectable preparation of the present invention can be easily obtained without the need for freeze-drying in the production process.

In particular, the injectable preparation of the present invention can be filled as is into a syringe for use as a prefilled syringe. This simplifies the structure of the syringe and reduces size and weight. When the injectable preparation of the present invention is filled into a syringe, in a preferred embodiment, a sol suspension can be administered by simply pressing the plunger rod of the syringe and ejecting the injectable preparation of the invention through a syringe needle without the need to shake the syringe. This provides a prefilled syringe that offers clinical convenience and operability, thus is highly useful medically and industrially. A preferable example of producing such a prefilled syringe is such that an injectable preparation is produced in the manner as described above, the preparation is prefilled into a syringe, and then left to stand in the manner as described above to cause the injectable preparation to gel. The present invention also includes a kit equipped with the above-described prefilled syringe.

Aripiprazole or a salt thereof, or 7-[4-(4-benzo[b]thiophen-4-yl-piperazin-1-yl)butoxy]-1H-quinolin-2-one or a salt thereof is particularly preferable for use as the poorly soluble drug contained in the injectable preparation of the present invention. Therefore, more preferable embodiments of the injectable preparation containing aripiprazole or a salt thereof as a poorly soluble drug, or those of the injectable preparation containing 7-[4-(4-benzo[b]thiophen-4-yl-piperazin-1-yl)butoxy]-1H-quinolin-2-one or a salt thereof as a poorly soluble drug are explained below. However, unless otherwise defined below, the above explanations are also applicable to the injectable preparation containing an aripiprazole or a salt thereof, or 7-[4-(4-benzo[b]thiophen-4-yl-piperazin-1-yl)butoxy]-1H-quinolin-2-one or a salt thereof as a poorly soluble drug.

The injectable preparation of the present invention that contains aripiprazole or a salt thereof preferably comprises aripiprazole or a salt thereof, water, and at least one suspending agent selected from the group consisting of (i) and (ii):

(i) polyvinylpyrrolidone, and
(ii) polyethylene glycol and carboxymethylcellulose or a salt thereof, wherein aripiprazole or a salt thereof has a mean primary particle diameter of about 0.5 to 30 μm and the concentration of aripiprazole or a salt thereof is 200 to 600 mg/mL.

In particular, when the injectable preparation of the present invention comprises aripiprazole or a salt thereof (which hereunder may be referred to as "the aripiprazole injectable preparation of the present invention"), the concentration of aripiprazole or a salt thereof is important. When the concentration thereof falls outside the range of 200 to 600 mg/mL, it is difficult to obtain an injectable preparation that achieves both of the effects ($\alpha$) and ($\beta$) described above. In particular, when the concentration thereof is 100 mg/mL or below, the production of an injectable preparation that can form a gel is difficult even if the suspending agent A is used (or an aging treatment is further performed). Therefore, when the injectable preparation of the present invention comprises aripiprazole or a salt thereof, a combination of the use of a specific suspending agent (suspending agent A) and a specific concentration of aripiprazole or a salt thereof (200 to 600 mg/mL and more preferably 250 to 450 mg/mL) is particularly important. When the injectable preparation of the present invention comprises a salt of aripiprazole, the concentration described above is preferably that calculated as aripiprazole.

The injectable preparation containing 7-[4-(4-benzo[b]thiophen-4-yl-piperazin-1-yl)butoxy]-1H-quinolin-2-one or a salt thereof of the present invention comprises 7-[4-(4-benzo[b]thiophen-4-yl-piperazin-1-yl)butoxy]-1H-quinolin-2-one or a salt thereof, water, and at least one suspending agent selected from the group consisting of (i) and (ii):

(i) polyvinylpyrrolidone, and
(ii) polyethylene glycol and carboxymethylcellulose or a salt thereof, wherein 7-[4-(4-benzo[b]thiophen-4-yl-piperazin-1-yl)butoxy]-1H-quinolin-2-one or a salt thereof has a mean primary particle diameter of about 0.5 to 30 µm, and the concentration of 7-[4-(4-benzo[b]thiophen-4-yl-piperazin-1-yl)butoxy]-1H-quinolin-2-one or a salt thereof is 200 to 600 mg/mL.

In particular, when the injectable preparation of the present invention comprises 7-[4-(4-benzo[b]thiophen-4-yl-piperazin-1-yl)butoxy]-1H-quinolin-2-one or a salt thereof (which hereunder may be referred to as "the brexpiprazole injectable preparation of the present invention"), the concentration of 7-[4-(4-benzo[b]thiophen-4-yl-piperazin-1-yl)butoxy]-1H-quinolin-2-one or a salt thereof is important. When the concentration thereof falls outside the range of 200 to 600 mg/mi, it is difficult to obtain an injectable preparation that achieves both of the effects (α) and (β) described above. In particular, when the concentration thereof is 100 mg/mL or below, the production of an injectable preparation that can form a gel is difficult even if the suspending agent A is used (or an aging treatment is further performed). Therefore, when the injectable preparation of the present invention comprises 7-[4-(4-benzo[b]thiophen-4-yl-piperazin-1-yl)butoxy]-1H-quinolin-2-one or a salt thereof, a combination of the use of a specific suspending agent (suspending agent A) and a specific concentration of 7-[4-(4-benzo[b]thiophen-4-yl-piperazin-1-yl)butoxy]-1H-quinolin-2-one or a salt thereof (200 to 600 mg/mL and more preferably 250 to 450 mg/mL) is particularly important. When the injectable preparation of the present invention comprises a salt of brexpiprazole, the concentration described above is preferably that calculated as brexpiprazole.

In the aripiprazole injectable preparation of the present invention or the brexpiprazole injectable preparation of the present invention, when (i) polyvinylpyrrolidone is contained as suspending agent A, the concentration of polyvinylpyrrolidone is preferably 0.1 to 100 ng/mi, more preferably 1 to 50 mg/mL, and even more preferably 2 to 20 mg/mL.

When the aripiprazole injectable preparation of the present invention or the brexpiprazole injectable preparation of the present invention comprises (i) polyvinylpyrrolidone as suspending agent A, and further comprises one or more other suspending agents, it is preferable that at least one member selected from the group consisting of polyethylene glycol and carboxymethylcellulose or a salt thereof be contained as the one or more other suspending agents. More specifically, these injectable preparations of the present invention comprise (i) polyvinylpyrrolidone as suspending agent A, and when they further comprise one or more other suspending agents, they preferably comprise suspending agents of any combination of (i-1) to (i-3) shown below.

(i-1) polyvinylpyrrolidone and polyethylene glycol (i-2) polyvinylpyrrolidone and carboxymethylcellulose or a salt thereof, and (i-3) polyvinylpyrrolidone, polyethylene glycol, and carboxymethylcellulose or a salt thereof Regardless of which combination of (i-1) to (i-3) these injectable preparations of the present invention comprise, the concentration of polyvinylpyrrolidone is, as described above, preferably 0.1 to 100 mg/mL, more preferably 1 to 50 mg/mL, and even more preferably 2 to 20 mg/mL. In (i-1) or (i-31, the concentration of polyethylene glycol is preferably about 0.05 to 100 mg/mi and more preferably about 0.1 to 50 g/mL. In (i-2) or (i-3), the concentration of carboxymethylcellulose or a salt thereof is preferably about 0.5 to 50 mg/mL, more preferably 1 to 30 mg/mL, and even more preferably 2 to 20 mg/mL.

By containing carboxymethylcellulose or a salt thereof, an increase in viscosity during production can be suppressed. This allows aripiprazole or a salt thereof, brexpiprazole or a salt thereof to be pulverized into a desirable particle size in an efficient manner, thus preferable. Furthermore, by containing polyethylene glycol, syneresis can be preferably prevented even when the resulting injectable preparation is stored for a long period of time. Among (i-1) to (i-3), (i-3) is particularly preferable as both effects described above can be achieved.

When the aripiprazole injectable preparation of the present invention or the brexpiprazole injectable preparation of the present invention comprises (ii) polyethylene glycol and carboxymethylcellulose or a salt thereof as suspending agent A, the concentration of polyethylene glycol is preferably about 0.05 to 2 mg/mL and more preferably about 0.1 to 1 mg/mL. The concentration of carboxymethylcellulose or a salt thereof is preferably about 0.5 to 50 mg/mL, more preferably 1 to 30 mg/mL, and even more preferably 2 to 20 mg/mL.

When the aripiprazole injectable preparation of the present invention or the brexpiprazole injectable preparation of the present invention comprises (ii) polyethylene glycol and carboxymethylcellulose or a salt thereof as suspending agent A, and further comprises one or more other suspending agents, polyvinylpyrrolidone is preferably contained as the one or more other suspending agents. Specifically, the injectable preparation of the present invention comprises, as suspending agent A, (ii) polyethylene glycol and carboxymethylcellulose or a salt thereof, and when it further comprises one or more other suspending agents, it is more preferable that the suspending agents of (i-3) are contained. In this case, the concentration of polyethylene glycol, carboxymethylcellulose or a salt thereof, and polyvinylpyrrolidone are the same as described in (i-3) above.

In the aripiprazole injectable preparation of the present invention or the brexpiprazole injectable preparation of the present invention, when the suspending agents of (i-3) are used, the particularly preferable composition contains 0.5 to 20 mg/mL of polyvinylpyrrolidone, 0.1 to 100 mg/mL of polyethylene glycol, 0.5 to 50 mg/mL of carboxymethylcellulose or a salt thereof, and 250 to 450 mg/mL (more preferably 300 to 400 mg/mL) of aripiprazole or a salt thereof. In this case, it is more preferable that the polyethylene glycol be polyethylene glycol 400 or polyethylene glycol 4000. Even more preferably, the polyvinylpyrrolidone has a K value of about 12 to 20. Still more preferably, the aripiprazole or a salt thereof has a mean primary particle diameter of about 1 to 10 µm.

Because an unduly large mean primary particle diameter of the aripiprazole or a salt thereof, or 7-[4-(4-benzo[b]thiophen-4-yl-piperazin-1-yl)butoxy]-1H-quinolin-2-one or a salt thereof may cause precipitation, the mean primary particle diameter is preferably about 0.5 to 30 µm and more preferably about 1 to 20 µm. In order to maintain the sustained release effect, when the injectable preparation of the present invention is in a dosage form that is administered once a month, the aripiprazole or a salt thereof, or 7-[4-(4-benzo[b]thiophen-4-yl-piperazin-1-yl)butoxy]-1H-quinolin-2-one or a salt thereof has a mean primary particle diameter of preferably about to 10 µm, and more preferably 2 to 7 µm, and even more preferably 2 to 4 µm. When the injectable preparation of the present invention is in a dosage form that is administered once every two or three months, the aripiprazole or a salt thereof, or 7-[4-(4-benzo[b]thiophen-4-yl-piperazin-1-yl)butoxy]-1H-quinolin-2-one or a salt thereof has a mean primary particle diameter of preferably about 1 to 50 µm, more preferably 4 to 30 µm, and even more preferably 5 to 20 µm. The mean secondary particle diameter is preferably up to but not exceeding three times and more preferably up to but not exceeding twice the mean primary particle diameter.

The aripiprazole injectable preparation of the present invention is explained in further detail below. The concentration of aripiprazole or a salt thereof in the injectable preparation of the present invention that is administered once per month is preferably, calculated as aripiprazole, about 200 to 600 mg/mL, more preferably about 200 to 400 mg/mL, and even more preferably about 300 mg/mL. In the injectable preparation of the present invention that is administered once per month, the aripiprazole or a salt thereof has a mean primary particle diameter of preferably about 1 to 10 µm, more preferably 1 to 5 µm, and even more preferably 2 to 4 µm. The dosage volume is preferably 0.3 to 3 mL, more preferably 0.6 to 2 mL, and even more preferably 1 to 1.5 mL.

The concentration of aripiprazole or a salt thereof in the injectable preparation of the present invention that is administered once every two or three months, is preferably, calculated as aripiprazole, about 300 to 600 mg/mL, more preferably about 350 to 500 mg/mL, and even more preferably about 400 mg/mL. In the injectable preparation of the present invention that is administered once every two or three months, the aripiprazole or a salt thereof has a mean primary particle diameter of preferably about 1 to 30 µm, more preferably 4 to 20 µm, and even more preferably 5 to 10 µm. When the injectable preparation is administered once every two months, the dosage volume is preferably 0.5 to 5 mL, more preferably 1 to 3 mL, and even more preferably 1.5 to 2.5 mL. When the injectable preparation is administered once every three months, the dosage volume is preferably 0.7 to 8 mL, more preferably 1.5 to 4.5 mL, and even more preferably 2 to 4 mL.

The brexpiprazole injectable preparation of the present invention is explained in further detail below. The concentration of brexpiprazole or a salt thereof in the injectable preparation of the present invention that is administered once per month is preferably, calculated as brexpiprazole, about 200 to 600 mg/mL, more preferably about 200 to 400 mg/mL, and even more preferably about 300 mg/mL. In the injectable preparation of the present invention that is administered once per month, the brexpiprazole or a salt thereof has a mean primary particle diameter of preferably about 1 to 10 µm, more preferably 1 to 5 µm, and even more preferably 2 to 4 µm. The dosage volume is preferably 0.3 to 3 mL, more preferably 0.6 to 2 mL, and even more preferably 1 to 1.5 mL.

The concentration of brexpiprazole in the injectable preparation or a salt thereof of the present invention that is administered once every two or three months, is preferably, calculated as brexpiprazole, about 300 to 600 mg/mL, more preferably about 350 to 500 mg/mL, and even more preferably about 400 mg/mL. In the injectable preparation of the present invention that is administered once every two or three months, the brexpiprazole or a salt thereof has a mean primary particle diameter of preferably about 1 to 30 µm, more preferably 4 to 20 µm, and even more preferably 5 to 10 µm. When the injectable preparation is administered once every two months, the dosage volume is preferably 0.5 to 5 mL, more preferably 1 to 3 mL, and even more preferably 1.5 to 2.5 mL. When the injectable preparation is administered once every three months, the dosage volume is preferably 0.7 to 8 mL, more preferably 1.5 to 4.5 mL, and even more preferably 2 to 4 mL.

The aripiprazole injectable preparation of the present invention or the brexpiprazole injectable preparation of the present invention achieves the effects ($\alpha$) and ($\beta$) described above. They may be in the form of a gel or they may have fluidity (i.e., they may be in the form of a sol). As described above, the achievement of the effects of the effects ($\alpha$) and ($\beta$) can objectively confirmed by the use of a rotary rheometer.

A preferable method for producing the aripiprazole injectable preparation or brexpiprazole injectable preparation according to the present invention comprises preparing a liquid mixture of the starting materials and pulverizing aripiprazole or a salt thereof, or 7-[4-(4-benzo[b]thiophen-4-yl-piperazin-1-yl)butoxy]-1H-quinolin-2-one or a salt thereof, contained in the liquid mixture to a desired mean primary particle diameter, optionally followed by aging.

A particularly preferable method for producing the gel aripiprazole injectable preparation according to the present invention comprises allowing a liquid mixture to stand at 5 to 70° C. for 5 minutes or more, the liquid mixture comprising aripiprazole or a salt thereof with a mean primary particle diameter of 0.5 to 30 µm in a concentration of 200 to 600 mg/mL, water, and at least one suspending agent selected from the group consisting of (i) and (ii):
(i) polyvinylpyrrolidone and
(ii) polyethylene glycol and carboxymethyl cellulose or a salt thereof.

For example, a production method comprising the following steps can be preferably used: pulverizing aripiprazole or a salt thereof to a mean primary particle diameter of 0.5 to 30 µn in a liquid mixture comprising the aripiprazole or a salt thereof in a concentration of 200 to 600 mg/mL, water, and at least one suspending agent selected from the group consisting of (i) and (ii):
(i) polyvinylpyrrolidone and
(ii) polyethylene glycol and carboxymethyl cellulose or a salt thereof; and
allowing the pulverized liquid mixture to stand at 5 to 70° C. for 5 minutes or more.

A particularly preferable method for producing the gel brexpiprazole injectable preparation according to the present invention comprise allowing a liquid mixture to stand at 5 to 70° C. for 5 minutes or more, the liquid mixture comprising 7-[4-(4-benzo[b]thiophen-4-yl-piperazin-1-yl)butoxy]-1H-quinolin-2-one or a salt thereof with a mean primary particle diameter of 0.5 to 30 µm in a concentration of 200 to 600 mg/mL, water, and at least one suspending agent selected from the group consisting of (i) and (ii):
(i) polyvinylpyrrolidone and
(ii) polyethylene glycol and carboxymethyl cellulose or a salt thereof.

For example, a production method comprising the following steps can be preferably used: pulverizing 7-[4-(4-benzo[b]thiophen-4-yl-piperazin-1-yl)butoxy]-1H-quinolin-2-one or a salt thereof to a mean primary particle diameter of 0.5 to 30 µm in a liquid mixture comprising the 7-[4-(4-benzo[b]thiophen-4-yl-piperazin-1-yl)butoxy]-1H-quinolin-2-one or a salt thereof in a concentration of 200 to 600 mg/mL, water, and at least one suspending agent selected from the group consisting of (i) and (ii):
(i) polyvinylpyrrolidone and
(ii) polyethylene glycol and carboxymethyl cellulose or a salt thereof; and
allowing the pulverized liquid mixture to stand at 5 to 70° C. for 5 minutes or more.

In the production of these injectable preparations, it is preferable to allow the injectable preparations to stand at 5 to 70° C. for five minutes or more as described above, and more preferably, to conduct an aging treatment. By conducting an aging treatment, a gel composition can be more reliably produced compared to the case where, for example, an injectable preparation is allowed to stand at a low temperature or placed under the condition where an impact is applied intermittently. The above aging treatment conditions are less likely to cause problems, such as the evaporation of water, the firm gelling of the injectable preparation, and the inability of the injectable preparation to easily return to a sol even when an impact is applied thereto.

The concentration of the suspending agent contained in the liquid mixture is preferably the same as that of the suspending agent contained in the injectable preparation. This is because the concentration of the suspending agent in the liquid mixture will directly become the concentration thereof in the resulting injectable preparation.

As described above, the aripiprazole or a salt thereof added to the liquid mixture used for producing the aripiprazole injectable preparation of the present invention may be, for example, in the form of a monohydrate (aripiprazole hydrate A) and various anhydrous forms, i.e., anhydrous crystal B, anhydrous crystal C, anhydrous crystal D, anhydrous crystal E, anhydrous crystal F, or anhydrous crystal G. Preferably, the aripiprazole or a salt thereof is in the form of a monohydrate, and particularly preferably in the form of aripiprazole hydrate A. These may be used singly or in a combination of two or more.

The 7-[4-(4-benzo[b]thiophen-4-yl-piperazin-1-yl)butoxy]-1H-quinolin-2-one or a salt thereof added to the liquid mixture used in producing the brexpiprazole injectable preparation of the present invention is not limited, and may be, for example, in the form of an anhydride or dihydrate, and preferably in the form of a dihydrate. These may be used singly or in a combination of two or more.

The method for pulverizing aripiprazole or a salt thereof, or 7-[4-(4-benzo[b]thiophen-4-yl-piperazin-1-yl)butoxy]-1H-quinolin-2-one or a salt thereof contained in the liquid mixture is not particularly limited and any known methods can be employed. For example, the methods described above may be used. More specifically, a wet milling process is preferably used. As for the wet milling process, wet ball milling, high pressure homogenization, high shear homogenization and the like are preferably used. In addition to the aforementioned pulverization methods, other low- and high-energy mills (such as roller mills) can also be employed. Controlled crystallization and other methods may also be used. Further, an impinging jet crystallization method (see JP2007-509153A), for which a patent application has been filed by Bristol-Myers Squibb Corp., or a wet milling process using a high-pressure homogenizer (see JP2007-200088A), for which a patent application has been filed by Otsuka Pharmaceutical Co., Ltd., can be used. Among these, a wet milling process using a high-pressure homogenizer (in particular, a two-step wet milling process), for which a patent application has been filed by Otsuka Pharmaceutical Co., Ltd. is more preferable.

In the production of the gel aripiprazole injectable preparation or gel brexpiprazole injectable preparation, by filling the liquid mixture into a syringe and allowing it to stand therein, a prefilled syringe containing a gel aripiprazole injectable preparation or gel brexpiprazole injectable preparation prefilled therein can be obtained.

In the prefilled syringe thus obtained, the injectable preparation (gel composition) contained therein gains fluidity (becomes a sol) by simply pressing the plunger rod of the syringe and ejecting it through a syringe needle. This allows the injectable preparation of the present invention to be smoothly ejected from the syringe needle as is (i.e., achieving the effect (β) described above). Furthermore, the precipitation and caking of aripiprazole or a salt thereof, or 7-[4-(4-benzo[b]thiophen-4-yl-piperazin-1-yl)butoxy]-1H-quinolin-2-one or a salt thereof, can be suppressed, thus attaining excellent storage stability (i.e., achieving the effect (α) described above). This makes the injectable preparation of the present invention highly useful in clinical sites.

The present invention encompasses a kit comprising the prefilled syringe.

EXAMPLES

The present invention is more specifically explained below. The present invention is, however, not limited to these examples. The abbreviation "q.s." stands for "quantum sufficiat", which means "sufficient quantity".

Examples 1 to 7

The suspending agent, sodium chloride, and sodium dihydrogenphosphate monohydrate shown in Table 1 were dissolved in water (water for injection). The solution was adjusted to a pH value of 7.0 using sodium hydroxide to prepare a vehicle solution. An active ingredient (aripiprazole monohydrate) was suspended into the resulting vehicle solution. The resulting suspension was preliminarily pulverized using a CLEARMIX S1.5 (manufactured by M Technique Co., Ltd.) and finely pulverized using a high-pressure homogenizer (Panda model NS1001L2K, manufactured by Niro Soavi) to prepare injectable preparations. After the step of suspending the active ingredient into the vehicle solution, all of the steps for producing the injectable preparations were conducted at a temperature of 10° C. or lower.

Immediately after production, all of the injectable preparations were in the form of a sol-like suspension having fluidity. FIG. 1 shows a photograph of the injectable preparation of Example 1 immediately after production. When each of the resulting injectable preparations was placed in a transparent container and allowed to stand at 25° C. for one hour, all of the injectable preparations lost fluidity, thereby becoming gel-like injectable preparations. FIG. 2 shows a photograph of the container holding the injectable preparation of Example 1 therein, which was slowly tilted and laid horizontally after being allowed to stand. Furthermore, when gently shaken, all of the gelled injectable preparations returned to a sol state and re-exhibited fluidity. FIG. 3 shows a photograph of the container holding the injectable preparation of Example 1 therein after being allowed to stand, followed by tapping the container (i.e., a weak impact was applied to the gelled preparation), and laying the container horizontally.

After the injectable preparations produced in Examples 1 to 7 were gelled, the preparations were stored at 40° C. for one week and then shaken. Table 1 shows the mean particle diameter (mean secondary particle diameter) of each of the resulting preparations. Table 1 also shows the mean particle diameters (mean primary particle diameter) when ultrasonic treatment was applied while shaking. The particle diameters were measured by a laser diffraction scattering method using an SALD-3000J (manufactured by Shimadzu Corporation). The mean particle diameters of drugs contained in the injectable preparations (Production Examples) described below were also measured by the laser diffraction scattering method using an SALD-3000J.

After shaking the injectable preparations of Examples 1 to 7, 1.0 to 1.2 mL of each sample was collected. The viscosity was measured using a B-type rotational viscometer (TVE-30H, model name of a cone-and-plate rotational viscometer manufactured by Tokimec Inc.) under the conditions of 25° C., 50 rpm, and 120 seconds. Table 1 shows the evaluation results. The viscosity was measured according to Method 2, Viscosity Determination defined by the Japanese Pharmacopoeia.

produced in the same manner as in Examples 1 to 7 described above (i.e., mixing the components other than the active ingredient, adjusting the pH value of the mixture to 7.0 to prepare a vehicle solution, suspending the active ingredient into the vehicle solution, and then pulverizing the suspension). The mean primary particle diameter and the mean secondary particle diameter of aripiprazole monohydrate in each Production Example were measured immedi-

TABLE 1

| Component | Function | Example 1 | Example 2 | Example 3 | Example 4 | Example 5 | Example 6 | Example 7 |
|---|---|---|---|---|---|---|---|---|
| | | | | Quantity (mg/mL) | | | | |
| Aripiprazole monohydrate | Active ingredient | 416* | 416* | 416* | 416* | 416* | 416* | 416* |
| Carboxymethyl-cellulose sodium | Suspending agent | 5 | 5 | 5 | 5 | 10 | 10 | 8 |
| Povidone K17 | Suspending agent | 0.5 | 0.5 | 4 | 4 | 4 | 4 | — |
| Polyethylene glycol 400 | Suspending agent | — | 0.1 | 0.1 | — | 1 | — | — |
| Polyethylene glycol 4000 | Suspending agent | — | — | — | 1 | — | 1 | 0.1 |
| Sodium dihydrogen phosphate monohydrate | Buffer | 0.74 | 0.74 | 0.74 | 0.74 | 0.74 | 0.74 | 0.74 |
| Sodium chloride | Tonicity agent | 5.7 | 5.7 | 5.7 | 5.7 | 5.1 | 5.1 | 5.7 |
| Sodium hydroxide | pH Adjuster | q.s. | q.s. | q.s. | q.s. | q.s. | q.s. | q.s. |
| Water for injection | | q.s. | q.s. | q.s. | q.s. | q.s. | q.s. | q.s. |
| Mean particle diameter (µm) | Secondary particle diameter** | 4.1 | 4.2 | 3.6 | 4.8 | 4.1 | 5.2 | 6.3 |
| | Primary particle diameter*** | 2.7 | 2.7 | 2.4 | 2.8 | 2.9 | 3.1 | 4.5 |
| Viscosity (mPa · s) | | 77.1 | 72.0 | 72.2 | 63.8 | 91.8 | 88.3 | 157.7 |

*Concentration of aripiprazole monohydrate (400 mg/mL as an anhydride)
**In Examples 1 to 6, the measurement was performed in a batch cell without ultrasound irradiation. In Example 7, the measurement was performed in circulating water without ultrasonic irradiation.
***In Examples 1 to 6, the measurement was performed in circulating 0.2% hydroxypropylcellulose solvent with ultrasonic irradiation. In Example 7, the measurement was performed in circulating water with ultrasonic irradiation.

Test Example 1

The injectable preparations having the compositions shown in Table below (Production Examples A1 to A6) were produced in the same manner as in Examples 1 to 7 described above. ately after production. The results revealed that all Production Examples had a mean primary particle diameter of about 2.0 to 4.0 µm and a mean secondary particle diameter of about 2.0 to 7.5 µm (Table 2).

TABLE 2

| Component | Function | Production Example A1 | Production Example A2 | Production Example A3 | Production Example A4 | Production Example A5 | Production Example A6 |
|---|---|---|---|---|---|---|---|
| Aripiprazole monohydrate | Active ingredient | 312* | 312* | 312* | 312* | 312* | 312* |
| Povidone K17 | Suspending agent | 0.1 | 1 | 4 | 10 | 50 | 100 |
| Sodium dihydrogen-phosphate monohydrate | Buffer | 0.74 | 0.74 | 0.74 | 0.74 | 0.74 | 0.74 |
| Sodium chloride | Tonicity agent | 7.0 | 7.0 | 7.0 | 7.0 | 7.0 | 7.0 |
| Sodium hydroxide | pH Adjuster | q.s. | q.s. | q.s. | q.s. | q.s. | q.s. |
| Water for injection | | q.s. | q.s. | q.s. | q.s. | q.s. | q.s. |

TABLE 2-continued

| Component | Function | Production Example A1 | Production Example A2 | Production Example A3 | Production Example A4 | Production Example A5 | Production Example A6 |
|---|---|---|---|---|---|---|---|
| Mean particle diameter (μm) | Secondary particle diameter** | 7.3 | 2.8 | 2.3 | 2.5 | 2.3 | 2.3 |
| | Primary particle diameter*** | 3.6 | 2.2 | 2.2 | 2.2 | 2.3 | 2.3 |

*Concentration of aripiprazole monohydrate (300 mg/mL as an anhydride)
**In Examples A1 to A6, the measurement was performed in a circulating water medium without ultrasonic irradiation.
***In Examples A1 to A6, the measurement was performed in circulating water medium with ultrasonic irradiation.

After production, each preparation of the Production Examples was placed in a transparent container, and then stored in a still condition at 5° C., 25° C., or 40° C. for five days. FIG. 4a (stored at 5° C.), FIG. 4b (stored at 25° C.), and FIG. 4c (stored at 40° C.) show photographs of the injectable preparations each held in a container which was slowly tilted and laid horizontally after storage. In the explanation of Test Example 1 (in particular, in the Figures and Tables), Production Example A1, Production Example A2, Production Example A3, Production Example A4, Production Example A5, and Production Example A6 may respectively be referred to as "Povidone K17 0.1 mg/mL," "Povidone K17 1.0 mg/mL," "Povidone K17 4.0 mg/mL," "Povidone K17 10.0 mg/mL," "Povidone K17 50.0 mg/mL," and "Povidone K17 100 mg/mL."

From the results shown in FIGS. 4a to 4c, it was confirmed that the gelling tendency increases with a lower concentration of polyvinylpyrrolidone (Povidone K17), and that the gelling tendency increases with a higher standing temperature. However, when the sample was left standing at 90° C., water evaporated, making the sample unsuitable as an injectable preparation.

Each preparation of the Production Examples was stored at 5° C. After sufficiently shaking the preparations by hand to return them to a sol state (any preparation that remained in a sol state even after standing was also shaken to confirm that it was in a sol state), the viscosity of each preparation was measured using a rheometer. The viscosity measurements were conducted under the following conditions.

Measuring instrument: Rheometer (Discovery Hybrid Rheometer-2 (DHR-2) or Discovery Hybrid Rheometer-3 (DHR-3) (manufactured by TA instruments)
Shear rate: $10^{-5} \rightarrow 1{,}000$ (1/s)
Measuring temperature: 5, 25, or 40° C.
Concentric cylinder After being stored at 5° C., each preparation of the Production Examples was shaken by hand to form a sol, and 10 mL of each was placed in the measuring instrument. After being placed in the measuring instrument, each preparation was allowed to stand at the measuring temperatures for 5 to 10 minutes, and then the measurement was started (the intention being to form a gel in the measuring instrument by allowing it to stand in the measuring instrument, in the case where an injectable preparation can form a gel).

Hereunder, the viscosities of the injectable preparations (Production Examples) were measured using the same measuring instrument with the same range of shear rate change as described above, wherein a concentric cylinder was also used. Furthermore, the measurement was also started after the samples were allowed to stand for 5 to 10 minutes at the measuring temperatures after being placed in the measuring instrument as described above.

FIG. 5a (measuring temperature: 5° C.), FIG. 5b (measuring temperature: 25° C.), and FIG. 5c (measuring temperature: 40° C.) show the results of the viscosity measurement. Note that these Figures show the results measured at a shear rate in the range of $10^{-2}$ to 1,000 (1/s). Tables 3 to 5 summarize the data of specific viscosities obtained in each measurement, in terms of the viscosity measured at the shear rate in the range of 0.01 to 0.02 (1/s) and the viscosity measured at the shear rate in the range of 900 to 1,000 (1/s). Table 3 corresponds to the data of FIG. 5a, Table 4 corresponds to the data of FIG. 5b, and Table 5 corresponds to the data of FIG. 5c.

TABLE 3

(Measuring temperature: 5° C.)

| | Povidone K17 (mg/mL) | | | | | |
|---|---|---|---|---|---|---|
| | 0.1 | 1 | 4 | 10 | 50 | 100 |
| Shear rate (1/s) | Viscosity (Pa · s) | | | | | |
| 0.01-0.02 | 1203.6 | 155.6 | 14.8 | 83.3 | 13.7 | 22.5 |
| 900-1,000 | 0.024 | 0.012 | 0.009 | 0.010 | 0.015 | 0.024 |

TABLE 4

(Measuring temperature: 25° C.)

| | Povidone K17 (mg/mL) | | | | | |
|---|---|---|---|---|---|---|
| | 0.1 | 1 | 4 | 10 | 50 | 100 |
| Shear rate (1/s) | Viscosity (Pa · s) | | | | | |
| 0.01-0.02 | 3416.5 | 938.6 | 109.4 | 171.4 | 165.9 | 225.8 |
| 900-1,000 | 0.034 | 0.012 | 0.008 | 0.009 | 0.011 | 0.016 |

TABLE 5

(Measuring temperature 40° C.)

| | Povidone K17 (mg/mL) | | | | | |
|---|---|---|---|---|---|---|
| | 0.1 | 1 | 4 | 10 | 50 | 100 |
| Shear rate (1/s) | Viscosity (Pa · s) | | | | | |
| 0.01-0.02 | 3777.0 | 2145.0 | 1152.9 | 1053.2 | 987.1 | 1193.0 |
| 900-1,000 | 0.042 | 0.018 | 0.011 | 0.011 | 0.013 | 0.018 |

The results, in particular those in FIG. 5b and Table 4 (measurement results at 25° C.), indicate that when the concentration of polyvinylpyrrolidone is about 2 to 50 mg/mL, the lowest viscosity was attained at any shear rate, and also gelling was achieved. A tendency was confirmed such that the lower the concentration of polyvinylpyrrolidone, the higher the viscosity. At high concentrations of polyvinylpyrrolidone, the viscosity tended to become low until the concentration of polyvinylpyrrolidone reached about 20 to 50 mg/mL, and the viscosity tended to become high again when the concentration of polyvinylpyrrolidone reached as high as about 100 mg/mL or more.

Test Example

The injectable preparations (Production Examples B, C and D) having the compositions shown in Table 6 were produced in the same manner as in Examples 1 to 7 (i.e., mixing the components other than the active ingredient, adjusting the pH value of the mixture to 7.0 to prepare a vehicle solution, suspending the active ingredient into the vehicle solution, and then pulverizing the suspension). These injectable preparations gelled after standing at 25° C. or 40° C. These injectable preparations returned to a sol state when gently shaken by hand, even after they had once gelled. The measurement results of the aripiprazole monohydrate mean particle diameter were as follows. Production Example B had a mean primary particle diameter of 2.2 μm and a mean secondary particle diameter of 2.4 μm. Production Example C had a mean primary particle diameter of 4.2 μm and a mean secondary particle diameter of 4.3 μm. Production Example D had a mean primary particle diameter of 3.9 μm and a mean secondary particle diameter of 3.9 μm.

TABLE 6

| Component | Function | Production Example B | Production Example C | Production Example D |
|---|---|---|---|---|
| | | Quantity (mg/mL) | | |
| Aripiprazole monohydrate | Active ingredient | 312* | 416** | 624*** |
| Carboxymethylcellulose sodium | Suspending agent | 5 | 5 | 5 |
| Povidone K17 | Suspending agent | 4 | 4 | 4 |
| Polyethylene glycol 400 | Suspending agent | 1 | 1 | 1 |
| Sodium dihydrogenphosphate monohydrate | Buffer | 0.74 | 0.74 | 0.74 |
| Sodium chloride | Tonicity agent | 6.1 | 5.4 | 3.5 |
| Sodium hydroixde | pH Adjuster | q.s. | q.s. | q.s. |
| Water for injection | | q.s. | q.s. | q.s. |
| Mean particle diameter (μm) | Secondary particle diameter**** | 2.4 | 4.3 | 3.9 |
| | Primary particle diameter***** | 2.2 | 4.2 | 3.9 |

*Concentration of aripiprazole monohydrate (300 mg/mL as an anhydride)
**Concentration of aripiprazole monohydrate (400 mg/mL as an anhydride)
***Concentration of aripiprazole monohydrate (600 mg/mL as an anhydride)
****In Production Examples B to D, the measurement was performed in a circulating water medium without ultrasonic irradiation.
*****In Production Examples B to D, the measurement was performed in a circulating water medium without ultrasonic irradiation.

After being stored at 5° C., the injectable preparations of Production Examples to D were shaken by hand to form a sol state, and placed in a rheometer to measure the viscosity of each preparation at 5° C., 25° C., or 40° C. (measuring temperature). After being stored at 5° C., the injectable preparations of Production Examples B and C were in a form of sol. After being stored at 5° C., the injectable preparation of Production Example D was in a form of gel.

FIGS. 6 to 8 show the measurement results. Tables 7 to 9 show the specific viscosities measured at a shear rate in the range of 0.01 to 0.02 (1/s) and those measured at a shear rate in the range of 900 to 1,000 (1/s). (FIG. 6 and Table 7 show the measurement results of Production Example B, FIG. 7 and Table 8 show the measurement results of Production Example C, and FIG. 8 and Table 9 show the measurement results of Production Example D.)

TABLE 7

(Production Example B)

| Shear rate (1/s) | Measuring temperature | | |
|---|---|---|---|
| | 5° C. | 25° C. | 40° C. |
| | Viscosity (Pa · s) | | |
| 0.01-0.02 | 12.9 | 115.7 | 1645.4 |
| 900-1,000 | 0.030 | 0.018 | 0.019 |

TABLE 8

(Production Example C)

| Shear rate (1/s) | Measuring temperature | | |
|---|---|---|---|
| | 5° C. | 25° C. | 40° C. |
| | Viscosity (Pa · s) | | |
| 0.01-0.02 | 12.9 | 115.7 | 1645.4 |
| 900-1,000 | 0.030 | 0.018 | 0.019 |

TABLE 9

(Production Example D)

| Shear rate (1/s) | Measuring temperature | | |
|---|---|---|---|
| | 5° C. | 25° C. | 40° C. |
| | Viscosity (Pa · s) | | |
| 0.01-0.02 | 266.6 | 2007.0 | 9231.9 |
| 900-1,000 | 0.115 | 0.084 | 0.093 |

Test Example 3

The injectable preparation (Production Example E) having the composition shown in Table 10 was produced in the same manner as in Examples 1 to 7 (i.e., mixing the components other than the active ingredient, adjusting the pH value of the mixture to 7.0 to prepare a vehicle solution, suspending the active ingredient into the vehicle solution, and then pulverizing the suspension). The preparation of Production Example E returned to a sol upon being gently shaken by hand even if it had once gelled. The measurement results of the aripiprazole monohydrate mean particle diameter were as follows. Production Example E had a mean primary particle diameter of 5.4 μm and a mean secondary particle diameter of 9.5 μm.

TABLE 10

| Component | Function | Production Example E Quantity (mg/mL) |
|---|---|---|
| Aripiprazole monohydrate | Active ingredient | 208* |

TABLE 10-continued

| Component | Function | Production Example E Quantity (mg/mL) |
|---|---|---|
| Povidone K17 | Suspending agent | 0.1 |
| Sodium dihydrogenphosphate monohydrate | Buffer | 0.74 |
| Sodium chloride | Tonicity agent | 7.0 |
| Sodium hydroxide | pH Adjuster | q.s. |
| Water for injection | | q.s. |
| Mean particle diameter (μm) | Secondary particle diameter** | 9.5 |
| | Primary particle diameter*** | 5.4 |

*Concentration of aripiprazole monohydrate (200 mg/mL, as an anhydride)
**In Production Example E, the measurement was performed in a circulating water medium without ultrasonic irradiation.
***In Production Example E, the measurement was performed in a circulating water medium with ultrasonic irradiation.

After being stored at 5° C., the injectable preparation of Production Example E was shaken well by hand to form a sol state, and placed in a rheometer to measure the viscosity thereof at 5° C., 25° C., or 40° C. (measuring temperature). FIG. 9a shows the results. Table 11 shows the specific viscosities measured at a shear rate in the range of 0.01 to 0.02 (1/s) and those measured at a shear rate in the range of 900 to 1,000 (1/s).

TABLE 11

(Production Example E)

| | Measuring temperature | | |
|---|---|---|---|
| Shear rate (1/s) | 5° C. | 25° C. | 40° C. |
| | Viscosity (Pa · s) | | |
| 0.01-0.02 | 45.2 | 170.5 | 376.4 |
| 900-1,000 | 0.008 | 0.007 | 0.008 |

After production, the injectable preparation of Production Example E was stored in a still condition at 5° C., 25° C. or 40° C. for five days. The injectable preparation of Production Example E gelled under all conditions (FIG. 9b shows photographs of the injectable preparations each stored in a container in a still condition for five days, and FIG. 9c shows photographs of the containers each holding an injectable preparation therein, which were slowly tilted and laid horizontally after storage.)

The viscosity measurement results of Production Examples A1 to E indicate that when an injectable preparation has a viscosity measured at a shear rate in the range of 0.01 to 0.02 (1/s) of about 40 (Pa·s) or higher, the preparation is in a gel state, and when the shear rate becomes large, the preparation forms a sol. In particular, the results indicate that when an injectable preparation has a viscosity measured at a shear rate in the range of 900 to 1,000 (1/s) of about 0.2 Pa·s or lower, the preparation can be injected as is.

Test Example 4

The injectable preparations (Production Examples F1 and F2) having the compositions shown in Table 12 were produced in the same manner as in Examples 1 to 7 (i.e., mixing the components other than the active ingredient, adjusting the pH-value of the mixture to 7.0 to prepare a vehicle solution, suspending the active ingredient into the vehicle solution, and then pulverizing the suspension). The injectable preparations of Production Examples F1 and F2 did not gel. The measurement results of the aripiprazole monohydrate mean particle diameter were as follows. Production Example F1 had a mean primary particle diameter of 3.2 μm and a mean secondary particle diameter of 5.6 μm. Production Example F2 had a mean primary particle diameter of 2.7 μm and a mean secondary particle diameter of 2.7 μm.

TABLE 12

| Component | Function | Production Example F1 Quantity (mg/mL) | Production Example F2 Quantity (mg/mL) |
|---|---|---|---|
| Aripiprazole monohydrate | Active ingredient | 104* | 104* |
| Povidone K17 | Suspending agent | 0.1 | 4 |
| Sodium dihydrogenphosphate monohydrate | Buffer | 0.74 | 0.74 |
| Sodium chloride | Tonicity agent | 8.0 | 8.0 |
| Sodium hydroxide | pH Adjuster | q.s. | q.s. |
| Water for injection | | q.s. | q.s. |
| Mean particle diameter (μm) | Secondary particle diameter** | 5.6 | 2.7 |
| | Primary particle diameter*** | 3.2 | 2.7 |

*Concentration of aripiprazole monohydrate (100 mg/mL, as an anhydrate)
**In Production Examples F1 and F2, the measurement was performed in a circulating water medium without ultrasonic irradiation.
***In Production Example F1 and F2, the measurement was performed in a circulating water medium with ultrasonic irradiation.

After being stored at 5° C., the injectable preparations of Production Examples F1 and F2 were well shaken by hand, and placed in a rheometer to measure the viscosity thereof at 5° C. or 25° C. (measuring temperature). FIG. 10a shows the results.

Table 13 shows the specific viscosities measured at a shear rate in the range of 0.01 to 0.02 (1/s) and those measured at a shear rate in the range of 900 to 1,000 (1/s).

TABLE 13

(Production Examples F1 and F2)

| | Povidone K17 (mg/mL) | | | |
|---|---|---|---|---|
| | 0.1 | | 4.0 | |
| | Measuring temperature | | | |
| Shear rate (1/s) | 5° C. | 25° C. | 5° C. | 25° C. |
| | Viscosity (Pa · s) | | | |
| 0.01-0.02 | 13.1 | 20.4 | 0.52 | 1.17 |
| 900-1,000 | 0.010 | 0.006 | 0.009 | 0.005 |

After production, the injectable preparations of Production Examples F1 and F2 were stored in a still condition at 5° C., 25° C. or 40° C. for five days. As a result, the preparations of Production Examples F1 and F2 did not gel under any conditions. FIG. 10b shows photographs of the injectable preparations each stored in a container in a still condition for five days, and FIG. 10c shows photographs of the containers each holding an injectable preparation therein, which were slowly tilted and laid horizontally after storage. In the explanation of Test Example 4 (in particular, in the Figures and Tables), Production Example F1 and Production Example F2 may respectively be referred to as "Povidone K17 0.1 mg/mL" and "Povidone K17 4.0 mg/mL." In particular, FIG. 10b shows that precipitation of particles occurred both in Production Examples F1 and F2. This indicates that Production Examples F1 and F2 are unsuitable for the injectable preparation of the present invention that maintains uniform dispersion of particles by forming a gel.

The results of Test Examples 1 to 4 revealed that when an injectable preparation comprising a poorly soluble drug is produced using polyvinylpyrrolidone as a suspending agent, an injectable preparation that gels by standing and returns to a sol upon applying a mild impact (e.g., shaking by hand) can be obtained.

It was also revealed that, in particular, when aripiprazole is used as a poorly soluble drug, an injectable preparation that gels by standing and returns to a sol upon applying a mild impact (e.g., shaking by hand) can be produced by forming the preparation in such a manner that it has a specific mean primary particle diameter of aripiprazole and a concentration of aripiprazole in the range of 200 mg/mL to 600 mg/mL. It was further revealed that the preparation preferably gels by being stored in a still condition at a temperature of about 20 to 70° C. and returns to a sol when a slight impact is applied thereto.

Test Example 5

The injectable preparations (Production Examples G, H and I) having the compositions shown in Table 14 were produced in the same manner as in Examples 1 to 7 (i.e., mixing the components other than the active ingredient, adjusting the pH value of the mixture to 7.0 to prepare a vehicle solution, suspending the active ingredient into the vehicle solution, and then pulverizing the suspension). In the Production Examples, poorly soluble drugs other than aripiprazole were used (Table 14). After production, the viscosities of the injectable preparations of Production Examples G, H and I and the mean particle diameters of the poorly soluble drugs were measured in the same manner as in the Production Examples described above. The preparations of Production Examples G, H and I returned a sol state when gently shaken by hand even if they had once gelled.

TABLE 14

| Component | Function | Production Example G | Production Example H | Production Example I |
|---|---|---|---|---|
| | | Quantity (mg/mL) | | |
| Poorly soluble drug | Active ingredient | Ethyl 4-aminobenzoate | Probucol | Cilostazol |
| | Amount | 400 | 300 | 300 |
| Carboxymethylcellulose sodium | Suspending agent | 5 | 5 | 5 |
| Povidone K17 | Suspending agent | 4 | 50 | 4 |
| Polyethylene glycol 400 | Suspending agent | 1 | 1 | 1 |
| Sodium dihydrogenphosphate monohydrate | Buffer | 0.74 | 0.74 | 0.74 |
| Sodium chloride | Tonicity agent | 5.4 | 6.1 | 6.1 |
| Sodium hydroxide | pH Adjuster | q.s. | q.s. | q.s. |
| Water for injection | | q.s. | q.s. | q.s. |
| Mean particle diameter (μm) | Secondary particle diameter* | 71.5 | 5.7 | 6.2 |
| | Primary particle diameter** | 40.5 | 3.3 | 3.6 |

*In Production Examples G to I, the measurement was performed in a circulating water medium without ultrasonic irradiation.
**In Production Examples G to I, the measurement was performed in a circulating water medium with ultrasonic irradiation.

After production, each preparation of the Production Examples was placed in a transparent container and stored in a still condition at 5° C., 25° C., or 40° C. for five days. FIG. 11 shows photographs of the containers each holding an injectable preparation, which were slowly tilted and laid horizontally after storage.

After being stored at 5° C., each preparation of the Production Examples was shaken well by hand, and placed in a rheometer to measure the viscosity thereof at 5° C., 25° C., or 40° C. (measuring temperature) in the same manner as described above. FIG. 12 shows the viscosity measurement results of Production Example G. FIG. 13 shows the results of Production Example H. FIG. 14 shows the results of Production Example Z. Tables 15 to 17 summarize the data of the specific viscosities measured at a shear rate in the range of 0.01 to 0.02 (1/s) and those measured at a shear rate in the range of 900 to 1,000 (1/s). Table 15 corresponds to the data of FIG. 12, Table 16 corresponds to the data of FIG. 13, and Table 17 corresponds to the data of FIG. 14.

TABLE 15

(Production Example G)

| | Measuring temperature | | |
|---|---|---|---|
| | 5° C. | 25° C. | 40° C. |
| Shear rate (1/s) | Viscosity (Pa · s) | | |
| 0.01-0.02 | 11.6 | 181.0 | 611.7 |
| 900-1,000 | 0.053 | 0.032 | 0.033 |

TABLE 16

(Production Example H)

| | Measuring temperature | | |
|---|---|---|---|
| | 5° C. | 25° C. | 40° C. |
| Shear rate (1/s) | Viscosity (Pa · s) | | |
| 0.01-0.02 | 5.7 | 16.3 | 46.2 |
| 900-1,000 | 0.052 | 0.028 | 0.020 |

TABLE 17

(Production Example I)

| | Measuring temperature | | |
|---|---|---|---|
| | 5° C. | 25° C. | 40° C. |
| Shear rate (1/s) | Viscosity (Pa · s) | | |
| 0.01-0.02 | 73.3 | 218.0 | 1430.8 |
| 900-1,000 | 0.048 | 0.029 | 0.027 |

Test Example 6

The injectable preparation (Production Example J) having the composition shown in Table 18 was produced in the same manner as in Examples 1 to 7 (i.e., mixing the components other than the active ingredient, adjusting the pH value of the mixture to 7.0 to prepare a vehicle solution, suspending the active ingredient into the vehicle solution, and then pulverizing the suspension). The injectable preparation of Production Example J had gelled after standing at 5° C., 25° C., or 40° C. and it returned to a sol when gently shaken by hand even if it had once gelled. The measurement results of the aripiprazole monohydrate mean particle diameter were as follows. Production Example J had a mean primary particle diameter of 5.5 µm and a mean secondary particle diameter of 6.9 µm.

TABLE 18

| Component | Function | Production Example J Quantity (mg/mL) |
|---|---|---|
| Aripiprazole monohydrate | Active ingredient | 416* |
| Carbomethylcellulose sodium | Suspending agent | 5 |
| Polyethylene glycol 4000 | Suspending agent | 0.1 |
| Sodium dihydrogenphosphate monohydrate | Buffer | 0.74 |
| Sodium chloride | Tonicity agent | 5.7 |
| Sodium hydroxide | pH Adjuster | q.s. |
| Water for injection | | q.s. |
| Mean particle diameter (µm) | Secondary particle diamter** | 6.9 |
| | Primary particle diameter*** | 5.5 |

*Concentration of aripiprazole monohydrate (400 mg/mL as an anhydride)
**In Production Example J, the measurement was performed in a circulating water medium without ultrasonic irradiation.
***In Production Example J, the measurement was performed in a circulating water medium with ultrasonic irradiation.

After being stored at 5° C., the injectable preparation of Production Example J was shaken well by hand to form a sol state, and placed in a rheometer to measure the viscosity thereof at 5° C., 25° C., or 40° C. (measuring temperature). FIG. 15 shows the results. Table 19 shows the specific viscosities measured at a shear rate in the range of 0.01 to 0.02 (1/s) and those measured at a shear rate in the range of 900 to 1,000 (1/s). The injectable preparation of Production Example J gelled after being stored in a still condition at 5° C. for five days.

TABLE 19

| (Production Example J) | | | |
|---|---|---|---|
| | Measuring temperature | | |
| | 5° C. | 25° C. | 40° C. |
| Shear rate (1/s) | Viscosity (Pa · s) | | |
| 0.01-0.02 | 187.2 | 3593.0 | 10666.7 |
| 900-1,000 | 0.029 | 0.027 | 0.044 |

Test Example 7

The injectable preparations (Production Examples K and L) having the compositions shown in Table 20 below were produced in the same manner as in Examples 1 to 7 (i.e., mixing the components other than the active ingredient, adjusting the pH value of the mixture to 7.0 to prepare a vehicle solution, suspending the active ingredient into the vehicle solution, and then pulverizing the suspension). After production, an aging treatment was conducted by allowing the injectable preparations to stand at 60° C. for 12 hours. Freeze-dried injectable preparations containing aripiprazole in an amount of 200 mg/mL or 400 mg/mL (Comparative Example 200 or Comparative Example 400) were prepared in the same manner as disclosed in the Examples of WO2005/041937. The measurement results of the aripiprazole monohydrate mean particle diameter were as follows. Production Example K had a mean primary particle diameter of 2.8 µm and a mean secondary particle diameter of 4.3 µm. Production Example L had a mean primary particle diameter of 6.1 µm and a mean secondary particle diameter of 7.9 µm. Comparative Example 200 had a mean primary particle diameter of 2.1 µm and a mean secondary particle diameter of 2.1 µm. Comparative Example 400 had a mean primary particle diameter of 2.0 µm and a mean secondary particle diameter of 2.1 µm.

These injectable preparations were injected into the crural muscle of male rats at a dose of 50 mg/kg (Production Example K and Comparative Example 200) and at a dose of 100 mg/kg (Production Example L and Comparative Example 400). To evaluate the transfer of aripiprazole into the blood after administration, blood samples were collected 0.25, 1, 3, 6, 9, 14, 21, 28, 42, and 56 days after administration, and the concentration of aripiprazole in the serum of each sample was measured. The injectable preparations of Production Examples K and L were each packed into a vial after production and gelled by allowing them to stand therein. Before administration, the injectable preparations were gently shaken to turn the gel into a sol state, and then they were administered. The injectable preparations of Comparative Example 200 and Comparative Example 400 were once freeze dried, then reconstituted using water before administration.

FIG. 16 shows the obtained results in the form of a graph.

TABLE 20

| Component | Function | Production Example K | Production Example L | Comparative Example 200 | Comparative Example 400 |
|---|---|---|---|---|---|
| | | Quantity (mg/mL) | | | |
| Aripiprazole monohydrate | Active ingredient | 312* | 416** | 208*** | 416** |
| Carbomethylcellulose sodium | Suspending agent | 5 | 5 | 8.32 | 8 |
| Povidone K17 | Suspending agent | 4 | 4 | — | — |

TABLE 20-continued

| Component | Function | Production Example K | Production Example L | Comparative Example 200 | Comparative Example 400 |
|---|---|---|---|---|---|
| | | Quantity (mg/mL) | | | |
| Polyethylene glycol 400 | Suspending agent | 10 | 10 | — | — |
| Sodium dihydrogenphosphate monohydrate | Buffer | 0.74 | 0.74 | 0.74 | 0.74 |
| Sucrose | Tonicity agent | 50.5 | 46 | — | — |
| Mannitol | Tonicity agent | — | — | 41.6 | 31 |
| Sodium hydroxide | pH Adjuster | q.s. | q.s. | q.s. | q.s. |
| Water for injection | | q.s. | q.s. | q.s. | q.s. |
| Mean particle diameter (μm) | Secondary particle diameter**** | 4.3 | 7.9 | 2.1 | 2.1 |
| | Primary particle diameter***** | 2.8 | 6.1 | 2.1 | 2.0 |

*Concentration of aripiprazole monohydrate (300 mg/mL as an anhydride)
**Concentration of aripiprazole monohydrate (400 mg/mL as an anhydride)
***Concentration of aripiprazole monohydrate (200 mg/mL as an anhydride)
****The measurement was performed in a circulating water medium without ultrasonic irradiation.
*****The measurement was performed in a circulating water medium with ultrasonic irradiation.

Production Example K showed a pharmacokinetic (PK) profile of almost the same level as that of Comparative Example 200. The PK profile of Production Example K was desirable for a sustained-release injectable preparation that is administered once per month. Production Example L showed a lower $C_{max}$ than Comparative Example 400 and an equal or better sustained-release property. In other words, the PK profile of Production Example L is more preferable for a sustained-release injectable preparation that is administered once every two to three months.

Test Example 8

The viscosities of the injectable preparations (Production Examples A3 to A6) that were stored at 5° C. in Test Example 1 were re-measured. Specifically, the viscosity measurement was conducted in the same manner as in Test Example 1 except for the following steps. The injectable preparations of Production Examples A3 to A6 after being allowed to stand at 5° C. were in a sol state; however, before being placed in a rheometer, they were shaken by hand to confirm that they were in a sol state. Thereafter, they were allowed to stand at 40° C. for five minutes and returned to 25° C. in the rheometer to measure the viscosity thereof.

FIG. 17 shows the viscosity measurement results. Table 21 summarizes the data of specific viscosities measured at a shear rate in the range of 0.01 to 0.02 (1/s) and those measured at a shear rate in the range of 900 to 1,000 (1/s).

TABLE 21

(Production Examples A3 to A6)
After being allowed to stand at 40° C. for five minutes,
the measurement was conducted at 25° C.

| | PVP-17PF (mg/mL) | | | |
|---|---|---|---|---|
| | 4 | 10 | 50 | 100 |
| Shear rate (1/s) | Viscosity (Pa · s) | | | |
| 0.01-0.02 | 875.9 | 955.8 | 768.1 | 1029.6 |
| 900-1,000 | 0.011 | 0.012 | 0.017 | 0.024 |

Test Example 9

The viscosities of the injectable preparations (Production Examples B and C) that were stored at 5° C. in Test Example 2 were re-measured. Specifically, the viscosity measurement was conducted in the same manner as in Test Example 2 except for the following steps. The injectable preparations of Production Examples B and C after being allowed to stand at 5° C. were in a sol state; however, before being placed in a rheometer, they were shaken by hand to confirm that they were in a sol state. Thereafter, they were allowed to stand at 40° C. for five minutes and returned to 25° C. in the rheometer to measure the viscosity thereof.

FIG. 18 shows the viscosity measurement results. FIG. 18 also shows the viscosities measured at 5° C. and 25° C. in Test Example 2. Among the results shown in FIG. 18, Table 22 summarizes the data of specific viscosities measured at a shear rate in the range of 0.01 to 0.02 (1/s) and those measured at a shear rate in the range of 900 to 1,000 (1/s). In Table 22, "40→25" indicates that the viscosity was measured after the preparation was allowed to stand at 40° C. for five minutes in the rheometer and returned to 25° C. (this also applies to the following Tables).

TABLE 22

| | Production Example (Aripiprazole concentration) | | | | | |
|---|---|---|---|---|---|---|
| | Production Example B (300 mg/mL) | | | Production Example C (400 mg/mL) | | |
| | Measuring temperature (° C.) | | | | | |
| | 5 | 25 | 40→25 | 5 | 25 | 40→25 |
| Shear rate (1/s) | Viscosity (Pa · s) | | | | | |
| 0.01-0.02 | 16.9 | 245.8 | 741.3 | 12.9 | 115.7 | 1189.5 |
| 900-1,000 | 0.021 | 0.015 | 0.017 | 0.330 | 0.018 | 0.027 |

Test Example 10

The injectable preparation (Production Example E') was produced in the same manner as in producing Production Example E in Test Example 3 except that the concentration of Povidone K17 was changed from 0.1 mg/mL to 4 mg/mL. Thereafter, the preparation of Production Example E' was stored at 5° C., 25° C. or 40° C. The viscosities of the preparations of Production Examples E and E' after being allowed to stand at 5° C. were measured in the same manner as in Test Example 3. Specifically, the injectable preparation of Production Example E' after being allowed to stand at 5° C. was in a sol state; however, before being placed in a rheometer, the preparations of Production Examples E and E' were shaken by hand to confirm that they were in a sol state. Thereafter, they were allowed to stand at 40° C. for five minutes and returned to 25° C. in the rheometer to measure the viscosity thereof. The preparation of Production Example E' was also subjected to the viscosity measurement conducted in the same manner as in Test Example 3 (measuring temperatures: 5° C. and 25° C.).

FIG. 19a shows the viscosity measurement results. FIG. 19a also shows the viscosities of Production Example E measured at 5° C. and 25° C. in Test Example 3. Among the results shown in FIG. 19a, Table 23 summarizes the data of specific viscosities measured at a shear rate in the range of 0.01 to 0.02 (1/s) and those measured at a shear rate in the range of 900 to 1,000 (1/s).

TABLE 23

| | Production Example (Povidone concentration) | | | | | |
|---|---|---|---|---|---|---|
| | Production Example E (0.1 mg/mL) | | | Production Example E' 4.0 mg/mL | | |
| | Measuring temperature (° C.) | | | | | |
| Shear rate (1/s) | 5 | 25 | 40→25 | 5 | 25 | 40→25 |
| | Viscosity (Pa · s) | | | | | |
| 0.01-0.02 | 45.2 | 170.5 | 179.8 | 7.02 | 25.1 | 177.3 |
| 900-1,000 | 0.008 | 0.007 | 0.008 | 0.007 | 0.006 | 0.008 |

The injectable preparation of Production Example E' was stored in a still condition at 5° C., 25° C. or 40° C. for five days. Only the preparation stored at 40° C. gelled (FIG. 19b shows photographs of the containers each holding an injectable preparation, which were slowly tilted and laid horizontally after storage. In the Figure, Production Example E' may be referred to as "Povidone K17 4.0 mg/mL").

Test Example 11

Using 7-[4-(4-benzo[b]thiophen-4-yl-piperazin-1-yl)butoxy]-1H-quinolin-2-one dihydrate as an active ingredient, the injectable preparations having the compositions shown in Table 24 below (Production Examples M1 and M2) were produced in the same manner as in producing Production Examples A1 and A2 in Test Example 1. The 7-[4-(4-benzo[b]thiophen-4-yl-piperazin-1-yl)butoxy]-1H-quinolin-2-one dihydrate was obtained in Synthesis Example 1 described below.

Even after having once gelled, the injectable preparations of Production Examples 1 and 2 became a sol by being gently shaken by hand. The measurement results of the 7-[4-(4-benzo[b]thiophen-4-yl-piperazin-1-yl)butoxy]-1H-quinolin-2-one dihydrate mean particle diameter were as follows. Production Example M1 had a primary mean particle diameter of 8.8 μm and a secondary mean particle diameter of 10.8 μm. Production Example M2 had a primary mean particle diameter of 8.3 μm and a secondary mean particle diameter of 10.2 μm.

TABLE 24

| Component | Function | Production Example M1 Quantity (mg/mL) | Production Example M2 Quantity (mg/mL) |
|---|---|---|---|
| 7-[4-(4-Benzo[b]thiophen-4-yl-piperazin-1-yl)butoxy]-1H-quinolin-2-one dihydrate | Active ingredient | 324* | 324* |
| Povidone K17 | Suspending agent | 0.1 | 1.0 |
| Sodium dihydrogenphosphate monohydrate | Buffer | 0.74 | 0.74 |
| Sodium chloride | Tonicity agent | 7.0 | 7.0 |
| Sodium hydroxide | pH Adjuster | q.s. | q.s. |
| Water for injection | | q.s. | q.s. |
| Mean particle diameter (μm) | Secondary particle diameter** | 10.8 | 10.2 |
| | Primary particle diameter*** | 8.8 | 8.3 |

*Concentration of 7-[4-(4-benzo[b]thiophen-4-yl-piperazin-1-yl)butoxy]-1H-quinolin-2-one dihydrate (300 mg/mL as an anhydride)
**The measurement was performed in a circulating water medium without ultrasonic irradiation.
***The measurement was performed in a circulating water medium with ultrasonic irradiation.

The viscosities of the injectable preparations of Production Examples M1 and M2 after being allowed to stand at 5° C. were measured. Specifically, the preparation of Production Example M2 after being allowed to stand at 5° C. was in a sol state; however, before being placed in a rheometer, both the preparations of Production Examples M1 and M2 were shaken by hand to confirm that they were in a sol state, and the viscosities thereof were measured at 5° C., 25° C., or 40° C. (measuring temperature) in the same manner as in Test Example 1.

FIG. 20a shows the viscosity measurement results. Among the results shown in FIG. 20a, Table 25 summarizes the data of specific viscosities measured at a shear rate in the range of 0.01 to 0.02 (1/s) and those measured at a shear rate in the range of 900 to 1,000 (1/s).

TABLE 25

| | Production Example (Povidone concentration) | | | | | |
|---|---|---|---|---|---|---|
| | Production Example M1 (0.1 mg/mL) | | | Production Example M2 1 mg/mL | | |
| | Measuring temperatur (° C. | | | | | |
| Shear rate (1/s) | 5 | 25 | 40 | 5 | 25 | 40 |
| | Viscosity (Pa · s) | | | | | |
| 0.01-0.02 | 176.7 | 816.6 | 1791.5 | 19.0 | 63.7 | 208.8 |
| 900-1,000 | 0.031 | 0.030 | 0.038 | 0.009 | 0.008 | 0.008 |

After production, the injectable preparations of Production Examples M1 and M2 were stored in a still condition at 5° C., 25° C. or 40° C. for five days. All of them gelled except the preparation of Production Example M2 stored at 5° C. (FIG. 20b shows photographs of the containers each holding an injectable preparation, which were slowly tilted and laid horizontally after being allowed to stand for five days. In the explanation of Test Example 11, Production Example M1 and Production Example M2 may respectively be referred to as "Povidone K17 0.1 mg/mL" and "Povidone K17 1.0 mg/mL").

Synthesis Example 1

Methanol (149 L), 7-hydroxy-1H-quinolin-2-one (14.87 kg), and potassium hydroxide (6.21 kg) were mixed in a reaction vessel, and the resulting mixture was stirred. After dissolution, 1-bromo-4-chlorobutane (47.46 kg) was added thereto, and the resulting mixture was stirred under reflux for seven hours. Thereafter, the mixture was stirred at 10° C. for one hour. The precipitated crystal was centrifuged and washed with methanol (15 L). The wet crystal was collected and placed in a tank. Water (149 L) was added thereto, followed by stirring at room temperature. After centrifugation, the result was washed with water (30 L). The wet crystal was collected and placed in a tank. After adding methanol (74 L), the mixture was stirred under reflux for one hour, cooled to 10° C., and then stirred. The precipitated crystal was centrifuged and washed with methanol (15 L). The separated crystal was dried at 60° C. to obtain 7-(4-chlorobutoxy)-1H-quinolin-2-one (15.07 kg).

Thereafter, water (20 L), potassium carbonate (1.84 kg), 1-benzo[b]thiophen-4-yl-piperazine hydrochloride (3.12 kg), and ethanol (8 L) were mixed in a reaction vessel, and then stirred at 50° C. 7-(4-Chlorobutoxy)-1H-quinolin-2-one (2.80 kg) was added to the mixture, and stirred under reflux for nine hours. After concentrating the solvent to 8 L under ordinary pressure, the mixture was stirred at 90° C. for one hour, and then cooled to 9° C. The precipitated crystal was centrifuged, and then sequentially washed with water (8 L) and ethanol (6 L). The separated crystal was dried at 60° C. to obtain a crude product. The crude product (4.82 kg) and ethanol (96 L) were mixed in a reaction vessel, and acetic acid (4.8 L) was introduced into the reaction vessel. The mixture was stirred under reflux for one hour to dissolve the crude product. After introducing hydrochloric acid (1.29 kg), the mixture was cooled to 10° C. The mixture was heated again, refluxed for one hour, and cooled to 7° C. The precipitated crystal was centrifuged and washed with ethanol (4.8 L). The separated crystal was dried at 60° C. to obtain 7-[4-(4-benzo[b]thiophen-4-yl-piperazin-1-yl)butoxy]-1H-quinolin-2-one hydrochloride (5.09 kg). The resulting 7-[4-(4-benzo[b]thiophen-4-yl-piperazin-1-yl)butoxy]-1H-quinolin-2-one hydrochloride (5.00 kg), ethanol (45 L), and water (30 L) were mixed in a reaction vessel. The mixture was stirred under reflux to dissolve the 7-[4-(4-benzo[b]thiophen-4-yl-piperazin-1-yl)butoxy]-1H-quinolin-2-one hydrochloride. Activated carbon (500 g) and water (5 L) were added thereto, and an activated carbon treatment was conducted under reflux for 30 minutes. After performing hot filtration, a solution containing sodium hydrate (511 g) dissolved in water (1.5 L) was flowed into the reaction vessel while stirring the filtrate under reflux. After stirring under reflux for 30 minutes, water (10 L) was introduced thereto, and the mixture was cooled to approximately 40° C. The precipitated crystal was centrifuged and washed with water (125 L). The separated crystal was dried at 80° C. to obtain 7-[4-(4-benzo[b]thiophen-4-yl-piperazin-1-yl)butoxy]-1H-quinolin-2-one (3.76 kg).

The 7-[4-(4-benzo[b]thiophen-4-yl-piperazin-1-yl)butoxy]-1H-quinolin-2-one (3.2 kg) obtained above, ethanol (64 L), water (74 L), and acetic acid (1.77 kg) were mixed in a reaction vessel to prepare an acid liquid mixture. The liquid mixture was stirred under reflux to dissolve the 7-[4-(4-benzo[b]thiophen-4-yl-piperazin-1-yl)butoxy]-1H-quinolin-2-one (reflux temperature: 84° C.). After cooling to −5° C., the solution obtained above was introduced, over a period of 30 minutes, into a solution containing 25% sodium hydroxide (5.9 kg) and water (54 L) that was cooled to 0° C., to prepare a liquid mixture with pH10. After stirring at 5° C. or below for one hour, the mixture was heated to 20 to 30° C. and further stirred for seven hours to conduct solid-liquid separation. Washing with water (320 L) was performed until alkali in the solid component disappeared (i.e., until the pH value of the filtrate became 7). The solid component was then air-dried until its weight became constant (i.e., until there was no longer any change of weight observed) to obtain a white solid 7-[4-(4-benzo[b]thiophen-4-yl-piperazin-1-yl)butoxy]-1H-quinolin-2-one dihydrate (unground, 3.21 kg).

The invention claimed is:

1. An injectable preparation comprising a composition comprising a poorly soluble drug, a dispersion medium, and a suspending agent, the suspending agent containing polyvinylpyrrolidone, the composition having a viscosity of 40 Pa·s or more in at least one point in the shear rate range of 0.01 to 0.02 s$^{-1}$ and having a viscosity of 0.2 Pa·s or less in at least one point in the shear rate range of 900 to 1,000 s$^{-1}$, as measured by a rheometer at 5° C., 25° C. or 40° C.,
   wherein the poorly soluble drug is aripiprazole or a salt thereof, or 7-[4-(4-benzo[b]thiophen-4-yl-piperazin-1-yl)butoxy]-1H-quinolin-2-one or a salt thereof,
   the poorly soluble drug has a mean primary particle diameter of 30 μm or less and is contained in a concentration of 200 to 600 mg/mL, and
   K value of polyvinylpyrrolidone is 12 to 30, and the concentration of polyvinylpyrrolidone is 0.1 to 100 mg/mL.

2. The injectable preparation according to claim 1, wherein the composition has a viscosity of 40 Pa·s or more in at least one point in the shear rate range of 0.01 to 0.02 s$^{-1}$ and having a viscosity of 0.2 Pa·s or less in at least one point in the shear rate range of 900 to 1,000 s$^{-1}$, as measured by a rheometer at 25° C.

3. The injectable preparation according to claim 1 comprising a composition comprising at least water as a dispersion medium.

4. The injectable preparation according to claim 1, wherein the suspending agent further contains polyethylene glycol.

5. The injectable preparation according to claim 1, wherein the suspending agent further contains polyethylene glycol and carboxymethyl cellulose or a salt thereof.

6. A gel composition comprising
   a poorly soluble drug which is aripiprazole or a salt thereof, or 7-[4-(4-benzo[b]thiophen-4-yl-piperazin-1-yl)butoxy]-1H-quinolin-2-one or a salt thereof,
   water, and
   suspending agent,
   wherein the suspending agent contains polyvinylpyrrolidone, the poorly soluble drug has a mean primary particle diameter of 0.5 to 30 μm and is contained in a concentration of 200 to 600 mg/mL, and
   K value of polyvinylpyrrolidone is 12 to 30, and the concentration of polyvinylpyrrolidone is 0.1 to 100 mg/mL.

7. The composition according to claim 6, wherein the suspending agent further contains polyethylene glycol.

8. The composition according to claim 6, wherein the suspending agent further contains polyethylene glycol and carboxymethyl cellulose or a salt thereof.

9. The composition according to claim 8, wherein the concentration of polyethylene glycol is 0.05 to 2 mg/mL, and the concentration of carboxymethyl cellulose or a salt thereof is 0.5 to 50 mg/m L.

10. The composition according to claim 6, wherein the poorly soluble drug has a mean secondary particle diameter that is up to but not exceeding three times the mean primary particle diameter thereof.

11. The composition according to claim 6, which has a viscosity of 40 Pa·s or more in at least one point in the shear rate range of 0.01 to 0.02 $s^{-1}$ and which has a viscosity of 0.2 Pa·s or less in at least one point in the shear rate range of 900 to 1,000 $s^{-1}$, as measured by a rheometer at 5° C., 25° C. or 40° C.

12. The composition according to claim 6 which has a viscosity of 40 Pa·s or more in at least one point in the shear rate range of 0.01 to 0.02 $s^{-1}$ and which has a viscosity of 0.2 Pa·s or less in at least one point in the shear rate range of 900 to 1,000 $s^{-1}$, as measured by a rheometer at 25° C.

13. A sustained release injectable preparation comprising a composition comprising
   a poorly soluble drug which is aripiprazole or a salt thereof, or 7-[4-(4-benzo[b]thiophen-4-yl-piperazin-1-yl)butoxy]-1H-quinolin-2-one or a salt thereof,
   water, and
   suspending agent,
   wherein the suspending agent contains polyvinylpyrrolidone,
   the poorly soluble drug has a mean primary particle diameter of 1 to 10 µm and is contained in a concentration of 200 to 400 mg/mL, and
   K value of polyvinylpyrrolidone is 12 to 30, and the concentration of polyvinylpyrrolidone is 0.1 to 100 mg/mL,
   the composition being in the form of a gel when allowed to stand, and changing to a sol when subjected to an impact, and
   the preparation being administered once per month.

14. The injectable preparation according to claim 13, wherein the poorly soluble drug has a mean primary particle diameter of 2 to 7 µm.

15. A sustained release injectable preparation comprising a composition comprising
   a poorly soluble drug which is aripiprazole or a salt thereof, or 7-[4-(4-benzo[b]thiophen-4-yl-piperazin-1-yl)butoxy]-1H-quinolin-2-one or a salt thereof,
   water, and
   suspending agent,
   wherein the suspending agent contains polyvinylpyrrolidone,
   the poorly soluble drug has a mean primary particle diameter of 4 to 30 µm and is contained in a concentration of 300 to 600 mg/mL, and
   K value of polyvinylpyrrolidone is 12 to 30, and the concentration of polyvinylpyrrolidone is 0.1 to 100 mg/mL,
   the composition being in the form of a gel when allowed to stand, and changing to a sol when subjected to an impact, and
   the preparation being administered once every two to three months.

16. The injectable preparation according to claim 15, wherein the poorly soluble drug has a mean primary particle diameter of 5 to 20 µm.

17. The injectable preparation according to claim 13, wherein the suspending agent further contains polyethylene glycol.

18. The injectable preparation according to claim 13, wherein the suspending agent further contains polyethylene glycol and carboxymethyl cellulose or a salt thereof.

19. The injectable preparation according to claim 18, wherein the concentration of polyethylene glycol is 0.05 to 2 mg/mL, and the concentration of carboxymethyl cellulose or a salt thereof is 0.5 to 50 mg/mL.

20. The injectable preparation according to claim 13, wherein the poorly soluble drug has a mean secondary particle diameter that is up to but not exceeding three times the mean primary particle diameter thereof.

21. The injectable preparation according to claim 13, wherein the composition has a viscosity of 40 Pa·s or more in at least one point in the shear rate range of 0.01 to 0.02 $s^{-1}$ and has a viscosity of 0.2 Pa·s or less in at least one point in the shear rate range of 900 to 1,000 $s^{-1}$, as measured by a rheometer at 5° C., 25° C. or 40° C.

22. The injectable preparation according to claim 13, wherein the composition has a viscosity of 40 Pa·s or more in at least one point in the shear rate range of 0.01 to 0.02 $s^{-1}$ and has a viscosity of 0.2 Pa·s or less in at least one point in the shear rate range of 900 to 1,000 $s^{-1}$, as measured by a rheometer at 25° C.

23. A method for treating a recurrence of schizophrenia, bipolar disorder, or depression, the method comprising administering the injectable preparation according to claim 1.

24. The method according to claim 23, wherein the injectable preparation is administered intramuscularly or subcutaneously.

* * * * *

UNITED STATES PATENT AND TRADEMARK OFFICE
CERTIFICATE OF CORRECTION

PATENT NO. : 11,097,007 B2  
APPLICATION NO. : 17/108939  
DATED : August 24, 2021  
INVENTOR(S) : Daiki Kaneko et al.

Page 1 of 1

It is certified that error appears in the above-identified patent and that said Letters Patent is hereby corrected as shown below:

In the Specification

Column 36, Table 7:

| TABLE 7 | | | |
|---|---|---|---|
| (Production Example B) | | | |
| | Measuring temperature | | |
| Shear rate (1/s) | 5° C. | 25° C. | 40° C. |
| | | Viscosity (Pa · s) | |
| 0.01-0.02 | 12.9 | 115.7 | 1645.4 |
| 900-1,000 | 0.030 | 0.018 | 0.019 |

Should read:  
Table 7  
(Production Example B)

| Measuring temperature | 5°C | 25°C | 40°C |
|---|---|---|---|
| Shear rate (1/s) | Viscosity (Pa·s) | | |
| 0.01-0.02 | 16.9 | 245.8 | 1527.3 |
| 900-1,000 | 0.021 | 0.015 | 0.018 |

Signed and Sealed this  
Twenty-fourth Day of January, 2023

Katherine Kelly Vidal  
*Director of the United States Patent and Trademark Office*